United States Patent
Cheng et al.

(10) Patent No.: US 10,633,453 B2
(45) Date of Patent: Apr. 28, 2020

(54) ANTIBODY LOCKER FOR THE INACTIVATION OF PROTEIN DRUG

(71) Applicants: DCB-USA LLC, Wilmington, DE (US); KAOHSIUNG MEDICAL UNIVERSITY, Kaohsiung (TW)

(72) Inventors: Tian-Lu Cheng, Kaohsiung (TW); Chih-Hung Chuang, Kaohsiung (TW); Hsiu-Fen Ko, Kaohsiung (TW); Yun-Chi Lu, Kaohsiung (TW)

(73) Assignees: KAOHSIUNG MEDICAL UNIVERSITY, Kaohsuing (TW); DCB-USA LLC, Wilmington, DE (US)

( * ) Notice: Subject to any disclaimer, the term of this patent is extended or adjusted under 35 U.S.C. 154(b) by 755 days.

(21) Appl. No.: 14/893,509

(22) PCT Filed: May 28, 2014

(86) PCT No.: PCT/US2014/039821
§ 371 (c)(1),
(2) Date: Mar. 14, 2016

(87) PCT Pub. No.: WO2014/193973
PCT Pub. Date: Dec. 4, 2014

(65) Prior Publication Data
US 2016/0185875 A1    Jun. 30, 2016

Related U.S. Application Data

(60) Provisional application No. 61/827,763, filed on May 28, 2013.

(51) Int. Cl.
| A61K 39/395 | (2006.01) |
| C07K 16/32 | (2006.01) |
| C07K 16/24 | (2006.01) |
| C07K 16/28 | (2006.01) |
| A61K 39/00 | (2006.01) |

(52) U.S. Cl.
CPC ........ *C07K 16/32* (2013.01); *A61K 39/39558* (2013.01); *C07K 16/241* (2013.01); *C07K 16/244* (2013.01); *C07K 16/245* (2013.01); *C07K 16/2818* (2013.01); *C07K 16/2863* (2013.01); *C07K 16/2866* (2013.01); *C07K 16/2869* (2013.01); *C07K 16/2875* (2013.01); *A61K 2039/505* (2013.01); *C07K 2317/53* (2013.01); *C07K 2317/76* (2013.01)

(58) Field of Classification Search
None
See application file for complete search history.

(56) References Cited

U.S. PATENT DOCUMENTS

| 5,932,448 A | 8/1999 | Tso et al. |
| 7,238,505 B2 | 7/2007 | Hwang et al. |
| 7,612,181 B2 | 11/2009 | Wu et al. |
| 8,513,390 B2 | 8/2013 | Stagliano et al. |
| 8,541,203 B2 | 9/2013 | Daugherty et al. |
| 8,658,774 B2 | 2/2014 | Williams et al. |
| 2003/0219402 A1 | 11/2003 | Rutter |
| 2004/0014652 A1 | 1/2004 | Trouet et al. |
| 2004/0109855 A1 | 6/2004 | Waldmann et al. |
| 2006/0018903 A1 | 1/2006 | Hellendoorn et al. |
| 2008/0107660 A1 | 5/2008 | Self |
| 2008/0292628 A1 | 11/2008 | Hui |
| 2010/0029497 A1 | 2/2010 | Himmler et al. |
| 2010/0189727 A1 | 7/2010 | Rodeck et al. |
| 2010/0247555 A1 | 9/2010 | Self et al. |
| 2010/0248279 A1* | 9/2010 | Yamauchi ............... C12Q 1/32 435/14 |
| 2011/0229476 A1 | 9/2011 | Liy et al. |
| 2011/0287009 A1* | 11/2011 | Scheer ................. C07K 16/244 424/136.1 |
| 2012/0244154 A1* | 9/2012 | Daugherty ......... C07K 16/2818 424/134.1 |
| 2012/0302737 A1 | 11/2012 | Christensen et al. |

(Continued)

FOREIGN PATENT DOCUMENTS

| WO | WO 95/011703 A1 | 5/1995 |
| WO | WO 96/034892 A1 | 11/1996 |
| WO | WO 04/009638 A1 | 1/2004 |
| WO | WO 04/111608 A2 | 12/2004 |
| WO | WO 09/021754 A2 | 2/2009 |
| WO | WO 09/024771 A2 | 2/2009 |
| WO | WO 2009/025846 A2 | 2/2009 |
| WO | WO 10/077643 A1 | 7/2010 |
| WO | WO 2010/081173 A2 | 7/2010 |
| WO | WO 13/128194 A1 | 9/2013 |
| WO | WO 13/148248 A1 | 10/2013 |
| WO | WO 14/052462 A2 | 4/2014 |

(Continued)

OTHER PUBLICATIONS

EP Application No. 14803825.0, Supplementary European Search Report dated Dec. 23, 2016.

(Continued)

*Primary Examiner* — Meera Natarajan
(74) *Attorney, Agent, or Firm* — Hannah Tien

(57) ABSTRACT

Disclosed herein is a hinge antibody capable of being selectively activated in a target cell or tissue to treat a condition therein. The hinge antibody includes a functional antibody, two inhibitory domains and four cleavable linkers. The functional antibody is capable of treating the condition in an activated state, and has two light chains and two heavy chains. Each inhibitory domain includes a hinge domain of an immunoglobulin and consists of two peptide arms. Each cleavable linker includes a peptide substrate cleavable by an enzyme specifically or highly expressed in the target cell or tissue, and connects one of the peptide arms of the inhibitory domains to the N-terminal of one of the light chains and heavy chains of the functional antibody. Also disclosed herein are methods for preparing and using this hinge antibody.

10 Claims, 7 Drawing Sheets
Specification includes a Sequence Listing.

(56) References Cited

U.S. PATENT DOCUMENTS

| | | | |
|---|---|---|---|
| 2013/0011394 A1* | 1/2013 | Knoetgen | C07K 14/70539 424/133.1 |
| 2013/0266568 A1 | 10/2013 | Brinkmann et al. | |
| 2013/0267686 A1 | 10/2013 | Brinkmann et al. | |
| 2013/0315906 A1 | 11/2013 | Lowman et al. | |
| 2014/0010810 A1 | 1/2014 | West et al. | |
| 2014/0023664 A1 | 1/2014 | Lowman et al. | |

FOREIGN PATENT DOCUMENTS

| | | |
|---|---|---|
| WO | WO 2014/144689 A1 | 9/2014 |
| WO | WO 14/193973 A2 | 12/2014 |
| WO | WO 15/013671 A1 | 1/2015 |
| WO | WO 15/048329 A2 | 4/2015 |
| WO | WO 15/066279 A2 | 5/2015 |
| WO | WO 15/113671 A1 | 8/2015 |

OTHER PUBLICATIONS

Ho et al., "Comparison of Internal Ribosome Entry Site (IRES) and Furin-2A (F2A) for Monoclonal Antibody Expression Level and Quality in CHO Cells," PLoS ONE, 8(5):e63247, 12 pages, doi:10.1371/journal.pone.0063247, (2013).

Desnoyers et al., "Tumor-Specific Activation of an EGFR-Targeting Probody Enhances Therapeutic Index," Sci Transl Med, vol. 5, Issue 207ra144, DOI: 10.1126/scitranslmed.3006682, 10 pages, (2013).

Donaldson et al., "Design and development of masked therapeutic antibodies to limit off-target effects Application to anti-EGFR antibodies," Cancer Biology & Therapy, 8(2):2145-2150:2152, (2009).

Erster et al., "Site-specific targeting of antibody activity in vivo mediated by dieseaese-associated proteases," Journal of Controlled Release, 161:804-815, (2012).

Janssen et al., "Reversible blocking of antibodies using bivalent peptide-DNA conjugates allows protease-activatable targeting," Chem Sci, 4:1442-1450, (2013).

Metz et al., "Bispecific antibody derivatives with restricted binding functionalities that are activated by proteolytic processing," Protein Engineering, Design & Selection, 25(10):571-580, (2012).

Polu et al., "ProbodyTM therapeutics for targeting antibodies to dieseased tissue," Expert Opin. Biol. Ther., 14(8):1-5, (2014).

Thompson et al., "Light-activated antibodies in the fight against primary and metastatic cancer," Drug Discovery Today, 15(11/12):468-473, (2010).

Thompson et al., "Preclinical evaluation of light-activatable, bispecific anti-human CD3 antibody conjugates as anti-ovarian cancer therapeutics," mAbs, 1(4):348-365 (2009).

Thompson et al., "The construction and in vitro testing of photo-activatable cancer targeting folated anti-CD3 conjugates," Biochemical and Biophysical Research Communications, 366:526-531, (2008).

Weidle et al., "Proteases as Activators for Cytotoxic Prodrugs in Antitumor Therapy," Cancer Genomics & Proteomics, 11:67-80, (2014).

WIPO Application No. PCT/US2014/039821, PCT International Preliminary Report on Patentability dated Dec. 1, 2015.

WIPO Application No. PCT/US2014/039821, PCT International Search Report dated Dec. 17, 2014.

WIPO Application No. PCT/US2014/039821, PCT Written Opinion of the International Searching Authority dated Dec. 17, 2014.

* cited by examiner

Disease site

SEQUENCE LISTING

```
<160> NUMBER OF SEQ ID NOS: 78

<210> SEQ ID NO 1
<211> LENGTH: 214
<212> TYPE: PRT
<213> ORGANISM: Artificial Sequence
<220> FEATURE:
<223> OTHER INFORMATION: infliximab light chain

<400> SEQUENCE: 1

Asp Ile Leu Leu Thr Gln Ser Pro Ala Ile Leu Ser Val Ser Pro Gly
1               5                   10                  15

Glu Arg Val Ser Phe Ser Cys Arg Ala Ser Gln Phe Val Gly Ser Ser
            20                  25                  30

Ile His Trp Tyr Gln Gln Arg Thr Asn Gly Ser Pro Arg Leu Leu Ile
        35                  40                  45

Lys Tyr Ala Ser Glu Ser Met Ser Gly Ile Pro Ser Arg Phe Ser Gly
    50                  55                  60

Ser Gly Ser Gly Thr Asp Phe Thr Leu Ser Ile Asn Thr Val Glu Ser
65                  70                  75                  80

Glu Asp Ile Ala Asp Tyr Tyr Cys Gln Gln Ser His Ser Trp Pro Phe
                85                  90                  95

Thr Phe Gly Ser Gly Thr Asn Leu Glu Val Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160
```

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Leu Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 2
<211> LENGTH: 221
<212> TYPE: PRT
<213> ORGANISM: Artificial Sequence
<220> FEATURE:
<223> OTHER INFORMATION: Panitumumab light chain

<400> SEQUENCE: 2

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Asn Ile Val His Asn
            20                  25                  30

Asn Gly Ile Thr Tyr Leu Glu Trp Tyr Leu Gln Lys Pro Gly Gln Ser
        35                  40                  45

Pro Gln Leu Leu Ile Tyr Lys Val Ser Asp Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Ile Pro Pro Thr Phe Gly Gln Gly Thr Lys Val Glu Ile Lys
            100                 105                 110

Arg Ala Arg Thr Val Ala Ala Pro Ser Val Phe Ile Phe Pro Pro Ser
        115                 120                 125

Asp Glu Gln Leu Lys Ser Gly Thr Ala Ser Val Val Cys Leu Leu Asn
    130                 135                 140

Asn Phe Tyr Pro Arg Glu Ala Lys Val Gln Trp Lys Val Asp Asn Ala
145                 150                 155                 160

Leu Gln Ser Gly Asn Ser Gln Glu Ser Val Thr Glu Gln Asp Ser Lys
                165                 170                 175

Asp Ser Thr Tyr Ser Leu Ser Thr Leu Thr Leu Ser Lys Ala Asp
            180                 185                 190

Tyr Glu Lys His Lys Leu Tyr Ala Cys Glu Val Thr His Gln Gly Leu
        195                 200                 205

Ser Ser Pro Val Thr Lys Ser Phe Asn Arg Gly Glu Cys
    210                 215                 220

<210> SEQ ID NO 3
<211> LENGTH: 215
<212> TYPE: PRT
<213> ORGANISM: Artificial Sequence
<220> FEATURE:
<223> OTHER INFORMATION: Trastuzumab light chain

<400> SEQUENCE: 3

Ala Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Asp Val Asn Thr

```
            20                  25                  30
Ala Val Ala Trp Tyr Gln Gln Lys Pro Gly Lys Ala Pro Lys Leu Leu
        35                  40                  45

Ile Tyr Ser Ala Ser Phe Leu Tyr Ser Gly Val Pro Ser Arg Phe Ser
    50                  55                  60

Gly Ser Arg Ser Gly Thr Asp Phe Thr Leu Thr Ile Ser Ser Leu Gln
65                  70                  75                  80

Pro Glu Asp Phe Ala Thr Tyr Tyr Cys Gln Gln His Tyr Thr Thr Pro
                85                  90                  95

Pro Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 4
<211> LENGTH: 215
<212> TYPE: PRT
<213> ORGANISM: Artificial Sequence
<220> FEATURE:
<223> OTHER INFORMATION: adalimumab light chain

<400> SEQUENCE: 4

Ala Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Gly Ile Arg Asn
            20                  25                  30

Tyr Leu Ala Trp Tyr Gln Gln Lys Pro Gly Lys Ala Pro Lys Leu Leu
        35                  40                  45

Ile Tyr Ala Ala Ser Thr Leu Gln Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Val Ala Thr Tyr Tyr Cys Gln Arg Tyr Asn Arg Ala Pro
                85                  90                  95

Tyr Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
```

```
                165                 170                 175
Ser Ser Thr Leu Thr Leu Ser Lys Ala Asp Tyr Glu Lys His Lys Leu
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 5
<211> LENGTH: 215
<212> TYPE: PRT
<213> ORGANISM: Artificial Sequence
<220> FEATURE:
<223> OTHER INFORMATION: DENOSUMAB LIGHT CHAIN

<400> SEQUENCE: 5

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Arg Gly Arg
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Phe Tyr Cys Gln Gln Tyr Gly Ser Ser Pro
                85                  90                  95

Arg Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Leu
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 6
<211> LENGTH: 215
<212> TYPE: PRT
<213> ORGANISM: Artificial Sequence
<220> FEATURE:
<223> OTHER INFORMATION: Ipilimumab light chain

<400> SEQUENCE: 6

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Ser Ser
            20                  25                  30
```

-continued

```
Tyr Leu Ala Trp Tyr Gln Gln Lys Pro Gly Gln Ala Pro Arg Leu Leu
            35                  40                  45

Ile Tyr Gly Ala Phe Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Leu
            180                 185                 190

Tyr Ala Cys Glu Val Thr His Gln Gly Leu Ser Ser Pro Val Thr Lys
            195                 200                 205

Ser Phe Asn Arg Gly Glu Cys
            210                 215

<210> SEQ ID NO 7
<211> LENGTH: 214
<212> TYPE: PRT
<213> ORGANISM: Artificial Sequence
<220> FEATURE:
<223> OTHER INFORMATION: tremelimumab light chain

<400> SEQUENCE: 7

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Asn Ser Tyr
            20                  25                  30

Leu Asp Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Tyr Ser Thr Pro Phe
                85                  90                  95

Thr Phe Gly Pro Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175
```

```
Ser Thr Leu Thr Leu Ser Lys Ala Asp Tyr Glu Lys His Lys Leu Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 8
<211> LENGTH: 219
<212> TYPE: PRT
<213> ORGANISM: Artificial Sequence
<220> FEATURE:
<223> OTHER INFORMATION: efalizumab light chain

<400> SEQUENCE: 8

Ala Ala Gln Pro Ala Asp Ile Gln Met Thr Gln Ser Pro Ser Ser Leu
1               5                   10                  15

Ser Ala Ser Val Gly Asp Arg Val Thr Ile Thr Cys Arg Ala Ser Lys
            20                  25                  30

Thr Ile Ser Lys Tyr Leu Ala Trp Tyr Gln Gln Lys Pro Gly Lys Ala
        35                  40                  45

Pro Lys Leu Leu Ile Tyr Ser Gly Ser Thr Leu Gln Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Gln Gln His
                85                  90                  95

Asn Glu Tyr Pro Leu Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Leu Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 9
<211> LENGTH: 216
<212> TYPE: PRT
<213> ORGANISM: Artificial Sequence
<220> FEATURE:
<223> OTHER INFORMATION: ustekinumab light chain

<400> SEQUENCE: 9

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45
```

```
Tyr Ala Ala Ser Ser Leu Gln Ser Gly Val Pro Ser Arg Phe Ser Gly
         50                  55                  60
Ser Gly Ser Gly Thr Asp Phe Thr Leu Thr Ile Ser Ser Leu Gln Pro
 65              70                  75                      80
Glu Asp Phe Ala Thr Tyr Tyr Cys Gln Gln Tyr Asn Ile Tyr Pro Tyr
                 85                  90                  95
Thr Phe Gly Gln Gly Thr Lys Leu Glu Ile Lys Arg Thr Val Ala Ala
                100                 105                 110
Pro Ser Val Phe Ile Phe Pro Pro Ser Asp Glu Gln Leu Lys Ser Gly
            115                 120                 125
Thr Ala Ser Val Val Cys Leu Leu Asn Asn Phe Tyr Pro Arg Glu Ala
            130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Leu Tyr
            180                 185                 190
Ala Cys Glu Val Thr His Gln Gly Leu Ser Ser Pro Val Thr Lys Ser
            195                 200                 205
Phe Asn Arg Gly Glu Cys Leu Glu
        210                 215

<210> SEQ ID NO 10
<211> LENGTH: 15
<212> TYPE: PRT
<213> ORGANISM: Artificial Sequence
<220> FEATURE:
<223> OTHER INFORMATION: IgG1 hinge

<400> SEQUENCE: 10

Glu Pro Lys Ser Cys Asp Lys Thr His Thr Cys Pro Pro Cys Pro
 1               5                  10                  15

<210> SEQ ID NO 11
<211> LENGTH: 12
<212> TYPE: PRT
<213> ORGANISM: Artificial Sequence
<220> FEATURE:
<223> OTHER INFORMATION: IgG2 hinge

<400> SEQUENCE: 11

Glu Arg Lys Cys Cys Val Glu Cys Pro Pro Cys Pro
 1               5                  10

<210> SEQ ID NO 12
<211> LENGTH: 62
<212> TYPE: PRT
<213> ORGANISM: Artificial Sequence
<220> FEATURE:
<223> OTHER INFORMATION: IgG3 hinge

<400> SEQUENCE: 12

Glu Leu Lys Thr Pro Leu Gly Asp Thr Thr His Thr Cys Pro Arg Cys
 1               5                  10                  15
Pro Glu Pro Lys Ser Cys Asp Thr Pro Pro Cys Pro Arg Cys Pro
             20                  25                  30
Glu Pro Lys Ser Cys Asp Thr Pro Pro Cys Pro Arg Cys Pro Glu
             35                  40                  45
```

Pro Lys Ser Cys Asp Thr Pro Pro Cys Pro Arg Cys Pro
    50                  55                  60

<210> SEQ ID NO 13
<211> LENGTH: 12
<212> TYPE: PRT
<213> ORGANISM: Artificial Sequence
<220> FEATURE:
<223> OTHER INFORMATION: IgG4 hinge

<400> SEQUENCE: 13

Glu Ser Lys Tyr Gly Pro Pro Cys Pro Ser Cys Pro
1               5                   10

<210> SEQ ID NO 14
<211> LENGTH: 23
<212> TYPE: PRT
<213> ORGANISM: Artificial Sequence
<220> FEATURE:
<223> OTHER INFORMATION: IgA1 hinge

<400> SEQUENCE: 14

Pro Val Pro Ser Thr Pro Pro Thr Pro Ser Pro Ser Thr Pro Pro Thr
1               5                   10                  15

Pro Ser Pro Ser Cys Cys His
            20

<210> SEQ ID NO 15
<211> LENGTH: 10
<212> TYPE: PRT
<213> ORGANISM: Artificial Sequence
<220> FEATURE:
<223> OTHER INFORMATION: IgA2 hinge

<400> SEQUENCE: 15

Pro Val Pro Pro Pro Pro Pro Cys Cys His
1               5                   10

<210> SEQ ID NO 16
<211> LENGTH: 6
<212> TYPE: PRT
<213> ORGANISM: Artificial Sequence
<220> FEATURE:
<223> OTHER INFORMATION: MMP2 substrate

<400> SEQUENCE: 16

Gly Pro Leu Gly Val Arg
1               5

<210> SEQ ID NO 17
<211> LENGTH: 2445
<212> TYPE: DNA
<213> ORGANISM: Artificial Sequence
<220> FEATURE:
<223> OTHER INFORMATION: IgG1 Hinge Ipilimumab

<400> SEQUENCE: 17
gctagcaagc ttgttatcca ccatggagac agacacactc ctgctatggg tactgctgct      60
ctgggttcca ggttccactg gtgacgagcc caaatcttgt gacaaaactc acacatgccc     120
accgtgccca gttaacggcg gcggcggcag cggtccctg ggtgtgagag cggcccagcc     180
ggccgaaatt gtgttgacgc agtctccagg caccctgtct ttgtctccag gggaaagagc     240
caccctctcc tgcagggcca gtcagagtgt tggcagcagc tacttagcct ggtaccagca     300
gaaacctggc caggctccca ggctcctcat ctatggtgca ttcagcaggg ccactggcat     360

```
cccagacagg ttcagtggca gtgggtctgg gacagacttc actctcacca tcagcagact      420
ggagcctgaa gattttgcag tgtattactg tcagcagtat ggtagctcac cgtggacgtt      480
cggccaaggg accaaggtgg aaatcaaacg gactgtggct gcaccatctg tcttcatctt      540
cccgccatct gatgagcagt tgaaatctgg aactgcctct gttgtgtgcc tgctgaataa      600
cttctatccc agagaggcca agtacagtg gaaggtggat aacgccctcc aatcgggtaa      660
ctcccaggag agtgtcacag agcaggacag caaggacagc acctacagcc tcagcagcac      720
cctgacgctg agcaaagcag actacgagaa acacaaactc tacgcctgcg aagtcaccca      780
tcagggcctg agctcgcccg tcacaaagag cttcaacagg ggagagtgcc tcgagcgagc      840
aaaacgagca ccagtaaaac aaacactaaa cttcgaccta ctaaaactag caggagacgt      900
agaatcaaac ccaggaccag ccacaaccat ggagacagac acactcctgc tatgggtact      960
gctgctctgg gttccaggtt ccactggtga cgagcccaaa tcttgtgaca aaactcacac     1020
atgcccaccg tgcccaggcg ccgcggcg cggcggcagc ggtcccctgg gtgtgagaag     1080
atctcaggtg cagctggtgg agtctggggg aggcgtggtc cagcctggga ggtccctgag     1140
actctcctgt gcagcctctg gattcacctt cagtagctat actatgcact gggtccgcca     1200
ggctccaggc aaggggctgg agtgggtgac atttatatca tatgatggaa acaataaata     1260
ctacgcagac tccgtgaagg gccgattcac catctccaga gacaattcca gaacacgct     1320 gtatctgcaa atgaacagcc tgagagctga ggacacggct atatattact gtgcgaggac     1380
cggctggctg gggccctttg actactgggg ccagggaacc ctggtcaccg tctcctcagc     1440
ctccaccaag ggaccatcgg tcttcccct ggcaccctcc tccaagagca cctctggggg     1500
cacagcggcc ctgggctgcc tggtcaagga ctacttcccc gaaccggtga cggtgtcgtg     1560
gaactcaggc gccctgacca gcggcgtgca caccttcccg gctgtcctac agtcctcagg     1620
actctactcc ctcagcagcg tggtgaccgt gccctccagc agcttgggca cccagaccta     1680
catctgcaac gtgaatcaca agcccagcaa caccaaggtc gacaagaaag ttgagcccaa     1740
atcttgtgac aaaactcaca catgcccacc gtgcccagca cccgaactcc tggggggacc     1800
gtcagtcttc ctcttccccc caaaacccaa ggacaccctc atgatctccc ggaccctga     1860 ggtcacatgc gtggtggtgg acgtgagcca cgaagaccct gaggtcaagt tcaactggta     1920
cgtggacggc gtggaggtgc ataatgccaa gacaaagccg cgggaggagc agtacaacag     1980
cacgtaccgt gtggtcagcg tcctcaccgt cctgcaccag gactggctga atggcaagga     2040
gtacaagtgc aaggtctcca acaaagccct cccagccccc atcgagaaaa ccatctccaa     2100
agccaagggg cagccccgag aaccacaggt gtacaccctg cccccatccc gggatgagct     2160
gaccaagaac caggtcagcc tgacctgcct ggtcaaaggc ttctatccca gcgacatcgc     2220
cgtggagtgg gagagcaatg ggcagccgga gaacaactac aagaccacgc ctcccgtgct     2280
ggactccgac ggctccttct tcctctacag caagctcacc gtggacaaga gcaggtggca     2340
gcaggggaac gtcttctcat gctccgtgat gcatgaggct ctgcacaacc actacacgca     2400
gaagagcctc tccctgtctc cgggtaaata aatcgatggc gcgcc               2445
```

<210> SEQ ID NO 18
<211> LENGTH: 2427
<212> TYPE: DNA
<213> ORGANISM: Artificial Sequence
<220> FEATURE:
<223> OTHER INFORMATION: IgG2 Hinge Ipilimumab

```
<400> SEQUENCE: 18
gctagcaagc ttgttatcca ccatggagac agacacactc ctgctatggg tactgctgct      60
ctgggttcca ggttccactg gtgacgagcg caaatgttgt gtcgagtgcc accgtgccc      120
agttaacggc ggcggcggca gcggtcccct gggtgtgaga gcggcccagc cggccgaaat     180
tgtgttgacg cagtctccag gcaccctgtc tttgtctcca ggggaaagag ccaccctctc     240
ctgcagggcc agtcagagtg ttggcagcag ctacttagcc tggtaccagc agaaacctgg     300
ccaggctccc aggctcctca tctatggtgc attcagcagg gccactggca tcccagacag     360
gttcagtggc agtgggtctg ggacagactt cactctcacc atcagcagac tggagcctga     420
agattttgca gtgtattact gtcagcagta tggtagctca ccgtggacgt tcggccaagg     480
gaccaaggtg gaaatcaaac ggactgtggc tgcaccatct gtcttcatct tcccgccatc     540
tgatgagcag ttgaaatctg gaactgcctc tgttgtgtgc ctgctgaata acttctatcc     600
cagagaggcc aaagtacagt ggaaggtgga taacgccctc caatcgggta actcccagga     660
gagtgtcaca gagcaggaca gcaaggacag cacctacagc ctcagcagca ccctgacgct     720
gagcaaagca gactacgaga aacacaaact ctacgcctgc gaagtcaccc atcagggcct     780
gagctcgccc gtcacaaaga gcttcaacag gggagagtgc ctcgagcgag caaaacgagc     840
accagtaaaa caaacactaa acttcgacct actaaaacta gcaggagacg tagaatcaaa     900
cccaggacca gccacaacca tggagacaga cacactcctg ctatgggtac tgctgctctg     960
ggttccaggt tccactggtg acgagcgcaa atgttgtgtc gagtgccac cgtgcccagg     1020
cggccgcggc ggcggcggca gcggtcccct gggtgtgaga gatctcagg tgcagctggt    1080
ggagtctggg ggaggcgtgg tccagcctgg gaggtccctg agactctcct gtgcagcctc     1140
tggattcacc ttcagtagct atactatgca ctgggtccgc caggctccag gcaaggggct     1200
ggagtgggtg acatttatat catatgatgg aaacaataaa tactacgcag actccgtgaa    1260
gggccgattc accatctcca gagacaattc caagaacacg ctgtatctgc aaatgaacag     1320
cctgagagct gaggacacgg ctatatatta ctgtgcgagg accggctggc tggggccctt     1380
tgactactgg ggccagggaa ccctggtcac cgtctcctca gcctccacca agggaccatc     1440
ggtcttcccc ctggcaccct cctccaagag cacctctggg ggcacagcgg ccctgggctg     1500
cctggtcaag gactacttcc ccgaaccggt gacggtgtcg tggaactcag cgcccctgac     1560
cagcggcgtg cacaccttcc cggctgtcct acagtcctca ggactctact ccctcagcag     1620
cgtggtgacc gtgccctcca gcagcttggg cacccagacc tacatctgca acgtgaatca    1680
caagcccagc aacaccaagg tcgacaagaa agttgagccc aaatcttgtg acaaaactca    1740
cacatgccca ccgtgcccag cacccgaact cctgggggga ccgtcagtct tcctcttccc     1800
cccaaaaccc aaggacaccc tcatgatctc ccggaccccct gaggtcacat gcgtggtggt    1860
ggacgtgagc cacgaagacc ctgaggtcaa gttcaactgg tacgtggacg gcgtggaggt    1920
gcataatgcc aagacaaagc cgcgggagga gcagtacaac agcacgtacc gtgtggtcag    1980
cgtcctcacc gtcctgcacc aggactggct gaatggcaag gagtacaagt gcaaggtctc     2040
caacaaagcc ctcccagccc ccatcgagaa aaccatctcc aaagccaagg gcagccccg      2100
agaaccacag gtgtacaccc tgcccccatc ccgggatgag ctgaccaaga accaggtcag    2160
cctgacctgc ctggtcaaag gcttctatcc cagcgacatc gccgtggagt gggagagcaa    2220
tgggcagccg gagaacaact acaagaccac gcctcccgtg ctggactccg acggctcctt     2280
cttcctctac agcaagctca ccgtggacaa gagcaggtgg cagcagggga acgtcttctc    2340
```

```
atgctccgtg atgcatgagg ctctgcacaa ccactacacg cagaagagcc tctccctgtc    2400
tccgggtaaa taaatcgatg gcgcgcc                                        2427

<210> SEQ ID NO 19
<211> LENGTH: 2727
<212> TYPE: DNA
<213> ORGANISM: Artificial Sequence
<220> FEATURE:
<223> OTHER INFORMATION: IgG3 Hinge Ipilimumab

<400> SEQUENCE: 19
gctagcaagc ttgttatcca ccatggagac agacacactc ctgctatggg tactgctgct     60
ctgggttcca ggttccactg gtgacgagct caaaacccca cttggtgaca caactcacac    120
atgcccacgg tgcccagagc ccaaatcttg tgacacacct ccccgtgcc cacggtgccc     180 agagcccaaa tcttgtgaca cacctccccc atgcccacgg tgcccagagc ccaaatcttg    240
tgacacacct ccccgtgcc caaggtgccc agttaacggc ggcggcggca gcggtccct     300 gggtgtgaga gcggcccagc cggccgaaat tgtgttgacg cagtctccag gcaccctgtc    360
tttgtctcca ggggaaagag ccaccctctc ctgcagggcc agtcagagtg ttggcagcag    420
ctacttagcc tggtaccagc agaaacctgg ccaggctccc aggctcctca tctatggtgc    480
attcagcagg gccactggca tcccagacag gttcagtggc agtgggtctg ggacagactt    540
cactctcacc atcagcagac tggagcctga agattttgca gtgtattact gtcagcagta    600
tggtagctca ccgtggacgt tcggccaagg gaccaaggtg gaaatcaaac ggactgtggc    660
tgcaccatct gtcttcatct tcccgccatc tgatgagcag ttgaaatctg gaactgcctc    720
tgttgtgtgc ctgctgaata acttctatcc cagagaggcc aaagtacagt ggaaggtgga    780
taacgccctc caatcgggta actcccagga gagtgtcaca gagcaggaca gcaaggacag    840
cacctacagc ctcagcagca ccctgacgct gagcaaagca gactacgaga aacacaaact    900
ctacgcctgc gaagtcaccc atcagggcct gagctcgccc gtcacaaaga gcttcaacag    960
gggagagtgc ctcgagcgag caaaacgagc accagtaaaa caaacactaa acttcgacct   1020
actaaaacta gcaggagacg tagaatcaaa cccaggacca gccacaacca tggagacaga   1080
cacactcctg ctatgggtac tgctgctctg ggttccaggt tccactggtg acgagctcaa   1140
aaccccactt ggtgacacaa ctcacacatg cccacggtgc ccagagccca atcttgtga   1200 cacacctccc ccgtgcccac ggtgcccaga gcccaaatct tgtgacacac ctcccccatg   1260
cccacggtgc ccagagccca atcttgtga cacacctccc ccgtgcccaa ggtgcccagg   1320
cggccgcggc ggcggcggca gcggtccct gggtgtgaga agatctcagg tgcagctggt   1380
ggagtctggg ggaggcgtgg tccagcctgg gaggtccctg agactctcct gtgcagcctc   1440
tggattcacc ttcagtagct atactatgca ctgggtccgc caggctccag gcaaggggct   1500
ggagtgggtg acatttatat catatgatgg aaacaataaa tactacgcag actccgtgaa   1560
gggccgattc accatctcca gagacaattc caagaacacg ctgtatctgc aaatgaacag   1620
cctgagagct gaggacacgg ctatatatta ctgtgcgagg accggctggc tggggccctt   1680
tgactactgg ggccagggaa ccctggtcac cgtctcctca gcctccacca agggaccatc   1740
ggtcttcccc ctggcaccct cctccaagag cacctctggg ggcacagcgg ccctgggctg   1800
cctggtcaag gactacttcc ccgaaccggt gacggtgtcg tggaactcag cgccctgac   1860 cagcggcgtg cacaccttcc cggctgtcct acagtcctca ggactctact ccctcagcag   1920
```

```
cgtggtgacc gtgccctcca gcagcttggg cacccagacc tacatctgca acgtgaatca   1980
caagcccagc aacaccaagg tcgacaagaa agttgagccc aaatcttgtg acaaaactca   2040
cacatgccca ccgtgcccag cacccgaact cctggggggga ccgtcagtct tcctcttccc   2100
cccaaaaccc aaggacaccc tcatgatctc ccggacccct gaggtcacat gcgtggtggt   2160
ggacgtgagc cacgaagacc ctgaggtcaa gttcaactgg tacgtggacg gcgtggaggt   2220
gcataatgcc aagacaaagc cgcgggagga gcagtacaac agcacgtacc gtgtggtcag   2280
cgtcctcacc gtcctgcacc aggactggct gaatggcaag gagtacaagt gcaaggtctc   2340
caacaaagcc ctcccagccc ccatcgagaa aaccatctcc aaagccaagg gcagccccg    2400
agaaccacag gtgtacaccc tgcccccatc ccgggatgag ctgaccaaga accaggtcag   2460
cctgacctgc ctggtcaaag gcttctatcc cagcgacatc gccgtggagt gggagagcaa   2520
tgggcagccg gagaacaact acaagaccac gcctcccgtg ctggactccg acggctcctt   2580
cttcctctac agcaagctca ccgtggacaa gagcaggtgg cagcagggga acgtcttctc   2640
atgctccgtg atgcatgagg ctctgcacaa ccactacacg cagaagagcc tctccctgtc   2700
tccgggtaaa taaatcgatg gcgcgcc                                       2727

<210> SEQ ID NO 20
<211> LENGTH: 2427
<212> TYPE: DNA
<213> ORGANISM: Artificial Sequence
<220> FEATURE:
<223> OTHER INFORMATION: IgG4 Hinge Ipilimumab

<400> SEQUENCE: 20
gctagcaagc ttgttatcca ccatggagac agacacactc ctgctatggg tactgctgct     60
ctgggttcca ggttccactg gtgacgagtc caaatatggt cccccatgcc catcatgccc    120
agttaacggc ggcggcggca gcggtccccct gggtgtgaga gcggcccagc cggccgaaat    180
tgtgttgacg cagtctccag gcaccctgtc tttgtctcca ggggaaagag ccaccctctc    240
ctgcagggcc agtcagagtg ttggcagcag ctacttagcc tggtaccagc agaaacctgg    300
ccaggctccc aggctcctca tctatggtgc attcagcagg gccactggca tcccagacag    360
gttcagtggc agtgggtctg ggacagactt cactctcacc atcagcagac tggagcctga    420
agattttgca gtgtattact gtcagcagta tggtagctca ccgtgacgt tcggccaagg    480
gaccaaggtg gaaatcaaac ggactgtggc tgcaccatct gtcttcatct tcccgccatc    540
tgatgagcag ttgaaatctg gaactgcctc tgttgtgtgc ctgctgaata acttctatcc    600
cagagaggcc aaagtacagt ggaaggtgga taacgccctc caatcgggta actcccagga    660
gagtgtcaca gagcaggaca gcaaggacag cacctacagc ctcagcagca ccctgacgct    720
gagcaaagca gactacgaga aacacaaact ctacgcctgc gaagtcaccc atcagggcct    780
gagctcgccc gtcacaaaga gcttcaacag gggagagtgc tcgagcgag caaaacgagc    840
accagtaaaa caaacactaa acttcgacct actaaaacta gcaggagacg tagaatcaaa    900
cccaggacca gccacaacca tggagacaga cacactcctg ctatgggtac tgctgctctg    960
ggttccaggt tccactggtg acgagtccaa atatggtccc ccatgcccat catgcccagg   1020
cggccgcggc ggcggcggca gcggtccccct gggtgtgaga agatctcagg tgcagctggt   1080
ggagtctggg ggaggcgtgg tccagcctgg gaggtccctg agactctcct gtgcagcctc   1140
tggattcacc ttcagtagct atactatgca ctgggtccgc caggctccag gcaagggct    1200
ggagtgggtg acatttatat catatgatgg aaacaataaa tactacgcag actccgtgaa   1260
```

```
gggccgattc accatctcca gagacaattc caagaacacg ctgtatctgc aaatgaacag   1320
cctgagagct gaggacacgg ctatatatta ctgtgcgagg accggctggc tggggcccct   1380
tgactactgg ggccagggaa ccctggtcac cgtctcctca gcctccacca agggaccatc   1440
ggtcttcccc ctggcaccct cctccaagag cacctctggg ggcacagcgg ccctgggctg   1500
cctggtcaag gactacttcc ccgaaccggt gacggtgtcg tggaactcag gcgccctgac   1560
cagcggcgtg cacaccttcc cggctgtcct acagtcctca ggactctact ccctcagcag   1620
cgtggtgacc gtgccctcca gcagcttggg cacccagacc tacatctgca acgtgaatca   1680
caagcccagc aacaccaagg tcgacaagaa agttgagccc aaatcttgtg acaaaactca   1740
cacatgccca ccgtgcccag cacccgaact cctggggggga ccgtcagtct tcctcttccc   1800
cccaaaaccc aaggacaccc tcatgatctc ccggacccct gaggtcacat gcgtggtggt   1860
ggacgtgagc cacgaagacc ctgaggtcaa gttcaactgg tacgtggacg gcgtggaggt   1920
gcataatgcc aagacaaagc cgcgggagga gcagtacaac agcacgtacc gtgtggtcag   1980
cgtcctcacc gtcctgcacc aggactggct gaatggcaag gagtacaagt gcaaggtctc   2040
caacaaagcc ctcccagccc ccatcgagaa aaccatctcc aaagccaagg gcagccccccg   2100 agaaccacag gtgtacaccc tgcccccatc ccgggatgag ctgaccaaga accaggtcag   2160
cctgacctgc ctggtcaaag gcttctatcc cagcgacatc gccgtggagt gggagagcaa   2220
tgggcagccg gagaacaact acaagaccac gcctcccgtg ctggactccg acggctcctt   2280
cttcctctac agcaagctca ccgtggacaa gagcaggtgg cagcagggga acgtcttctc   2340
atgctccgtg atgcatgagg ctctgcacaa ccactacacg cagaagagcc tctccctgtc   2400
tccgggtaaa taaatcgatg gcgcgcc                                        2427

<210> SEQ ID NO 21
<211> LENGTH: 2469
<212> TYPE: DNA
<213> ORGANISM: Artificial Sequence
<220> FEATURE:
<223> OTHER INFORMATION: IgA1 Hinge Ipilimumab

<400> SEQUENCE: 21
gctagcaagc ttgttatcca ccatggagac agacacactc ctgctatggg tactgctgct    60
ctgggttcca ggttccactg gtgacccagt tccctcaact ccacctaccc catctccctc   120
aactccacct accccatctc cctcatgctg ccacgttaac ggcggcggcg gcagcggtcc   180
cctgggtgtg agagcggccc agccggccga aattgtgttg acgcagtctc caggcaccct   240
gtctttgtct ccaggggaaa gagccaccct ctcctgcagg gccagtcaga gtgttggcag   300
cagctactta gcctggtacc agcagaaacc tggccaggct cccaggctcc tcatctatgg   360
tgcattcagc agggccactg gcatcccaga caggttcagt ggcagtgggt ctgggacaga   420
cttcactctc accatcagca gactggagcc tgaagatttt gcagtgtatt actgtcagca   480
gtatggtagc tcaccgtgga cgttcggcca agggaccaag gtggaaatca aacggactgt   540
ggctgcacca tctgtcttca tcttcccgcc atctgatgag cagttgaaat ctggaactgc   600
ctctgttgtg tgcctgctga ataacttcta tcccagagag gccaaagtac agtggaaggt   660
ggataacgcc ctccaatcgg gtaactccca ggagagtgtc acagagcagg acagcaagga   720
cagcacctac agcctcagca gcaccctgac gctgagcaaa gcagactacg agaaacacaa   780
actctacgcc tgcgaagtca cccatcaggg cctgagctcg cccgtcacaa agagcttcaa   840
```

```
caggggagag tgcctcgagc gagcaaaacg agcaccagta aaacaaacac taaacttcga        900
cctactaaaa ctagcaggag acgtagaatc aaacccagga ccagccacaa ccatggagac        960
agacacactc ctgctatggg tactgctgct ctgggttcca ggttccactg gtgacgagcc       1020
caaatcttgt gacaaaactc acacatgccc accgtgccca gcggccgcg gcggcggcgg        1080 cagcggtccc ctgggtgtga agatctca ggtgcagctg gtggagtctg ggggaggcgt         1140
ggtccagcct gggaggtccc tgagactctc ctgtgcagcc tctggattca ccttcagtag        1200
ctatactatg cactgggtcc gccaggctcc aggcaagggg ctggagtggg tgacatttat        1260
atcatatgat ggaaacaata atactacgc agactccgtg aagggccgat tcaccatctc         1320
cagagacaat tccaagaaca cgctgtatct gcaaatgaac agcctgagag ctgaggacac        1380
ggctatatat tactgtgcga ggaccggctg gctggggccc tttgactact ggggccaggg        1440
aaccctggtc accgtctcct cagcctccac caagggacca tcggtcttcc ccctggcacc       1500
ctcctccaag agcacctctg ggggcacagc ggccctgggc tgcctggtca aggactactt       1560
ccccgaaccg gtgacggtgt cgtggaactc aggcgccctg accagcggcg tgcacacctt       1620
cccggctgtc ctacagtcct caggactcta ctccctcagc agcgtggtga ccgtgccctc       1680
cagcagcttg gcacccaga cctacatctg caacgtgaat cacaagccca gcaacaccaa        1740
ggtcgacaag aaagttgagc ccaaatcttg tgacaaaact cacacatgcc caccgtgccc       1800
agcacccgaa ctcctggggg gaccgtcagt cttcctcttc cccccaaaac ccaaggacac       1860
cctcatgatc tcccggaccc ctgaggtcac atgcgtggtg gtggacgtga gccacgaaga       1920
ccctgaggtc aagttcaact ggtacgtgga cggcgtggag gtgcataatg ccaagacaaa       1980
gccgcgggag gagcagtaca acagcacgta ccgtgtggtc agcgtcctca ccgtcctgca       2040
ccaggactgg ctgaatggca aggagtacaa gtgcaaggtc tccaacaaag ccctcccagc       2100
ccccatcgag aaaaccatct ccaaagccaa ggggcagccc cgagaaccac aggtgtacac       2160 cctgcccca tcccgggatg agctgaccaa gaaccaggtc agcctgacct gcctggtcaa       2220
aggcttctat cccagcgaca tcgccgtgga gtgggagagc aatgggcagc cggagaacaa       2280
ctacaagacc acgcctcccg tgctggactc cgacggctcc ttcttcctct acagcaagct       2340
caccgtggac aagagcaggt ggcagcaggg gaacgtcttc tcatgctccg tgatgcatga       2400
ggctctgcac aaccactaca cgcagaagag cctctccctg tctccgggta ataaatcga       2460 tggcgcgcc                                                              2469
```

<210> SEQ ID NO 22
<211> LENGTH: 2415
<212> TYPE: DNA
<213> ORGANISM: Artificial Sequence
<220> FEATURE:
<223> OTHER INFORMATION: IgA2 Hinge Ipilimumab

<400> SEQUENCE: 22

```
gctagcaagc ttgttatcca ccatggagac agacacactc ctgctatggg tactgctgct         60
ctgggttcca ggttccactg gtgacccagt tccccacct ccccatgct gccacgttaa         120 cggcggcggc ggcagcggtc cctgggtgt gagagcggcc cagccggccg aaattgtgtt         180
gacgcagtct ccaggcaccc tgtctttgtc tccaggggaa agagccaccc tctcctgcag         240
ggccagtcag agtgttggca gcagctactt agcctggtac cagcagaaac ctggccaggc         300
tcccaggctc ctcatctatg gtgcattcag cagggccact ggcatcccag acaggttcag         360
tggcagtggg tctgggacag acttcactct caccatcagc agactggagc ctgaagattt         420
```

```
tgcagtgtat tactgtcagc agtatggtag ctcaccgtgg acgttcggcc aagggaccaa      480
ggtggaaatc aaacggactg tggctgcacc atctgtcttc atcttcccgc catctgatga      540
gcagttgaaa tctggaactg cctctgttgt gtgcctgctg aataacttct atcccagaga      600
ggccaaagta cagtggaagg tggataacgc cctccaatcg ggtaactccc aggagagtgt      660
cacagagcag gacagcaagg acagcaccta cagcctcagc agcaccctga cgctgagcaa      720
agcagactac gagaaacaca aactctacgc ctgcgaagtc acccatcagg gcctgagctc      780
gcccgtcaca aagagcttca acaggggaga gtgcctcgag cgagcaaaac gagcaccagt      840
aaaacaaaca ctaaacttcg acctactaaa actagcagga gacgtagaat caaacccagg      900
accagccaca accatggaga cagacacact cctgctatgg gtactgctgc tctgggttcc      960
aggttccact ggtgacccag ttcccccacc tcccccatgc tgccacggcg gccgcggcgg     1020
cggcggcagc ggtcccctgg gtgtgagaag atctcaggtg cagctggtgg agtctggggg     1080
aggcgtggtc cagcctggga ggtccctgag actctcctgt gcagcctctg gattcacctt     1140
cagtagctat actatgcact gggtccgcca ggctccaggc aaggggctgg agtgggtgac     1200
atttatatca tatgatggaa acaataaata ctacgcagac tccgtgaagg gccgattcac     1260
catctccaga gacaattcca agaacacgct gtatctgcaa atgaacagcc tgagagctga     1320
ggacacggct atatattact gtgcgaggac cggctggctg gggccctttg actactgggg     1380
ccagggaacc ctggtcaccg tctcctcagc ctccaccaag ggaccatcgg tcttccccct     1440
ggcaccctcc tccaagagca cctctggggg cacagcggcc ctgggctgcc tggtcaagga     1500
ctacttcccc gaaccggtga cggtgtcgtg gaactcaggc gccctgacca gcggcgtgca     1560
caccttcccg gctgtcctac agtcctcagg actctactcc ctcagcagcg tggtgaccgt     1620
gccctccagc agcttgggca cccagaccta catctgcaac gtgaatcaca agcccagcaa     1680
caccaaggtc gacaagaaag ttgagcccaa atcttgtgac aaaactcaca catgcccacc     1740
gtgcccagca cccgaactcc tggggggacc gtcagtcttc ctcttccccc caaaacccaa     1800
ggacaccctc atgatctccc ggacccctga ggtcacatgc gtggtggtgg acgtgagcca     1860
cgaagaccct gaggtcaagt tcaactggta cgtggacggc gtggaggtgc ataatgccaa     1920
gacaaagccg cgggaggagc agtacaacag cacgtaccgt gtggtcagcg tcctcaccgt     1980
cctgcaccag gactggctga atggcaagga gtacaagtgc aaggtctcca acaaagccct     2040
cccagccccc atcgagaaaa ccatctccaa agccaagggg cagccccgag aaccacaggt     2100
gtacaccctg cccccatccc gggatgagct gaccaagaac caggtcagcc tgacctgcct     2160
ggtcaaaggc ttctatccca gcgacatcgc cgtggagtgg gagagcaatg ggcagccgga     2220
gaacaactac aagaccacgc ctcccgtgct ggactccgac ggctccttct tcctctacag     2280
caagctcacc gtggacaaga gcaggtggca gcagggaaac gtcttctcat gctccgtgat     2340
gcatgaggct ctgcacaacc actacacgca gaagagcctc tccctgtctc cgggtaaata     2400
aatcgatggc gcgcc                                                      2415
```

<210> SEQ ID NO 23
<211> LENGTH: 2451
<212> TYPE: DNA
<213> ORGANISM: Artificial Sequence
<220> FEATURE:
<223> OTHER INFORMATION: IgG1 Hinge Ticilimumab

<400> SEQUENCE: 23

```
gctagcaagc ttgttatcca ccatggagac agacacactc ctgctatggg tactgctgct    60
ctgggttcca ggttccactg gtgacgagcc caaatcttgt gacaaaactc acacatgccc   120
accgtgccca gttaacggcg gcggcggcag cggtcccctg ggtgtgagag cggcccagcc   180
ggccgacatc cagatgaccc agtctccatc ctccctgtct gcatctgtag agacagagt   240
caccatcact tgccgggcaa gtcagagcat taacagctat ttagattggt atcagcagaa   300
accagggaaa gcccctaagc tcctgatcta tgctgcatcc agtttgcaaa gtggggtccc   360
atcaaggttc agtggcagtg gatctgggac agatttcact ctcaccatca gcagtctgca   420
acctgaagat tttgcaactt actactgtca acagtattac agtaccccat tcactttcgg   480
ccctgggacc aaagtggaaa tcaaacgaac tgtggctgca ccatctgtct tcatcttccc   540
gccatctgat gagcagttga aatctggaac tgcctctgtt gtgtgcctgc tgaataactt   600
ctatcccaga gaggccaaag tacagtggaa ggtggataac gccctccaat cgggtaactc   660
ccaggagagt gtcacagagc aggacagcaa ggacagcacc tacagcctca gcagcaccct   720
gacgctgagc aaagcagact acgagaaaca caaactctac gcctgcgaag tcacccatca   780
gggcctgagc tcgcccgtca caaagagctt caacagggga gagtgcctcg agcgagcaaa   840
acgagcacca gtaaaacaaa cactaaactt cgacctacta aaactagcag agacgtaga   900
atcaaaccca ggaccagcca caaccatgga gacagacaca ctcctgctat gggtactgct   960
gctctgggtt ccaggttcca ctggtgacga gcccaaatct tgtgacaaaa ctcacacatg  1020
cccaccgtgc ccaggcggcc gcggcggcgg cggcagcggt ccctgggtg tgagaagatc  1080
tcaggtgcag ctggtggagt ctggggagg cgtggtccaa ccggggcggt ccctgagact  1140
ctcctgtgca gcctctggat tcaccttcag tagctatggc atgcactggg tccgccaggc  1200
tccagggaag gggctggagt gggtcgcagt tatttggtat gacggaagta acaaatatta  1260
tgcagactca gtgaagggcc gattcaccat ctccagagac aactccaaga acacactgta  1320
tctgcaaatg aacagcctga gccgaggac acggctgtg tattactgtg cgagagatcc  1380
tcgcggggca acactctact actactacta cgggatggac gtctggggcc agggaaccac  1440
ggtcaccgtc tcttcagcct ccaccaaggg cccatcggtc ttcccctgg cgccctgctc  1500
caggagcacc tccgagagca gcggccct gggctgcctg gtcaaggact acttccccga  1560
accggtgacg gtgtcgtgga actcaggcgc tctgaccagc ggcgtgcaca ccttcccagc  1620
tgtcctacag tcctcaggac tctactccct cagcagcgtg gtgaccgtgc cctccagcaa  1680
cttcggcacc cagacctaca cctgcaacgt agatcacaag cccagcaaca ccaaggtcga  1740
caagacagtt gagcgcaaat gttgtgtcga gtgcccaccg tgcccagcac cacctgtggc  1800
aggaccgtca gtcttcctct tccccccaaa acccaaggac accctcatga tctcccggac  1860
ccctgaggtc acgtgcgtgg tggtggacgt gagccacgaa gaccccgagg tccagttcaa  1920
ctggtacgtg gacggcgtgg aggtgcataa tgccaagaca aagccacggg aggagcagtt  1980
caacagcacg ttccgtgtgg tcagcgtcct caccgtcgtg caccaggact ggctgaacgg  2040
caaggagtac aagtgcaagg tctccaacaa aggcctccca gcccccatcg agaaaaccat  2100
ctccaaaacc aaagggcagc cccgagaacc acaggtgtac accctgcccc catcccggga  2160
ggagatgacc aagaaccagg tcagcctgac ctgcctggtc aaaggcttct accccagcga  2220
catcgccgtg gagtgggaga gcaatgggca gccggagaac aactacaaga ccacacctcc  2280
catgctggac tccgacggct ccttcttcct ctacagcaag ctcaccgtgg acaagagcag  2340
gtggcagcag gggaacgtct tctcatgctc cgtgatgcat gaggctctgc acaaccacta  2400
```

| | |
|---|---|
| cacacagaag agcctctccc tgtctccggg taaataaatc gatggcgcgc c | 2451 |

<210> SEQ ID NO 24
<211> LENGTH: 2433
<212> TYPE: DNA
<213> ORGANISM: Artificial Sequence
<220> FEATURE:
<223> OTHER INFORMATION: IgG2 Hinge Ticilimumab

<400> SEQUENCE: 24

| | |
|---|---|
| gctagcaagc ttgttatcca ccatggagac agacacactc ctgctatggg tactgctgct | 60 |
| ctgggttcca ggttccactg gtgacgagcg caaatgttgt gtcgagtgcc accgtgccc | 120 |
| agttaacggc ggcggcggca gcggtccccct gggtgtgaga gcggcccagc cggccgacat | 180 |
| ccagatgacc cagtctccat cctccctgtc tgcatctgta ggagacagag tcaccatcac | 240 |
| ttgccgggca agtcagagca ttaacagcta tttagattgg tatcagcaga accagggaa | 300 |
| agcccctaag ctcctgatct atgctgcatc cagtttgcaa agtggggtcc catcaaggtt | 360 |
| cagtggcagt ggatctggga cagatttcac tctcaccatc agcagtctgc aacctgaaga | 420 |
| ttttgcaact tactactgtc aacagtatta cagtacccca ttcactttcg gccctgggac | 480 |
| caaagtggaa atcaaacgaa ctgtggctgc accatctgtc ttcatcttcc cgccatctga | 540 |
| tgagcagttg aaatctggaa ctgcctctgt tgtgtgcctg ctgaataact tctatcccag | 600 |
| agaggccaaa gtacagtgga aggtggataa cgccctccaa tcgggtaact cccaggagag | 660 |
| tgtcacagag caggacagca aggacagcac ctacagcctc agcagcaccc tgacgctgag | 720 |
| caaagcagac tacgagaaac acaaactcta cgcctgcgaa gtcacccatc agggcctgag | 780 |
| ctcgcccgtc acaaagagct tcaacagggg agagtgcctc gagcgagcaa acgagcacc | 840 |
| agtaaaacaa acactaaact tcgacctact aaaactagca ggagacgtag aatcaaaccc | 900 |
| aggaccagcc acaaccatgg agacagacac tcctgcta tgggtactgc tgctctgggt | 960 |
| tccaggttcc actggtgacg agcgcaaatg ttgtgtcgag tgcccaccgt gcccaggcgg | 1020 |
| ccgcggcggc ggcggcagcg gtcccctggg tgtgagaaga tctcaggtgc agctggtgga | 1080 |
| gtctggggga ggcgtggtcc aaccggggcg gtccctgaga ctctcctgtg cagcctctgg | 1140 |
| attcaccttc agtagctatg catgcactg gtccgccag gctccaggga aggggctgga | 1200 |
| gtgggtcgca gttatttggt atgacggaag taacaaatat tatgcagact cagtgaaggg | 1260 |
| ccgattcacc atctccagag acaactccaa gaacacactg tatctgcaaa tgaacagcct | 1320 |
| gagagccgag gacacggctg tgtattactg tgcgagagat cctcgcgggg caacactcta | 1380 |
| ctactactac tacgggatgg acgtctgggg ccagggaacc acggtcaccg tctcttcagc | 1440 |
| ctccaccaag ggcccatcgg tcttccccct ggcgccctgc tccaggagca cctccgagag | 1500 |
| cacagcggcc ctgggctgcc tggtcaagga ctacttcccc gaaccggtga cggtgtcgtg | 1560 |
| gaactcaggc gctctgacca gcggcgtgca caccttccca gctgtcctac agtcctcagg | 1620 |
| actctactcc ctcagcagcg tggtgaccgt gccctccagc aacttcggca cccagaccta | 1680 |
| cacctgcaac gtagatcaca agcccagcaa caccaaggtc gacaagacag ttgagcgcaa | 1740 |
| atgttgtgtc gagtgcccac cgtgcccagc caccctgtg caggaccgt cagtcttcct | 1800 |
| cttccccca aaacccaagg acaccctcat gatctcccgg acccctgagg tcacgtgcgt | 1860 |
| ggtggtggac gtgagccacg aagaccccga ggtccagttc aactggtacg tggacggcgt | 1920 |
| ggaggtgcat aatgccaaga caaagccacg ggaggagcag ttcaacagca cgttccgtgt | 1980 |

```
ggtcagcgtc ctcaccgtcg tgcaccagga ctggctgaac ggcaaggagt acaagtgcaa    2040
ggtctccaac aaaggcctcc cagcccccat cgagaaaacc atctccaaaa ccaaagggca    2100
gccccgagaa ccacaggtgt acaccctgcc cccatcccgg gaggagatga ccaagaacca    2160
ggtcagcctg acctgcctgg tcaaaggctt ctaccccagc gacatcgccg tggagtggga    2220
gagcaatggg cagccggaga caactacaa gaccacacct cccatgctgg actccgacgg    2280
ctccttcttc ctctacagca agctcaccgt ggacaagagc aggtggcagc aggggaacgt    2340
cttctcatgc tccgtgatgc atgaggctct gcacaaccac tacacacaga gagcctctc    2400 cctgtctccg ggtaaataaa tcgatggcgc gcc                                 2433

<210> SEQ ID NO 25
<211> LENGTH: 2733
<212> TYPE: DNA
<213> ORGANISM: Artificial Sequence
<220> FEATURE:
<223> OTHER INFORMATION: IgG3 Hinge Ticilimumab

<400> SEQUENCE: 25
gctagcaagc ttgttatcca ccatggagac agacacactc ctgctatggg tactgctgct      60
ctgggttcca ggttccactg gtgacagct caaaacccca cttggtgaca caactcacac     120
atgcccacgg tgcccagagc ccaaatcttg tgacacacct ccccgtgcc acggtgccc     180 agagcccaaa tcttgtgaca cacctccccc atgcccacgg tgcccagagc ccaaatcttg     240
tgacacacct ccccgtgcc aaggtgccca gttaacggc ggcggcggca gcggtcccct     300
gggtgtgaga gcggcccagc cggccgacat ccagatgacc cagtctccat cctcctgtc    360 tgcatctgta ggagacagag tcaccatcac ttgccgggca agtcagagca ttaacagcta     420
tttagattgg tatcagcaga accagggaa agcccctaag ctcctgatct atgctgcatc     480
cagtttgcaa agtggggtcc catcaaggtt cagtggcagt ggatctggga cagatttcac     540
tctcaccatc agcagtctgc aacctgaaga ttttgcaact tactactgtc aacagtatta     600
cagtacccca ttcactttcg ccctgggac caaagtggaa atcaaacgaa ctgtggctgc     660 accatcgtc ttcatcttcc cgccatctga tgagcagttg aaatctggaa ctgcctctgt     720
tgtgtgcctg ctgaataact ctatcccag agaggccaaa gtacagtgga aggtggataa     780
cgccctccaa tcgggtaact cccaggagag tgtcacagag caggacagca aggacagcac     840
ctacagcctc agcagcaccc tgacgctgag caaagcagac tacgagaaac acaaactcta    900
cgcctgcgaa gtcacccatc agggcctgag ctcgcccgtc acaaagagct tcaacagggg     960
agagtgcctc gagcgagcaa acgagcacc agtaaaacaa acactaaact tcgacctact    1020
aaaactagca ggagacgtag aatcaaaccc aggaccagcc acaaccatgg agacagacac    1080
actcctgcta tgggtactgc tgctctgggt tccaggttcc actggtgacg agctcaaaac    1140
cccacttggt gacacaactc acacatgccc acgtgccca gagcccaaat cttgtgacac    1200 acctccccg tgcccacggt gcccagagcc caaatcttgt gacacacctc cccatgccc    1260 acggtgccca gagcccaaat cttgtgacac acctccccg tgcccaaggt gcccaggcgg    1320
ccgcggcggc ggcggcagcg gtcccctggg tgtgagaaga tctcaggtgc agctggtgga    1380
gtctggggga ggcgtggtcc aaccggggcg gtccctgaga ctctcctgtg cagcctctgg    1440
attcaccttc agtagctatg gcatgcactg ggtccgccag gctccaggga aggggctgga    1500
gtgggtcgca gttatttggt atgacggaag taacaaatat tatgcagact cagtgaaggg    1560
ccgattcacc atctccagag acaactccaa gaacacactg tatctgcaaa tgaacagcct    1620
```

```
gagagccgag gacacggctg tgtattactg tgcgagagat cctcgcgggg caacactcta    1680
ctactactac tacgggatgg acgtctgggg ccagggaacc acggtcaccg tctcttcagc    1740
ctccaccaag ggcccatcgg tcttccccct ggcgccctgc tccaggagca cctccgagag    1800
cacagcggcc ctgggctgcc tggtcaagga ctacttcccc gaaccggtga cggtgtcgtg    1860
gaactcaggc gctctgacca gcggcgtgca ccttccca gctgtcctac agtcctcagg    1920
actctactcc ctcagcagcg tggtgaccgt gccctccagc aacttcggca cccagaccta    1980
cacctgcaac gtagatcaca agcccagcaa caccaaggtc gacaagacag ttgagcgcaa    2040
atgttgtgtc gagtgcccac cgtgcccagc accacctgtg gcaggaccgt cagtcttcct    2100 cttccccca aaacccaagg acaccctcat gatctcccgg acccctgagg tcacgtgcgt    2160
ggtggtggac gtgagccacg aagaccccga ggtccagttc aactggtacg tggacggcgt    2220
ggaggtgcat aatgccaaga caaagccacg ggaggagcag ttcaacagca cgttccgtgt    2280
ggtcagcgtc ctcaccgtcg tgcaccagga ctggctgaac ggcaaggagt acaagtgcaa    2340
ggtctccaac aaaggcctcc cagcccccat cgagaaaacc atctccaaaa ccaaagggca    2400
gccccgagaa ccacaggtgt acaccctgcc cccatcccgg gaggagatga ccaagaacca    2460
ggtcagcctg acctgcctgg tcaaaggctt ctaccccagc gacatcgccg tggagtggga    2520
gagcaatggg cagccggaga acaactacaa gaccacacct cccatgctgg actccgacgg    2580
ctccttcttc ctctacagca agctcaccgt ggacaagagc aggtggcagc aggggaacgt    2640
cttctcatgc tccgtgatgc atgaggctct gcacaaccac tacacacaga gagcctctc    2700 cctgtctccg ggtaaataaa tcgatggcgc gcc                                  2733

<210> SEQ ID NO 26
<211> LENGTH: 2433
<212> TYPE: DNA
<213> ORGANISM: Artificial Sequence
<220> FEATURE:
<223> OTHER INFORMATION: IgG4 Hinge Ticilimumab

<400> SEQUENCE: 26
gctagcaagc ttgttatcca ccatggagac agacacactc ctgctatggg tactgctgct      60
ctgggttcca ggttccactg gtgacgagtc caaatatggt cccccatgcc catcatgccc     120
agttaacggc ggcggcggca gcggtcccct gggtgtgaga gcggcccagc cggccgacat     180
ccagatgacc cagtctccat cctccctgtc tgcatctgta ggagacagag tcaccatcac     240
ttgccgggca agtcagagca ttaacagcta tttagattgg tatcagcaga accaggga     300 agcccctaag ctcctgatct atgctgcatc cagtttgcaa agtggggtcc catcaaggtt     360
cagtggcagt ggatctggga cagatttcac tctcaccatc agcagtctgc aacctgaaga     420
ttttgcaact tactactgtc aacagtatta cagtacccca ttcactttcg gccctgggac     480
caaagtggaa atcaaacgaa ctgtggctgc accatctgtc ttcatcttcc cgccatctga     540
tgagcagttg aaatctggaa ctgcctctgt tgtgtgcctg ctgaataact tctatcccag     600
agaggccaaa gtacagtgga aggtggataa cgccctccaa tcgggtaact cccaggagag     660
tgtcacagag caggacagca aggacagcac ctacagcctc agcagcaccc tgacgctgag     720
caaagcagac tacgagaaac acaaactcta cgcctgcgaa gtcacccatc agggcctgag     780
ctcgcccgtc acaaagagct tcaacagggg agagtgcctc gagcgagcaa acgagcacc     840 agtaaaacaa acactaaact tcgacctact aaaactagca ggagacgtag aatcaaaccc     900
```

|  |  |  |  |  |
|---|---|---|---|---|
| aggaccagcc | acaaccatgg | agacagacac | actcctgcta tgggtactgc tgctctgggt | 960 |
| tccaggttcc | actggtgacg | agtccaaata | tggtccccca tgcccatcat gcccaggcgg | 1020 |
| ccgcggcggc | ggcggcagcg | gtcccctggg | tgtgagaaga tctcaggtgc agctggtgga | 1080 |
| gtctggggga | ggcgtggtcc | aaccggggcg | gtccctgaga ctctcctgtg cagcctctgg | 1140 |
| attcaccttc | agtagctatg | catgcactg | ggtccgccag gctccaggga aggggctgga | 1200 |
| gtgggtcgca | gttatttggt | atgacggaag | taacaaatat tatgcagact cagtgaaggg | 1260 |
| ccgattcacc | atctccagag | acaactccaa | gaacacactg tatctgcaaa tgaacagcct | 1320 |
| gagagccgag | gacacggctg | tgtattactg | tgcgagagat cctcgcgggg caacactcta | 1380 |
| ctactactac | tacgggatgg | acgtctgggg | ccagggaacc acggtcaccg tctcttcagc | 1440 |
| ctccaccaag | ggcccatcgg | tcttccccct | ggcgccctgc tccaggagca cctccgagag | 1500 |
| cacagcggcc | ctgggctgcc | tggtcaagga | ctacttcccc gaaccggtga cggtgtcgtg | 1560 |
| gaactcaggc | gctctgacca | gcggcgtgca | caccttccca gctgtcctac agtcctcagg | 1620 |
| actctactcc | ctcagcagcg | tggtgaccgt | gccctccagc aacttcggca cccagaccta | 1680 |
| cacctgcaac | gtagatcaca | agcccagcaa | caccaaggtc gacaagacag ttgagcgcaa | 1740 |
| atgttgtgtc | gagtgcccac | cgtgcccagc | accacctgtg gcaggaccgt cagtcttcct | 1800 |
| cttcccccca | aaacccaagg | acaccctcat | gatctcccgg acccctgagg tcacgtgcgt | 1860 |
| ggtggtggac | gtgagccacg | aagaccccga | ggtccagttc aactggtacg tggacggcgt | 1920 |
| ggaggtgcat | aatgccaaga | caaagccacg | ggaggagcag ttcaacagca cgttccgtgt | 1980 |
| ggtcagcgtc | ctcaccgtcg | tgcaccagga | ctggctgaac ggcaaggagt acaagtgcaa | 2040 |
| ggtctccaac | aaaggcctcc | cagcccccat | cgagaaaacc atctccaaaa ccaaagggca | 2100 |
| gccccgagaa | ccacaggtgt | acaccctgcc | cccatcccgg gaggagatga ccaagaacca | 2160 |
| ggtcagcctg | acctgcctgg | tcaaaggctt | ctaccccagc gacatcgccg tggagtggga | 2220 |
| gagcaatggg | cagccggaga | acaactacaa | gaccacacct cccatgctgg actccgacgg | 2280 |
| ctccttcttc | ctctacagca | agctcaccgt | ggacaagagc aggtggcagc aggggaacgt | 2340 |
| cttctcatgc | tccgtgatgc | atgaggctct | gcacaaccac tacacacaga gagcctctc | 2400 |
| cctgtctccg | ggtaaataaa | tcgatggcgc | gcc | 2433 |

<210> SEQ ID NO 27
<211> LENGTH: 2475
<212> TYPE: DNA
<213> ORGANISM: Artificial Sequence
<220> FEATURE:
<223> OTHER INFORMATION: IgA1 Hinge Ticilimumab

<400> SEQUENCE: 27

|  |  |  |  |  |
|---|---|---|---|---|
| gctagcaagc | ttgttatcca | ccatggagac | agacacactc ctgctatggg tactgctgct | 60 |
| ctgggttcca | ggttccactg | gtgacccagt | tccctcaact ccacctaccc catctccctc | 120 |
| aactccacct | accccatctc | cctcatgctg | ccacgttaac ggcggcggcg gcagcggtcc | 180 |
| cctgggtgtg | agagcggccc | agccggccga | catccagatg acccagtctc catcctccct | 240 |
| gtctgcatct | gtaggagaca | gagtcaccat | cacttgccgg gcaagtcaga gcattaacag | 300 |
| ctatttagat | tggtatcagc | agaaaccagg | gaaagcccct aagctcctga tctatgctgc | 360 |
| atccagtttg | caaagtgggg | tcccatcaag | gttcagtggc agtggatctg ggacagattt | 420 |
| cactctcacc | atcagcagtc | tgcaacctga | agattttgca acttactact gtcaacagta | 480 |
| ttacagtacc | ccattcactt | tcggccctgg | gaccaaagtg gaaatcaaac gaactgtggc | 540 |

```
tgcaccatct gtcttcatct tcccgccatc tgatgagcag ttgaaatctg gaactgcctc      600
tgttgtgtgc ctgctgaata acttctatcc cagagaggcc aaagtacagt ggaaggtgga      660
taacgccctc caatcgggta actcccagga gagtgtcaca gagcaggaca gcaaggacag      720
cacctacagc ctcagcagca ccctgacgct gagcaaagca gactacgaga aacacaaact      780
ctacgcctgc gaagtcaccc atcagggcct gagctcgccc gtcacaaaga gcttcaacag      840
gggagagtgc ctcgagcgag caaaacgagc accagtaaaa caaacactaa acttcgacct      900
actaaaacta gcaggagacg tagaatcaaa cccaggacca gccacaacca tggagacaga      960
cacactcctg ctatgggtac tgctgctctg ggttccaggt tccactggtg acgagcccaa     1020
atcttgtgac aaaactcaca catgcccacc gtgcccaggc ggccgcggcg cggcggcag      1080 cggtccctg ggtgtgagaa gatctcaggt gcagctggtg gagtctgggg gaggcgtggt     1140
ccaaccgggg cggtccctga gactctcctg tgcagcctct ggattcacct tcagtagcta     1200
tggcatgcac tgggtccgcc aggctccagg gaaggggctg gagtgggtcg cagttatttg     1260
gtatgacgga agtaacaaat attatgcaga ctcagtgaag ggccgattca ccatctccag     1320
agacaactcc aagaacacac tgtatctgca aatgaacagc ctgagagccg aggacacggc     1380
tgtgtattac tgtgcgagag atcctcgcgg ggcaacactc tactactact actacgggat     1440
ggacgtctgg ggccagggaa ccacggtcac cgtctcttca gcctccacca gggcccatc      1500 ggtcttcccc ctggcgccct gctccaggag cacctccgag agcacagcgg ccctgggctg     1560
cctggtcaag gactacttcc ccgaaccggt gacggtgtcg tggaactcag cgctctgac      1620 cagcggcgtg cacaccttcc cagctgtcct acagtcctca ggactctact ccctcagcag     1680
cgtggtgacc gtgccctcca gcaacttcgg cacccagacc tacacctgca acgtagatca     1740
caagcccagc aacaccaagg tcgacaagac agttgagcgc aaatgttgtg tcgagtgccc     1800
accgtgccca gcaccacctg tggcaggacc gtcagtcttc ctcttccccc caaaacccaa     1860
ggacaccctc atgatctccc ggaccctga ggtcacgtgc gtggtggtgg acgtgagcca      1920
cgaagacccc gaggtccagt tcaactggta cgtggacggc gtggaggtgc ataatgccaa     1980
gacaaagcca cgggaggagc agttcaacag cacgttccgt gtggtcagcg tcctcaccgt     2040
cgtgcaccag gactggctga acggcaagga gtacaagtgc aaggtctcca acaaaggcct     2100
cccagccccc atcgagaaaa ccatctccaa aaccaaaggg cagccccgag aaccacaggt     2160
gtacaccctg cccccatccc gggaggagat gaccaagaac caggtcagcc tgacctgcct     2220
ggtcaaaggc ttctacccca gcgacatcgc cgtggagtgg gagagcaatg ggcagccgga     2280
gaacaactac aagaccacac ctcccatgct ggactccgac ggctccttct cctctacag      2340 caagctcacc gtggacaaga gcaggtggca gcagggaaac gtcttctcat gctccgtgat     2400
gcatgaggct ctgcacaacc actacacaca gaagagcctc tccctgtctc cgggtaaata     2460
aatcgatggc gcgcc                                                      2475
```

<210> SEQ ID NO 28
<211> LENGTH: 2421
<212> TYPE: DNA
<213> ORGANISM: Artificial Sequence
<220> FEATURE:
<223> OTHER INFORMATION: IgA2 Hinge Ticilimumab

<400> SEQUENCE: 28

```
gctagcaagc ttgttatcca ccatggagac agacacactc ctgctatggg tactgctgct       60
```

```
ctgggttcca ggttccactg gtgacccagt tcccccacct cccccatgct gccacgttaa    120
cggcggcggc ggcagcggtc ccctgggtgt gagagcggcc cagccggccg acatccagat    180
gacccagtct ccatcctccc tgtctgcatc tgtaggagac agagtcacca tcacttgccg    240
ggcaagtcag agcattaaca gctatttaga ttggtatcag cagaaaccag ggaaagcccc    300
taagctcctg atctatgctg catccagttt gcaaagtggg gtcccatcaa ggttcagtgg    360
cagtggatct gggacagatt tcactctcac catcagcagt ctgcaacctg aagattttgc    420
aacttactac tgtcaacagt attacagtac cccattcact ttcggccctg ggaccaaagt    480
ggaaatcaaa cgaactgtgg ctgcaccatc tgtcttcatc ttcccgccat ctgatgagca    540
gttgaaatct ggaactgcct ctgttgtgtg cctgctgaat aacttctatc ccagagaggc    600
caaagtacag tggaaggtgg ataacgccct ccaatcgggt aactcccagg agagtgtcac    660
agagcaggac agcaaggaca gcacctacag cctcagcagc accctgacgc tgagcaaagc    720
agactacgag aaacacaaac tctacgcctg cgaagtcacc catcagggcc tgagctcgcc    780
cgtcacaaag agcttcaaca ggggagagtg cctcgagcga gcaaaacgag caccagtaaa    840
acaaacacta aacttcgacc tactaaaact agcaggagac gtagaatcaa acccaggacc    900
agccacaacc atggagacag acacactcct gctatgggta ctgctgctct gggttccagg    960
ttccactggt gacccagttc ccccacctcc ccatgctgc cacggcggcc gcggcggcgg   1020
cggcagcggt ccctgggtgt gagaagatc tcaggtgcag ctggtggagt ctggggagg   1080 cgtggtccaa ccggggcggt ccctgagact ctcctgtgca gcctctggat tcaccttcag   1140
tagctatggc atgcactggg tccgccaggc tccaggaag gggctggagt gggtcgcagt   1200
tatttggtat gacggaagta acaaatatta tgcagactca gtgaagggcc gattcaccat   1260
ctccagagac aactccaaga acacactgta tctgcaaatg aacagcctga gagccgagga   1320
cacggctgtg tattactgtg cgagagatcc tcgcggggca acactctact actactacta   1380
cgggatggac gtctggggcc agggaaccac ggtcaccgtc tcttcagcct ccaccaaggg   1440
cccatcggtc ttccccctgg cgccctgctc caggagcacc tccgagagca gcggccct   1500 gggctgcctg gtcaaggact acttccccga accggtgacg gtgtcgtgga actcaggcgc   1560
tctgaccagc ggcgtgcaca ccttcccagc tgtcctacag tcctcaggac tctactccct   1620
cagcagcgtg gtgaccgtgc cctccagcaa cttcggcacc cagacctaca cctgcaacgt   1680
agatcacaag cccagcaaca ccaaggtcga caagacagtt gagcgcaaat gttgtgtcga   1740
gtgcccaccg tgcccagcac cacctgtggc aggaccgtca gtcttcctct tccccccaaa   1800
acccaaggac accctcatga tctcccggac ccctgaggtc acgtgcgtgg tggtggacgt   1860
gagccacgaa gaccccgagg tccagttcaa ctggtacgtg gacggcgtgg aggtgcataa   1920
tgccaagaca aagccacggg aggagcagtt caacagcacg ttccgtgtgg tcagcgtcct   1980
caccgtcgtg caccaggact ggctgaacgg caaggagtac aagtgcaagg tctccaacaa   2040
aggcctccca gcccccatcg agaaaaccat ctccaaaacc aaagggcagc cccgagaacc   2100
acaggtgtac accctgcccc catcccggga ggagatgacc aagaaccagg tcagcctgac   2160
ctgcctggtc aaaggcttct accccagcga catcgccgtg gagtgggaga gcaatgggca   2220
gccggagaac aactacaaga ccacacctcc catgctggac tccgacggct ccttcttcct   2280
ctacagcaag ctcaccgtgg acaagagcag gtggcagcag gggaacgtct tctcatgctc   2340
cgtgatgcat gaggctctgc acaaccacta cacacagaag agcctctccc tgtctccggg   2400
taaataaatc gatggcgcgc c                                             2421
```

<210> SEQ ID NO 29
<211> LENGTH: 2451
<212> TYPE: DNA
<213> ORGANISM: Artificial Sequence
<220> FEATURE:
<223> OTHER INFORMATION: IgG1 Hinge Humira

<400> SEQUENCE: 29

| | | | | | |
|---|---|---|---|---|---|
| gctagcaagc | ttgttatcca | ccatggagac | agacacactc | ctgctatggg | tactgctgct | 60 |
| ctgggttcca | ggttccactg | gtgacgagcc | caaatcttgt | gacaaaactc | acacatgccc | 120 |
| accgtgccca | gttaacggcg | gcggcggcag | cggtcccctg | gtgtgagag | cggcccagcc | 180 |
| ggccgacatc | cagatgaccc | agagccccag | cagcctgagc | gccagcgtgg | gcgacagagt | 240 |
| gaccatcacc | tgcagagcca | gcagggcat | cagaaactac | ctggcctggt | accagcagaa | 300 |
| gcccggcaag | gcccccaagc | tgctgatcta | cgccgccagc | accctgcaga | gcggcgtgcc | 360 |
| cagcagattc | agcggcagcg | gcagcggcac | cgacttcacc | ctgaccatca | gcagcctgca | 420 |
| gcccgaggac | gtggccacct | actactgcca | gagatacaac | agagcccct | acaccttcgg | 480 |
| ccagggcacc | aaggtggaga | tcaagagaac | tgtggctgca | ccatctgtct | tcatcttccc | 540 |
| gccatctgat | gagcagttga | aatctggaac | tgcctctgtt | gtgtgcctgc | tgaataactt | 600 |
| ctatcccaga | gaggccaaag | tacagtggaa | ggtggataac | gccctccaat | cgggtaactc | 660 |
| ccaggagagt | gtcacagagc | aggacagcaa | ggacagcacc | tacagcctca | gcagcaccct | 720 |
| gacgctgagc | aaagcagact | acgagaaaca | caaactctac | gcctgcgaag | tcacccatca | 780 |
| gggcctgagc | tcgcccgtca | caaagagctt | caacagggga | gagtgcctcg | agcgagcaaa | 840 |
| acgagcacca | gtaaaacaaa | cactaaactt | cgacctacta | aaactagcag | agacgtaga | 900 |
| atcaaaccca | ggaccagcca | caaccatgga | gacagacaca | ctcctgctat | gggtactgct | 960 |
| gctctgggtt | ccaggttcca | ctggtgacga | gcccaaatct | tgtgacaaaa | ctcacacatg | 1020 |
| cccaccgtgc | ccaggcggcc | gcggcggcgg | cggcagcggt | cccctgggtg | tgagaagatc | 1080 |
| tgaggtgcag | ctggtggaga | gcggcggcgg | cctggtgcag | cccggcagaa | gcctgagact | 1140 |
| gagctgcgcc | gccagcggct | tcaccttcga | cgactacgcc | atgcactggg | tgagacaggc | 1200 |
| ccccggcaag | ggcctggagt | gggtgagcgc | catcacctgg | aacagcggcc | acatcgacta | 1260 |
| cgccgacagc | gtggagggca | gattcaccat | cagcagagac | aacgccaaga | acagcctgta | 1320 |
| cctgcagatg | aacagcctga | gaccgagga | caccgccgtg | tactactgcg | ccaaggtgag | 1380 |
| ctacctgagc | accgccagca | gcctggacta | ctggggccag | gcaccctgg | tgaccgtgag | 1440 |
| cagcgcctcc | accaagggac | catcggtctt | ccccctggca | ccctcctcca | agagcacctc | 1500 |
| tgggggcaca | gcgccctggg | ctgcctggt | caaggactac | ttccccgaac | cggtgacggt | 1560 |
| gtcgtggaac | tcaggcgccc | tgaccagcgg | cgtgcacacc | ttcccggctg | tcctacagtc | 1620 |
| ctcaggactc | tactccctca | gcagcgtggt | gaccgtgccc | tccagcagct | tgggcaccca | 1680 |
| gacctacatc | tgcaacgtga | atcacaagcc | cagcaacacc | aaggtcgaca | agaaagttga | 1740 |
| gcccaaatct | tgtgacaaaa | ctcacacatg | cccaccgtgc | ccagcacctg | aactcctggg | 1800 |
| gggaccgtca | gtcttcctct | tccccccaaa | acccaaggac | accctcatga | tctcccggac | 1860 |
| ccctgaggtc | acatgcgtgg | tggtggacgt | gagccacgaa | gaccctgagg | tcaagttcaa | 1920 |
| ctggtacgtg | gacggcgtgg | aggtgcataa | tgccaagaca | aagccgcggg | aggagcagta | 1980 |
| caacagcacg | taccgggtgg | tcagcgtcct | caccgtcctg | caccaggact | ggctgaatgg | 2040 |

| | |
|---|---|
| caaggagtac aagtgcaagg tctccaacaa agccctccca gccccatcg agaaaaccat | 2100 |
| ctccaaagcc aaagggcagc cccgagaacc acaggtgtac accctgcccc catcccggga | 2160 |
| tgagctgacc aagaaccagg tcagcctgac ctgcctggtc aaaggcttct atcccagcga | 2220 |
| catcgccgtg gagtgggaga gcaatgggca gccggagaac aactacaaga ccacgcctcc | 2280 |
| cgtgctggac tccgacggct ccttcttcct ctacagcaag ctcaccgtgg acaagagcag | 2340 |
| gtggcagcag gggaacgtct tctcatgctc cgtgatgcat gaggctctgc acaaccacta | 2400 |
| cacgcagaag agcctctccc tgtctccggg taaataaatc gatggcgcgc c | 2451 |

<210> SEQ ID NO 30
<211> LENGTH: 2433
<212> TYPE: DNA
<213> ORGANISM: Artificial Sequence
<220> FEATURE:
<223> OTHER INFORMATION: IgG2 Hinge Humira

<400> SEQUENCE: 30

| | |
|---|---|
| gctagcaagc ttgttatcca ccatggagac agacacactc ctgctatggg tactgctgct | 60 |
| ctgggttcca ggttccactg gtgacgagcg caaatgttgt gtcgagtgcc accgtgccc | 120 |
| agttaacggc ggcggcggca gcggtcccct gggtgtgaga gcggcccagc cggccgacat | 180 |
| ccagatgacc cagagcccca gcagcctgag cgccagcgtg ggcgacagag tgaccatcac | 240 |
| ctgcagagcc agccagggca tcagaaacta cctggcctgg taccagcaga agcccggcaa | 300 |
| ggccccccaag ctgctgatct acgccgccag caccctgcag agcggcgtgc ccagcagatt | 360 |
| cagcggcagc ggcagcggca ccgacttcac cctgaccatc agcagcctgc agcccgagga | 420 |
| cgtggccacc tactactgcc agagatacaa cagagccccc tacaccttcg gccagggcac | 480 |
| caaggtggag atcaagagaa ctgtggctgc accatctgtc ttcatcttcc cgccatctga | 540 |
| tgagcagttg aaatctggaa ctgcctctgt tgtgtgcctg ctgaataact tctatcccag | 600 |
| agaggccaaa gtacagtgga aggtggataa cgccctccaa tcgggtaact cccaggagag | 660 |
| tgtcacagag caggacagca aggacagcac ctacagcctc agcagcaccc tgacgctgag | 720 |
| caaagcagac tacgagaaac acaaactcta cgcctgcgaa gtcacccatc agggcctgag | 780 |
| ctcgcccgtc acaaagagct tcaacagggg agagtgcctc gagcgagcaa acgagcacc | 840 |
| agtaaaacaa acactaaact tcgacctact aaaactagca ggagacgtag aatcaaaccc | 900 |
| aggaccagcc acaaccatgg agacagacac actcctgcta tgggtactgc tgctctgggt | 960 |
| tccaggttcc actggtgacg agcgcaaatg ttgtgtcgag tgccaccgt gccaggcgg | 1020 |
| ccgcggcggc ggcggcagcg gtcccctggg tgtgagaaga tctgaggtgc agctggtgga | 1080 |
| gagcggcggc ggcctggtgc agcccggcag aagcctgaga ctgagctgcg ccgcagcgg | 1140 |
| cttcaccttc gacgactacg ccatgcactg ggtgagacag gcccccggca agggcctgga | 1200 |
| gtgggtgagc gccatcacct ggaacagcgg ccacatcgac tacgccgaca gcgtggaggg | 1260 |
| cagattcacc atcagcagag acaacgccaa gaacagcctg tacctgcaga tgaacagcct | 1320 |
| gagagccgag gacaccgccg tgtactactg cgccaaggtg agctacctga gcaccgccag | 1380 |
| cagcctggac tactggggcc agggcaccct ggtgaccgtg agcagcgcct ccaccaaggg | 1440 |
| accatcggtc ttcccctgg caccctcctc aagagcacc tctggggca gcggccct | 1500 |
| gggctgcctg gtcaaggact acttccccga accggtgacg gtgtcgtgga actcaggcgc | 1560 |
| cctgaccagc ggcgtgcaca ccttcccggc tgtcctacag tcctcaggac tctactccct | 1620 |
| cagcagcgtg gtgaccgtgc cctccagcag cttgggcacc cagacctaca tctgcaacgt | 1680 |

```
gaatcacaag cccagcaaca ccaaggtcga caagaaagtt gagcccaaat cttgtgacaa    1740
aactcacaca tgcccaccgt gcccagcacc tgaactcctg ggggaccgt  cagtcttcct    1800 cttccccca aaacccaagg acaccctcat gatctcccgg acccctgagg tcacatgcgt     1860
ggtggtggac gtgagccacg aagaccctga ggtcaagttc aactggtacg tggacggcgt    1920
ggaggtgcat aatgccaaga caaagccgcg ggaggagcag tacaacagca cgtaccgggt    1980
ggtcagcgtc ctcaccgtcc tgcaccagga ctggctgaat ggcaaggagt acaagtgcaa    2040
ggtctccaac aaagccctcc cagcccccat cgagaaaacc atctccaaag ccaaagggca    2100
gccccgagaa ccacaggtgt acaccctgcc cccatcccgg gatgagctga ccaagaacca    2160
ggtcagcctg acctgcctgg tcaaaggctt ctatcccagc gacatcgccg tggagtggga    2220
gagcaatggg cagccggaga acaactacaa gaccacgcct cccgtgctgg actccgacgg    2280
ctccttcttc ctctacagca agctcaccgt ggacaagagc aggtggcagc aggggaacgt    2340
cttctcatgc tccgtgatgc atgaggctct gcacaaccac tacacgcaga agagcctctc    2400
cctgtctccg ggtaaataaa tcgatggcgc gcc                                 2433

<210> SEQ ID NO 31
<211> LENGTH: 2732
<212> TYPE: DNA
<213> ORGANISM: Artificial Sequence
<220> FEATURE:
<223> OTHER INFORMATION: IgG3 Hinge Humira

<400> SEQUENCE: 31
gctagcaagc ttgttatcca ccatggagac agacacactc ctgctatggg tactgctgct    60
ctgggttcca ggttccactg gtgacgagct caaaacccca cttggtgaca caactcacac    120
atgcccacgg tgcccagagc ccaaatcttg tgacacacct ccccgtgcc  cacggtgccc    180 agagcccaaa tcttgtgaca cacctccccc atgcccacgg tgcccagagc ccaaatcttg    240
tgacacacct ccccgtgcc  caaggtgccc agttaacggc ggcggcggca gcggtcccct    300
gggtgtgaga gcggcccagc cggccgacat ccagatgacc cagagcccca gcagcctgag    360
cgccagcgtg ggcgacagag tgaccatcac ctgcagagcc agcagggca  tcagaaacta    420 cctggcctgg taccagcaga agcccggcaa ggccccaag  ctgctgatct acgccgccag    480
caccctgcag agcggcgtgc ccagcagatt cagcggcagc ggcagcggca ccgacttcac    540
cctgaccTca gcagcctgca gcccgaggac gtggccacct actactgcca gagatacaac    600
agagccccct acaccttcgg ccagggcacc aaggtggaga tcaagagaac tgtggctgca    660
ccatctgtct tcatcttccc gccatctgat gagcagttga aatctggaac tgcctctgtt    720
gtgtgcctgc tgaataactt ctatcccaga gaggccaaag tacagtggaa ggtggataac    780
gccctccaat cgggtaactc ccaggagagt gtcacagagc aggacagcaa ggacagcacc    840
tacagcctca gcagcaccct gacgctgagc aaagcagact acgagaaaca caaactctac    900
gcctgcgaag tcacccatca gggcctgagc tcgcccgtca caaagagctt caacagggga    960
gagtgcctcg agcagcaaa  acgagcacca gtaaaacaaa cactaaactt cgacctacta    1020
aaactagcag agacgtaga  atcaaaccca ggaccagcca caaccatgga gacagacaca    1080
ctcctgctat gggtactgct gctctgggtt ccaggttcca ctggtgacga gctcaaaacc    1140
ccacttggtg acacaactca cacatgccca cggtgcccag agcccaaatc ttgtgacaca    1200 cctccccgt  gcccacggtg cccagagccc aaatcttgtg acacacctcc cccatgccca    1260
```

```
cggtgcccag agcccaaatc ttgtgacaca cctcccccgt gcccaaggtg cccaggcggc    1320
cgcggcggcg gcggcagcgg tccctgggt gtgagaagat ctgaggtgca gctggtggag     1380
agcggcggcg gcctggtgca gcccggcaga agcctgagac tgagctgcgc cgccagcggc    1440
ttcaccttcg acgactacgc catgcactgg gtgagacagg cccccggcaa gggcctggag    1500
tgggtgagcg ccatcacctg aacagcggc cacatcgact acgccgacag cgtggagggc     1560
agattcacca tcagcagaga aacgccaag aacagcctgt acctgcagat gaacagcctg     1620
agagccgagg acaccgccgt gtactactgc gccaaggtga gctacctgag caccgccagc    1680
agcctggact actggggcca gggcaccctg gtgaccgtga gcagcgcctc caccaaggga    1740
ccatcggtct tccccctggc acctcctcc aagagcacct ctgggggcac agcggccctg     1800
ggctgcctgg tcaaggacta cttccccgaa ccggtgacgg tgtcgtggaa ctcaggcgcc    1860
ctgaccagcg gcgtgcacac cttcccggct gtcctacagt cctcaggact ctactccctc    1920
agcagcgtgg tgaccgtgcc ctccagcagc ttgggcaccc agacctacat ctgcaacgtg    1980
aatcacaagc ccagcaacac caaggtcgac aagaaagttg agcccaaatc ttgtgacaaa    2040
actcacacat gcccaccgtg cccagcacct gaactcctgg ggggaccgtc agtcttcctc    2100
ttccccccaa acccaagga caccctcatg atctcccgga cccctgaggt cacatgcgtg     2160
gtggtggacg tgagccacga agaccctgag gtcaagttca actggtacgt ggacggcgtg    2220
gaggtgcata atgccaagac aaagccgcgg gaggagcagt acaacagcac gtaccgggtg    2280
gtcagcgtcc tcaccgtcct gcaccaggac tggctgaatg gcaaggagta caagtgcaag    2340
gtctccaaca aagccctccc agcccccatc gagaaaacca tctccaaagc caagggcag    2400
ccccgagaac cacaggtgta caccctgccc ccatcccggg atgagctgac caagaaccag    2460
gtcagcctga cctgcctggt caaaggcttc tatcccagcg acatcgccgt ggagtgggag    2520
agcaatgggc agccggagaa caactacaag accacgcctc ccgtgctgga ctccgacggc    2580
tccttcttcc tctacagcaa gctcaccgtg gacaagagca ggtggcagca ggggaacgtc    2640
ttctcatgct ccgtgatgca tgaggctctg cacaaccact acacgcagaa gagcctctcc    2700
ctgtctccgg gtaaataaat cgatggcgcg cc                                   2732

<210> SEQ ID NO 32
<211> LENGTH: 2433
<212> TYPE: DNA
<213> ORGANISM: Artificial Sequence
<220> FEATURE:
<223> OTHER INFORMATION: IgG4 Hinge Humira

<400> SEQUENCE: 32
gctagcaagc ttgttatcca ccatggagac agacacactc ctgctatggg tactgctgct     60
ctgggttcca ggttccactg gtgacgagtc caaatatggt cccccatgcc catcatgccc    120
agttaacggc ggcggcggca gcggtccct gggtgtgaga gcggcccagc cggccgacat     180
ccagatgacc cagagcccca gcagcctgag cgccagcgtg ggcgacagag tgaccatcac    240
ctgcagagcc agccagggca tcagaaacta cctggcctgg taccagcaga agcccggcaa    300
ggccccaag ctgctgatct acgccgccag caccctgcag agcggcgtgc cagcagatt     360
cagcggcagc ggcagcggca ccgacttcac cctgaccatc agcagcctgc agcccgagga    420
cgtggccacc tactactgcc agagatacaa cagagccccc tacaccttcg gccagggcac    480
caaggtggag atcaagagaa ctgtggctgc accatctgtc ttcatcttcc cgccatctga    540
tgagcagttg aaatctggaa ctgcctctgt tgtgtgcctg ctgaataact tctatcccag    600
```

```
agaggccaaa gtacagtgga aggtggataa cgccctccaa tcgggtaact cccaggagag    660
tgtcacagag caggacagca aggacagcac ctacagcctc agcagcaccc tgacgctgag    720
caaagcagac tacgagaaac acaaactcta cgcctgcgaa gtcacccatc agggcctgag    780
ctcgcccgtc acaaagagct tcaacagggg agagtgcctc gagcgagcaa acgagcacc    840 agtaaaacaa acactaaact tcgacctact aaaactagca ggagacgtag aatcaaaccc    900
aggaccagcc acaaccatgg agacagacac actcctgcta tgggtactgc tgctctgggt    960
tccaggttcc actggtgacg agtccaaata tggtccccca tgcccatcat gcccaggcgg   1020
ccgcggcggc ggcggcagcg gtcccctggg tgtgagaaga tctgaggtgc agctggtgga   1080
gagcggcggc ggcctggtgc agcccggcag aagcctgaga ctgagctgcg ccgccagcgg   1140
cttcaccttc gacgactacg ccatgcactg ggtgagacag gccccggca agggcctgga   1200 gtgggtgagc gccatcacct ggaacagcgg ccacatcgac tacgccgaca gcgtggaggg   1260
cagattcacc atcagcagag acaacgccaa gaacagcctg tacctgcaga tgaacagcct   1320
gagagccgag gacaccgccg tgtactactg cgccaaggtg agctacctga gcaccgccag   1380
cagcctggac tactggggcc agggcacccc tggtgaccgtg agcagcgcct ccaccaaggg   1440
accatcggtc ttccccctgg caccctcctc caagagcacc tctggggca gcggccct   1500 gggctgcctg gtcaaggact acttccccga accggtgacg gtgtcgtgga actcaggcgc   1560
cctgaccagc ggcgtgcaca ccttcccggc tgtcctacag tcctcaggac tctactccct   1620
cagcagcgtg gtgaccgtgc cctccagcag cttgggcacc cagacctaca tctgcaacgt   1680
gaatcacaag cccagcaaca ccaaggtcga caagaaagtt gagcccaaat cttgtgacaa   1740
aactcacaca tgcccaccgt gcccagcacc tgaactcctg ggggaccgt cagtcttcct   1800 cttccccccca aaacccaagg acaccctcat gatctcccgg acccctgagg tcacatgcgt   1860
ggtggtggac gtgagccacg aagaccctga ggtcaagttc aactggtacg tggacggcgt   1920
ggaggtgcat aatgccaaga caaagccgcg ggaggagcag tacaacagca cgtaccgggt   1980
ggtcagcgtc ctcaccgtcc tgcaccagga ctggctgaat ggcaaggagt acaagtgcaa   2040
ggtctccaac aaagccctcc cagcccccat cgagaaaacc atctccaaag ccaagggca   2100 gccccgagaa ccacaggtgt acaccctgcc cccatcccgg gatgagctga ccaagaacca   2160
ggtcagcctg acctgcctgg tcaaaggctt ctatcccagc gacatcgccg tggagtggga   2220
gagcaatggg cagccggaga acaactacaa gaccacgcct cccgtgctgg actccgacgg   2280
ctccttcttc ctctacagca agctcaccgt ggacaagagc aggtggcagc aggggaacgt   2340
cttctcatgc tccgtgatgc atgaggctct gcacaaccac tacacgcaga agagcctctc   2400
cctgtctccg ggtaaataaa tcgatggcgc gcc                                 2433
```

<210> SEQ ID NO 33
<211> LENGTH: 2475
<212> TYPE: DNA
<213> ORGANISM: Artificial Sequence
<220> FEATURE:
<223> OTHER INFORMATION: IgA1 Hinge Humira

<400> SEQUENCE: 33

```
gctagcaagc ttgttatcca ccatggagac agacacactc ctgctatggg tactgctgct     60
ctgggttcca ggttccactg gtgacccagt tccctcaact ccaccctaccc catctccctc    120 aactccacct accccatctc cctcatgctg ccacgttaac ggcggcggcg gcagcggtcc    180
```

```
cctgggtgtg agagcggccc agccggccga catccagatg acccagagcc ccagcagcct      240
gagcgccagc gtgggcgaca gagtgaccat cacctgcaga gccagccagg gcatcagaaa      300
ctacctggcc tggtaccagc agaagcccgg caaggccccc aagctgctga tctacgccgc      360
cagcaccctg cagagcggcg tgcccagcag attcagcggc agcggcagcg caccgactt       420 caccctgacc atcagcagcc tgcagcccga ggacgtggcc acctactact gccagagata      480
caacagagcc ccctcacacct tcggccaggg caccaaggtg gagatcaaga gaactgtggc     540
tgcaccatct gtcttcatct cccgccatc tgatgagcag ttgaaatctg gaactgcctc      600
tgttgtgtgc ctgctgaata acttctatcc cagagaggcc aaagtacagt ggaaggtgga      660
taacgccctc caatcgggta actcccagga gagtgtcaca gagcaggaca gcaaggacag      720
cacctacagc ctcagcagca ccctgacgct gagcaaagca gactacgaga acacaaaact     780
ctacgcctgc gaagtcaccc atcagggcct gagctcgccc gtcacaaaga gcttcaacag      840
gggagagtgc ctcgagcgag caaaacgagc accagtaaaa caaacactaa acttcgacct      900
actaaaacta gcaggagacg tagaatcaaa cccaggacca gccacaacca tggagacaga      960
cacactcctg ctatgggtac tgctgctctg ggttccaggt tccactggtg acgagcccaa     1020
atcttgtgac aaaactcaca catgcccacc gtgcccaggc ggccgcgcg gcggcggcag     1080 cggtcccctg ggtgtgagaa gatctgaggt gcagctggtg gagagcggcg gcggcctggt     1140
gcagcccggc agaagcctga gactgagctg cgccgccagc ggcttcacct tcgacgacta     1200
cgccatgcac tgggtgagac aggcccccgg caagggcctg gagtgggtga gcgccatcac     1260
ctggaacagc ggccacatcg actacgccga cagcgtggag ggcagattca ccatcagcag     1320
agacaacgcc aagaacagcc tgtacctgca gatgaacagc ctgagagccg aggacaccgc     1380
cgtgtactac tgcgccaagg tgagctacct gagcaccgcc agcagcctgg actactgggg     1440
ccagggcacc ctggtgaccg tgagcagcgc ctccaccaag ggaccatcgg tcttccccct     1500
ggcaccctcc tccaagagca cctctggggg cacagcggcc ctgggctgcc tggtcaagga     1560
ctacttcccc gaaccggtga cggtgtcgtg gaactcaggc gccctgacca gcggcgtgca     1620
caccttcccg gctgtcctac agtcctcagg actctactcc ctcagcagcg tggtgaccgt     1680
gccctccagc agcttgggca cccagaccta catctgcaac gtgaatcaca agcccagcaa     1740
caccaaggtc gacaagaaag ttgagcccaa atcttgtgac aaaactcaca catgcccacc     1800
gtgcccagca cctgaactcc tgggggggacc gtcagtcttc ctcttccccc caaaacccaa     1860
ggacaccctc atgatctccc ggacccctga ggtcacatgc gtggtggtgg acgtgagcca     1920
cgaagaccct gaggtcaagt tcaactggta cgtggacggc gtggaggtgc ataatgccaa     1980
gacaaagccg cgggaggagc agtacaacag cacgtaccgg gtggtcagcg tcctcaccgt     2040
cctgcaccag gactggctga atggcaagga gtacaagtgc aaggtctcca acaaagccct     2100
cccagccccc atcgagaaaa ccatctccaa agccaagggg cagccccgag aaccacaggt     2160
gtacaccctg cccccatccc gggatgagct gaccaagaac caggtcagcc tgacctgcct     2220
ggtcaaaggc ttctatccca gcgacatcgc cgtggagtgg gagagcaatg ggcagccgga     2280
gaacaactac aagaccacgc ctcccgtgct ggactccgac ggctccttct tcctctacag     2340
caagctcacc gtggacaaga gcaggtggca gcaggggaac gtcttctcat gctccgtgat     2400
gcatgaggct ctgcacaacc actacacgca gaagagcctc tccctgtctc cgggtaaata     2460
aatcgatggc gcgcc                                                     2475
```

<210> SEQ ID NO 34
<211> LENGTH: 2420
<212> TYPE: DNA
<213> ORGANISM: Artificial Sequence
<220> FEATURE:
<223> OTHER INFORMATION: IgA2 Hinge Humira

<400> SEQUENCE: 34

| | | | | | |
|---|---|---|---|---|---|
| gctagcaagc | ttgttatcca | ccatggagac | agacacactc | ctgctatggg | tactgctgct | 60 |
| ctgggttcca | ggttccactg | gtgacccagt | tcccccacct | ccccccatgct | gccacgttaa | 120 |
| cggcggcggc | ggcagcggtc | cctgggtgt | gagagcggcc | cagccggccg | acatccagat | 180 |
| gacccagagc | cccagcagcc | tgagcgccag | cgtgggcgac | agagtgacca | tcacctgcag | 240 |
| agccagccag | ggcatcagaa | actacctggc | ctggtaccag | cagaagcccg | gcaaggcccc | 300 |
| caagctgctg | atctacgccg | ccagcaccct | gcagagcggc | gtgccagca | gattcagcgg | 360 |
| cagcggcagc | ggcaccgact | tcaccctgac | catcagcagc | ctgcagcccg | aggacgtggc | 420 |
| cacctactac | tgccagagat | acaacagagc | ccctacacc | ttcggccagg | gcaccaaggt | 480 |
| ggagatcaag | agaactgtgg | ctgcaccatc | tgtcttcatc | ttcccgccat | ctgatgagca | 540 |
| gttgaaatct | ggaactgcct | ctgttgtgtg | cctgctgaat | aacttctatc | ccagagaggc | 600 |
| caaagtacag | tggaaggtgg | ataacgccct | ccaatcgggt | aactcccagg | agagtgtcac | 660 |
| agagcaggac | agcaaggaca | gcacctacag | cctcagcagc | accctgacgc | tgagcaaagc | 720 |
| agactacgag | aaacacaaac | tctacgcctg | cgaagtcacc | catcagggcc | tgagctcgcc | 780 |
| cgtcacaaag | agcttcaaca | ggggagagtg | cctcgagcga | gcaaaacgag | caccagtaaa | 840 |
| acaaacacta | aacttcgacc | tactaaaact | agcaggagac | gtagaatcaa | cccaggacc | 900 |
| agccacaacc | atggagacag | acacactcct | gctatggtac | tgctgctctg | gttccaggt | 960 |
| tccactggtg | acccagttcc | cccacctccc | ccatgctgcc | acggcggccg | cggcggcggc | 1020 |
| ggcagcggtc | cctgggtgt | gagaagatct | gaggtgcagc | tggtggagag | cggcggcggc | 1080 |
| ctggtgcagc | ccggcagaag | cctgagactg | agctgcgccg | ccagcggctt | caccttcgac | 1140 |
| gactacgcca | tgcactgggt | gagacaggcc | cccggcaagg | gcctgagtg | ggtgagcgcc | 1200 |
| atcacctgga | acagcggcca | catcgactac | gccgacagcg | tggagggcag | attcaccatc | 1260 |
| agcagagaca | acgccaagaa | cagcctgtac | ctgcagatga | acagcctgag | agccgaggac | 1320 |
| accgccgtgt | actactgcgc | caaggtgagc | tacctgagca | ccgccagcag | cctgactac | 1380 |
| tggggccagg | gcaccctggt | gaccgtgagc | agcgcctcca | ccaagggacc | atcggtcttc | 1440 |
| cccctggcac | cctcctccaa | gagcacctct | gggggcacag | cggccctggg | ctgcctggtc | 1500 |
| aaggactact | tccccgaacc | ggtgacggtg | tcgtggaact | caggcgccct | gaccagcggc | 1560 |
| gtgcacacct | tccggctgt | cctacagtcc | tcaggactct | actccctcag | cagcgtggtg | 1620 |
| accgtgccct | ccagcagctt | gggcacccag | acctacatct | gcaacgtgaa | tcacaagccc | 1680 |
| agcaacacca | aggtcgacaa | gaaagttgag | cccaaatctt | gtgacaaaac | tcacacatgc | 1740 |
| ccaccgtgcc | cagcacctga | actcctgggg | ggaccgtcag | tcttcctctt | ccccccaaaa | 1800 |
| cccaaggaca | ccctcatgat | ctcccggacc | cctgaggtca | catgcgtggt | ggtggacgtg | 1860 |
| agccacgaag | accctgaggt | caagttcaac | tggtacgtgg | acggcgtgga | ggtgcataat | 1920 |
| gccaagacaa | agccgcggga | ggagcagtac | aacagcacgt | accgggtggt | cagcgtcctc | 1980 |
| accgtcctgc | accaggactg | gctgaatggc | aaggagtaca | agtgcaaggt | ctccaacaaa | 2040 |
| gccctcccag | ccccatcga | gaaaaccatc | tccaaagcca | aagggcagcc | ccgagaacca | 2100 |

| | |
|---|---|
| caggtgtaca ccctgccccc atcccgggat gagctgacca agaaccaggt cagcctgacc | 2160 |
| tgcctggtca aaggcttcta tcccagcgac atcgccgtgg agtgggagag caatgggcag | 2220 |
| ccggagaaca actacaagac cacgcctccc gtgctggact ccgacggctc cttcttcctc | 2280 |
| tacagcaagc tcaccgtgga caagagcagg tggcagcagg ggaacgtctt ctcatgctcc | 2340 |
| gtgatgcatg aggctctgca caaccactac acgcagaaga gcctctccct gtctccgggt | 2400 |
| aaataaatcg atggcgcgcc | 2420 |

<210> SEQ ID NO 35
<211> LENGTH: 2465
<212> TYPE: DNA
<213> ORGANISM: Artificial Sequence
<220> FEATURE:
<223> OTHER INFORMATION: IgG1 Hinge Panitumumab

<400> SEQUENCE: 35

| | |
|---|---|
| gctagcaagc ttgttatcca ccatggagac agacacactc ctgctatggg tactgctgct | 60 |
| ctgggttcca ggttccactg gtgacgagcc caaatcttgt gacaaaactc acacatgccc | 120 |
| accgtgccca gttaacggcg gcggcggcag cggtcccctg ggtgtgagag cggcccagcc | 180 |
| ggcgatattg tgatgaccca gagccgctg agcctgccgg tgaccccagg cgaaccggcg | 240 |
| tcgattagct gccgcagctc gcagaacatc gtgcataata acggcattac ctatctggaa | 300 |
| tggtatctgc agaaaccggg ccaaagcccg cagctgttaa tttataaagt gagcgatcgc | 360 |
| tttagcggcg tgccggatcg cttttcgggc agcggtagtg gcaccgattt tacgctgaaa | 420 |
| attagccgcg tggaagcgga ggatgttggc gtgtattact gctttcaggg cagccatatc | 480 |
| ccgccaacct ttggccaagg caccaaagtg gaaattaaac gcgcgcggac tgtggctgca | 540 |
| ccatctgtct tcatcttccc gccatctgat gagcagttga aatctggaac tgcctctgtt | 600 |
| gtgtgcctgc tgaataactt ctatcccaga gaggccaaag tacagtggaa ggtggataac | 660 |
| gccctccaat cgggtaactc ccaggagagt gtcacagagc aggacagcaa ggacagcacc | 720 |
| tacagcctca gcagcaccct gacgctgagc aaagcagact acgagaaaca caaactctac | 780 |
| gcctgcgaag tcacccatca gggcctgagc tcgcccgtca caaagagctt caacagggga | 840 |
| gagtgcctcg agcgagcaaa acgagcacca gtaaaacaaa cactaaactt cgacctacta | 900 |
| aaactagcag gagacgtaga atcaaaccca ggaccagcca caaccatgga gacagacaca | 960 |
| ctcctgctat gggtactgct gctctgggtt ccaggttcca ctggtgacga gcccaaatct | 1020 |
| tgtgacaaaa ctcacacatg cccaccgtgc ccaggcggcc gcggcggcgg cggcagcggt | 1080 |
| cccctgggtg tgagaagatc tcaggtgcaa ctggttcaga gcggcgcgga agtgaaaaag | 1140 |
| ccgggcgcgt cggttaaagt gagctgcaaa gcctcaggct ataccttttac gagctactgg | 1200 |
| atgcattggg tgcgccaggc cccgggtcag ggcctggaat ggatgggtaa catttatccg | 1260 |
| ggcagcggtg gcaccaacta tgcggaaaaa tttaagaacc gcgtgaccat gacgcgtgat | 1320 |
| accagcattt cgacggccta tatggaactg agccgcctgc gtagcgatga caccgccgtg | 1380 |
| tattactgcg cgcgcagtgg cggtccgtat ttttttcgatt actggggcca gggtacgctg | 1440 |
| gttaccgtga gctcggcctc caccaaggga ccatcggtct tccccctggc accctcctcc | 1500 |
| aagagcacct ctgggggcac agcggccctg ggctgcctgg tcaaggacta cttccccgaa | 1560 |
| ccggtgacgg tgtcgtggaa ctcaggcgcc ctgaccagcg gcgtgcacac cttcccggct | 1620 |
| gtcctacagt cctcaggact ctactccctc agcagcgtgg tgaccgtgcc ctccagcagc | 1680 |
| ttgggcaccc agacctacat ctgcaacgtg aatcacaagc ccagcaacac caaggtggac | 1740 |

```
aagagagttg tcgacgagcc caaatcttgt gacaaaactc acacatgccc accgtgccca   1800
gcacctgaac tcctgggggg accgtcagtc ttcctcttcc ccccaaaacc caaggacacc   1860
ctcatgatct cccggacccc tgaggtcaca tgcgtggtgg tggacgtgag ccacgaagac   1920
cctgaggtca agttcaactg gtacgtggac ggcgtggagg tgcataatgc caagacaaag   1980
ccgcgggagg agcagtacaa cagcacgtac cgtgtggtca gcgtcctcac cgtcctgcac   2040
caggactggc tgaatggcaa ggagtacaag tgcaaggtct ccaacaaagc cctcccagcc   2100
cccatcgaga aaaccatctc caaagccaaa gggcagcccc gagaaccaca ggtgtacacc   2160
ctgcccccat cccgggagga tgaccaagaa ccaggtcagc ctgacctg cctggtcaaa     2220 ggcttctatc ccagcgacat cgccgtggag tgggagagca atgggcagcc ggagaacaac   2280
tacaagacca cgcctcccgt gctggactcc gacggctcct tcttcctcta tagcaagctc   2340
accgtggaca agagcaggtg gcagcagggg aacgtcttct catgctccgt gatgcatgag   2400
gctctgcaca accactacac gcagaagagc ctctccctgt ccccgggtaa atcgatggc   2460 gcgcc                                                               2465

<210> SEQ ID NO 36
<211> LENGTH: 2439
<212> TYPE: DNA
<213> ORGANISM: Artificial Sequence
<220> FEATURE:
<223> OTHER INFORMATION: IgG1 Hinge Prolia

<400> SEQUENCE: 36
gctagcaagc ttgttatcca ccatggagac agacacactc ctgctatggg tactgctgct     60
ctgggttcca ggttccactg gtgacgagcc caaatcttgt gacaaaactc acacatgccc    120
accgtgccca gttaacggcg gcggcggcag cggtcccctg gtgtgagag cggcccagcc     180 ggccgaaatt gtgttgacgc agtctccagg caccctgtct ttgtctccag ggaaagagc     240 caccctctcc tgtagggcca gtcagagtgt tcgcggcagg tacttagcct ggtaccagca    300
gaaacctggc caggctccca ggctcctcat ctatggtgca tccagcaggg ccactggcat    360
cccagacagg ttcagtggca gtgggtctgg gacagacttc actctcacca tcagcagact    420
ggagcctgaa gattttgcag tgttttactg tcagcagtat ggtagttcac ctcggacgtt    480
cggccaaggg accaaggtgg aaatcaaacg aactgtggct gcaccatctg tcttcatctt    540
cccgccatct gatgagcagt tgaaatctgg aactgcctct gttgtgtgcc tgctgaataa    600
cttctatccc agagaggcca agtacagtg aaggtggat aacgccctcc aatcgggtaa      660
ctcccaggag agtgtcacag agcaggacag caaggacagc acctacagcc tcagcagcac    720
cctgacgctg agcaaagcag actacgagaa acacaaactc tacgcctgcg aagtcacccca   780 tcagggcctg agctcgcccg tcacaaagag cttcaacagg ggagagtgcc tcgagcgagc    840
aaaacgagca ccagtaaaac aaacactaaa cttcgaccta ctaaaactag caggagacgt    900
agaatcaaac ccaggaccag ccacaaccat ggagacagac acactcctgc tatgggtact   960
gctgctctgg gttccaggtt ccactggtga cgagcccaaa tcttgtgaca aaactcacac   1020
atgcccaccg tgcccaggcg ccgcggcgg cggcggcagc ggtccctgg tgtgagaag     1080 atctgaagtg aagctggagg agtctggagg aggcttggtg caacctggag gatccatgaa   1140
actctcctgt gttgcctctg gattcatttt cagtaaccac tggatgaact gggtccgcca   1200
gtctccagag aaggggcttg agtgggttgc tgaaattaga tcaaaatcta ttaattctgc   1260
```

| | |
|---|---|
| aacacattat gcggagtctg tgaaagggag gttcaccatc tcaagagatg attccaaaag | 1320 |
| tgctgtctac ctgcaaatga ccgacttaag aactgaagac actggcgttt attactgttc | 1380 |
| caggaattac tacggtagta cctacgacta ctggggccaa ggcaccactc tcacagtctc | 1440 |
| ctcagcctcc accaagggcc catcggtctt ccccctggca cctcctcca agagcacctc | 1500 |
| tgggggcaca gcggccctgg gctgcctggt caaggactac ttccccgaac cggtgacggt | 1560 |
| gtcgtggaac tcaggcgccc tgaccagcgg cgtgcacacc ttcccggctg tcctacagtc | 1620 |
| ctcaggactc tactccctca gcagcgtggt gaccgtgccc tccagcagct gggcaccca | 1680 |
| gacctacatc tgcaacgtga atcacaagcc cagcaacacc aaggtcgaca gacagttga | 1740 |
| gcgcaaatgt tgtgtcgagt gcccaccgtg cccagcacca cctgtggcag gaccgtcagt | 1800 |
| cttcctcttc cccccaaaac ccaaggacac cctcatgatc tcccggaccc ctgaggtcac | 1860 |
| gtgcgtggtg gtggacgtga gccacgaaga ccccgaggtc cagttcaact ggtacgtgga | 1920 |
| cggcgtggag gtgcataatg ccaagacaaa gccacgggag gagcagttca acagcacgtt | 1980 |
| ccgtgtggtc agcgtcctca ccgtcgtgca ccaggactgg ctgaacggca aggagtacaa | 2040 |
| gtgcaaggtc tccaacaaag gcctcccagc ccccatcgag aaaaccatct ccaaaaccaa | 2100 |
| agggcagccc cgagaaccac aggtgtacac cctgcccca tcccgggagg agatgaccaa | 2160 |
| gaaccaggtc agcctgacct gcctggtcaa aggcttctac cccagcgaca tcgccgtgga | 2220 |
| gtgggagagc aatgggcagc cggagaacaa ctacaagacc acacctccca tgctggactc | 2280 |
| cgacggctcc ttcttcctct acagcaagct caccgtggac aagagcaggt ggcagcaggg | 2340 |
| gaacgtcttc tcatgctccg tgatgcatga ggctctgcac aaccactaca cacagaagag | 2400 |
| cctctccctg tctccgggta ataaatcga tggcgcgcc | 2439 |

<210> SEQ ID NO 37
<211> LENGTH: 2421
<212> TYPE: DNA
<213> ORGANISM: Artificial Sequence
<220> FEATURE:
<223> OTHER INFORMATION: IgG2 Hinge Prolia

<400> SEQUENCE: 37

| | |
|---|---|
| gctagcaagc ttgttatcca ccatggagac agacacactc ctgctatggg tactgctgct | 60 |
| ctgggttcca ggttccactg gtgacgagcg caaatgttgt gtcgagtgcc accgtgccc | 120 |
| agttaacggc ggcggcggca gcggtcccct gggtgtgaga gcggcccagc cggccgaaat | 180 |
| tgtgttgacg cagtctccag gcaccctgtc tttgtctcca ggggaaagag ccaccctctc | 240 |
| ctgtagggcc agtcagagtg ttcgcggcag gtacttagcc tggtaccagc agaaacctgg | 300 |
| ccaggctccc aggctcctca tctatggtgc atccagcagg gccactggca tcccagacag | 360 |
| gttcagtggc agtgggtctg ggacagactt cactctcacc atcagcagac tggagcctga | 420 |
| agattttgca gtgttttact gtcagcagta tggtagttca cctcggacgt tcggccaagg | 480 |
| gaccaaggtg gaaatcaaac gaactgtggc tgcaccatct gtcttcatct tcccgccatc | 540 |
| tgatgagcag ttgaaatctg gaactgcctc tgttgtgtgc ctgctgaata acttctatcc | 600 |
| cagagaggcc aaagtacagt ggaaggtgga taacgccctc caatcgggta actcccagga | 660 |
| gagtgtcaca gagcaggaca gcaaggacag cacctacagc ctcagcagca cctgacgct | 720 |
| gagcaaagca gactacgaga aacacaaact ctacgcctgc gaagtcaccc atcagggcct | 780 |
| gagctcgccc gtcacaaaga gcttcaacag gggagagtgc ctcagcgag caaaacgagc | 840 |
| accagtaaaa caaacactaa acttcgacct actaaaacta gcaggagacg tagaatcaaa | 900 |

```
cccaggacca gccacaacca tggagacaga cacactcctg ctatgggtac tgctgctctg      960
ggttccaggt tccactggtg acgagcgcaa atgttgtgtc gagtgccac cgtgcccagg      1020
cggccgcggc ggcggcggca gcggtcccct gggtgtgaga agatctgaag tgaagctgga    1080
ggagtctgga ggaggcttgg tgcaacctgg aggatccatg aaactctcct gtgttgcctc    1140
tggattcatt ttcagtaacc actggatgaa ctgggtccgc cagtctccag agaagggct     1200
tgagtgggtt gctgaaatta gatcaaaatc tattaattct gcaacacatt atgcggagtc    1260
tgtgaaaggg aggttcacca tctcaagaga tgattccaaa agtgctgtct acctgcaaat    1320
gaccgactta agaactgaag acactggcgt ttattactgt tccaggaatt actacggtag    1380
tacctacgac tactggggcc aaggcaccac tctcacagtc tcctcagcct ccaccaaggg    1440
cccatcggtc ttccccctgg cacctcctc caagagcacc tctgggggca gcggccct      1500
gggctgcctg gtcaaggact acttccccga accggtgacg gtgtcgtgga actcaggcgc   1560
cctgaccagc ggcgtgcaca ccttcccggc tgtcctacag tcctcaggac tctactccct   1620
cagcagcgtg gtgaccgtgc cctccagcag cttgggcacc cagacctaca tctgcaacgt   1680
gaatcacaag cccagcaaca ccaaggtcga caagacagtt gagcgcaaat gttgtgtcga   1740
gtgcccaccg tgcccagcac cacctgtggc aggaccgtca gtcttcctct tccccccaaa   1800
acccaaggac accctcatga tctcccggac ccctgaggtc acgtgcgtgg tggtggacgt   1860
gagccacgaa gaccccgagg tccagttcaa ctggtacgtg gacggcgtgg aggtgcataa   1920
tgccaagaca aagccacggg aggagcagtt caacagcacg ttccgtgtgg tcagcgtcct   1980
caccgtcgtg caccaggact ggctgaacgg caaggagtac aagtgcaagg tctccaacaa   2040
aggcctccca gcccccatcg agaaaaccat ctccaaaacc aaagggcagc ccgagaacc    2100
acaggtgtac accctgcccc catcccggga ggagatgacc aagaaccagg tcagcctgac   2160
ctgcctggtc aaaggcttct accccagcga catcgccgtg gagtgggaga gcaatgggca   2220
gccggagaac aactacaaga ccacacctcc catgctggac tccgacggct ccttcttcct   2280
ctacagcaag ctcaccgtgg acaagagcag gtggcagcag gggaacgtct tctcatgctc   2340
cgtgatgcat gaggctctgc acaaccacta cacacagaag agcctctccc tgtctccggg   2400
taaataaatc gatggcgcgc c                                             2421
```

<210> SEQ ID NO 38
<211> LENGTH: 2759
<212> TYPE: DNA
<213> ORGANISM: Artificial Sequence
<220> FEATURE:
<223> OTHER INFORMATION: IgG3 Hinge Prolia

<400> SEQUENCE: 38

```
gctagcaagc ttgttatcca ccatggagac agacacactc ctgctatggg tactgctgct    60
ctgggttcca ggttccactg gtgacgagct caaaaccca cttggtgaca caactcacac     120
atgcccacgg tgcccagagc ccaaatcttg tgacacacct ccccgtgcc cacggtgccc    180
agagcccaaa tcttgtgaca cacctccccc atgcccacgg tgcccagagc ccaaatcttg    240
tgacacacct ccccgtgcc caaggtgccc agttaacggg gcggcggca gcggtcccct    300
gggtgtgaga gcggcccagc cggccgaaat tgtgttgacg cagtctccag gcaccctgtc    360
tttgtctcca ggggaaagag ccaccctctc ctgtagggcc agtcagagtg ttcgcggcag    420
gtacttagcc tggtaccagc agaaacctgg ccaggctccc aggctcctca tctatggtgc    480
```

```
atccagcagg gccactggca tcccagacag gttcagtggc agtgggtctg ggacagactt    540
cactctcacc atcagcagac tggagcctga agattttgca gtgttttact gtcagcagta    600
tggtagttca cctcggacgt tcggccaagg gaccaaggtg gaaatcaaac gaactgtggc    660
tgcaccatct gtcttcatct tcccgccatc tgatgagcag ttgaaatctg gaactgcctc    720
tgttgtgtgc ctgctgaata acttctatcc cagagaggcc aaagtacagt ggaaggtgga    780
taacgccctc caatcgggta actcccagga gagtgtcaca gagcaggaca gcaaggacag    840
cacctacagc ctcagcagca ccctgacgct gagcaaagca gactacgaga aacacaaact    900
ctacgcctgc gaagtcaccc atcagggcct gagctcgccc gtcacaaaga gcttcaacag    960
gggagagtgc ctcgagcgag caaaacgagc accagtaaaa caaacactaa acttcgacct    1020
actaaaacta gcaggagacg tagaatcaaa cccaggacca gccacaacca tggagacaga    1080
cacactcctg ctatgggtac tgctgctctg ggttccaggt tccactggtg acgagctcaa    1140
aaccccactt ggtgacacaa ctcacacatg cccacggtgc ccagagccca atcttgtga     1200 cacacctccc ccgtgcccac ggtgcccaga gcccaaatct tgtgacacac ctcccccatg    1260
cccacggtgc ccagagccca atcttgtga cacacctccc ccgtgcccaa ggtgcccagg     1320
cggccgcggc ggcggcggca gcggtcccct gggtgtgaga agatctgaag tgaagctgga    1380
ggagtctgga ggaggcttgg tgcaacctgg aggatccatg aaactctcct gtgttgcctc    1440
tggattcatt ttcagtaacc actggatgaa ctgggtccgc cagtctccag agaaggggct    1500
tgagtgggtt gctgaaatta gatcaaaatc tattaattct gcaacacatt atgcggagtc    1560
tgtgaaaggg aggttcacca tctcaagaga tgattccaaa agtgctgtct acctgcaaat    1620
gaccgactta agaactgaag acactggcgt ttattactgt tccaggaatt actacggtag    1680
tacctacgac tactggggcc aaggcaccac tctcacagtc tcctcagcct ccaccaaggg    1740
cccatcggtc ttccccctgg caccctcctc caagagcacc tctgggggca gcggccct     1800 gggctgcctg gtcaaggact acttccccga accggtgacg gtgtcgtgga actcaggcgc    1860
cctgaccagc ggcgtgcaca ccttcccggc tgtcctacag tcctcaggac tctactccct    1920
cagcagcgtg gtgaccgtgc cctccagcag cttgggcacc cagacctaca tctgcaacgt    1980
gaatcacaag cccagcaaca ccaaggtcga caagacagtt gagcgcaaat gttgtgtcga    2040
gtgcccaccg tgcccagcac cacctgtggc aggaccgtca gtcttcctct tccccccaaa    2100
acccaaggac accctcatga tctcccggac ccctgaggtc acgtgcgtgg tggtggacgt    2160
gagccacgaa gaccccgagg tccagttcaa ctggtacgtg gacggcgtgg aggtgcataa    2220
tgccaagaca aagccacggg aggagcagtt caacagcacg ttccgtgtgg tcagcgtcct    2280
caccgtcgtg caccaggact ggctgaacgg caaggagtac aagtgcaagg tctccaacaa    2340
aggcctccca gcccccatcg agaaaaccat ctccaaaacc aaagggcagc ccgagaacc     2400 acaggtgtac accctgcccc catcccggga ggagatgacc aagaaccagg tcagcctgac    2460
ctgcctggtc aaaggcttct accccagcga catcgccgtg gagtgggaga gcaatgggca    2520
gccggagaac aactacaaga ccacacctcc catgctggac tccgacggct ccttcttcct    2580
ctacagcaag ctcaccgtgg acaagagcag gtggcagcag gggaacgtct tctcatgctc    2640
cgtgatgcat gaggctctgc acaaccacta cacacagaag agcctctccc tgtctccggg    2700
taaataaaca cgcagaagag cctctccctg tctccgggta aataaatcga tggcgcgcc    2759
```

<210> SEQ ID NO 39
<211> LENGTH: 2421

<212> TYPE: DNA
<213> ORGANISM: Artificial Sequence
<220> FEATURE:
<223> OTHER INFORMATION: IgG4 Hinge Prolia

<400> SEQUENCE: 39

```
gctagcaagc ttgttatcca ccatggagac agacacactc ctgctatggg tactgctgct      60
ctgggttcca ggttccactg gtgacgagtc caaatatggt cccccatgcc catcatgccc     120
agttaacggc ggcggcggca gcggtcccct gggtgtgaga gcggcccagc cggccgaaat     180
tgtgttgacg cagtctccag gcaccctgtc tttgtctcca ggggaaagag ccaccctctc     240
ctgtagggca agtcagagtg ttcgcggcag gtacttagcc tggtaccagc agaaacctgg     300
ccaggctccc aggctcctca tctatggtgc atccagcagg gccactggca tcccagacag     360
gttcagtggc agtgggtctg gacagactt cactctcacc atcagcagac tggagcctga     420
agattttgca gtgttttact gtcagcagta tggtagttca cctcggacgt tcggccaagg     480
gaccaaggtg gaaatcaaac gaactgtggc tgcaccatct gtcttcatct tcccgccatc     540
tgatgagcag ttgaaatctg gaactgcctc tgttgtgtgc ctgctgaata acttctatcc     600
cagagaggcc aaagtacagt ggaaggtgga taacgccctc caatcgggta actcccagga     660
gagtgtcaca gagcaggaca gcaaggacag cacctacagc ctcagcagca cctgacgct     720
gagcaaagca gactacgaga acacaaaact ctacgcctgc gaagtcaccc atcagggcct     780
gagctcgccc gtcacaaaga gcttcaacag gggagagtgc ctcgagcgag caaaacgagc     840
accagtaaaa caaacactaa acttcgacct actaaaacta gcaggagacg tagaatcaaa     900
cccaggacca gccacaacca tggagacaga cacactcctg ctatgggtac tgctgctctg     960
ggttccaggt tccactggtg acgagtccaa atatggtccc ccatgccat catgcccagg    1020
cggccgcggc ggcggcggca gcggtcccct gggtgtgaga gatctgaag tgaagctgga    1080
ggagtctgga ggaggcttgg tgcaacctgg aggatccatg aaactctcct gtgttgcctc    1140
tggattcatt ttcagtaacc actggatgaa ctgggtccgc cagtctccag agaagggct    1200
tgagtgggtt gctgaaatta gatcaaaatc tattaattct gcaacacatt atgcggagtc    1260
tgtgaaaggg aggttcacca tctcaagaga tgattccaaa agtgctgtct acctgcaaat    1320
gaccgactta agaactgaag acactggcgt ttattactgt tccaggaatt actacggtag    1380
tacctacgac tactgggggcc aaggcaccac tctcacagtc tcctcagcct ccaccaaggg    1440
cccatcggtc ttccccctgg caccctcctc caagagcacc tctggggca gcggccct     1500
gggctgcctg gtcaaggact acttccccga accggtgacg gtgtcgtgga actcaggcgc    1560
cctgaccagc ggcgtgcaca ccttcccggc tgtcctacag tcctcaggac tctactccct    1620
cagcagcgtg gtgaccgtgc cctccagcag cttgggcacc cagacctaca tctgcaacgt    1680
gaatcacaag cccagcaaca ccaaggtcga caagacagtt gagcgcaaat gttgtgtcga    1740
gtgcccaccg tgcccagcac cacctgtggc aggaccgtca gtcttcctct tccccccaaaa    1800
acccaaggac accctcatga tctcccggac ccctgaggtc acgtgcgtgg tggtggacgt    1860
gagccacgaa gaccccgagg tccagttcaa ctggtacgtg gacggcgtgg aggtgcataa    1920
tgccaagaca aagccacggg aggagcagtt caacagcacg ttccgtgtgg tcagcgtcct    1980
caccgtcgtg caccaggact ggctgaacgg caaggagtac aagtgcaagg tctccaacaa    2040
aggcctccca gccccatcg agaaaaccat ctccaaaacc aaagggcagc ccgagaacc    2100
acaggtgtac accctgcccc catcccggga ggagatgacc aagaaccagg tcagcctgac    2160
```

```
ctgcctggtc aaaggcttct accccagcga catcgccgtg gagtgggaga gcaatgggca    2220
gccggagaac aactacaaga ccacacctcc catgctggac tccgacggct ccttcttcct    2280
ctacagcaag ctcaccgtgg acaagagcag gtggcagcag gggaacgtct tctcatgctc    2340
cgtgatgcat gaggctctgc acaaccacta cacacagaag agcctctccc tgtctccggg    2400
taaataaatc gatggcgcgc c                                              2421
```

<210> SEQ ID NO 40
<211> LENGTH: 2463
<212> TYPE: DNA
<213> ORGANISM: Artificial Sequence
<220> FEATURE:
<223> OTHER INFORMATION: IgA1 Hinge Prolia

<400> SEQUENCE: 40

```
gctagcaagc ttgttatcca ccatggagac agacacactc ctgctatggg tactgctgct      60
ctgggttcca ggttccactg gtgacccagt tccctcaact ccacctaccc catctccctc     120
aactccacct accccatctc cctcatgctg ccacgttaac ggcggcggcg gcagcggtcc     180
cctgggtgtg agagcggccc agccggccga aattgtgttg acgcagtctc caggcaccct     240
gtctttgtct ccaggggaaa gagccaccct ctcctgtagg gccagtcaga gtgttcgcgg     300
caggtactta gcctggtacc agcagaaacc tggccaggct cccaggctcc tcatctatgg     360
tgcatccagc agggccactg gcatcccaga caggttcagt ggcagtgggt ctgggacaga     420
cttcactctc accatcagca gactggagcc tgaagatttt gcagtgtttt actgtcagca     480
gtatggtagt tcacctcgga cgttcggcca agggaccaag gtggaaatca aacgaactgt     540
ggctgcacca tctgtcttca tcttcccgcc atctgatgag cagttgaaat ctggaactgc     600
ctctgttgtg tgcctgctga ataacttcta tcccagagag gccaaagtac agtggaaggt     660
ggataacgcc ctccaatcgg gtaactccca ggagagtgtc acagagcagg acagcaagga     720
cagcacctac agcctcagca gcaccctgac gctgagcaaa gcagactacg agaaacacaa     780
actctacgcc tgcgaagtca cccatcaggg cctgagctcg cccgtcacaa agagcttcaa     840
caggggagag tgcctcgagc gagcaaaacg agcaccagta aaacaaacac taaacttcga     900
cctactaaaa ctagcaggag acgtagaatc aaacccagga ccagccacaa ccatggagac     960
agacacactc ctgctatggg tactgctgct ctgggttcca ggttccactg gtgacgagcc    1020
caaatcttgt gacaaaactc acacatgccc accgtgccca ggcggccgcg gcggcggcgg    1080
cagcggtccc ctgggtgtga aagatctga agtgaagctg gaggagtctg gaggaggctt    1140
ggtgcaacct ggaggatcca tgaaactctc ctgtgttgcc tctggattca ttttcagtaa    1200
ccactggatg aactgggtcc gccagtctcc agagaagggg cttgagtggg ttgctgaaat    1260
tagatcaaaa tctattaatt ctgcaacaca ttatgcggag tctgtgaaag ggaggttcac    1320
catctcaaga gatgattcca aaagtgctgt ctacctgcaa atgaccgact aagaactga    1380 agacactggc gtttattact gttccaggaa ttactacggt agtacctacg actactgggg    1440
ccaaggcacc actctcacag tctcctcagc ctccaccaag ggcccatcgg tcttcccct    1500 ggcaccctcc tccaagagca cctctggggg cacagcggcc ctgggctgcc tggtcaagga    1560
ctacttcccc gaaccggtga cggtgtcgtg gaactcaggc gccctgacca gcggcgtgca    1620
caccttcccg gctgtcctac agtcctcagg actctactcc ctcagcagcg tggtgaccgt    1680
gccctccagc agcttgggca cccagaccta catctgcaac gtgaatcaca agcccagcaa    1740
caccaaggtc gacaagacag ttgagcgcaa atgttgtgtc gagtgcccac cgtgcccagc    1800
```

```
accacctgtg gcaggaccgt cagtcttcct cttcccccca aaacccaagg acaccctcat   1860
gatctcccgg accectgagg tcacgtgcgt ggtggtggac gtgagccacg aagaccccga   1920
ggtccagttc aactggtacg tggacggcgt ggaggtgcat aatgccaaga caaagccacg   1980
ggaggagcag ttcaacagca cgttccgtgt ggtcagcgtc ctcaccgtcg tgcaccagga   2040
ctggctgaac ggcaaggagt acaagtgcaa ggtctccaac aaaggcctcc cagccccat    2100 cgagaaaacc atctccaaaa ccaaagggca gccccgagaa ccacaggtgt acaccctgcc   2160
cccatcccgg gaggagatga ccaagaacca ggtcagcctg acctgcctgg tcaaaggctt   2220
ctaccccagc gacatcgccg tggagtggga gagcaatggg cagccggaga caactacaa    2280 gaccacacct cccatgctgg actccgacgg ctccttcttc ctctacagca agctcaccgt   2340
ggacaagagc aggtggcagc aggggaacgt cttctcatgc tccgtgatgc atgaggctct   2400
gcacaaccac tacacacaga gagcctctc cctgtctccg ggtaaataaa tcgatggcgc   2460
gcc                                                                2463

<210> SEQ ID NO 41
<211> LENGTH: 2409
<212> TYPE: DNA
<213> ORGANISM: Artificial Sequence
<220> FEATURE:
<223> OTHER INFORMATION: IgA2 Hinge Prolia

<400> SEQUENCE: 41
gctagcaagc ttgttatcca ccatggagac agacacactc ctgctatggg tactgctgct     60
ctgggttcca ggttccactg gtgacccagt tcccccacct ccccatgct gccacgttaa    120 cggcggcggc ggcagcggtc ccctgggtgt gagagcggcc cagccggccg aaattgtgtt    180
gacgcagtct ccaggcaccc tgtctttgtc tcaggggaa agagccaccc tctcctgtag    240
ggccagtcag agtgttcgcg gcaggtactt agcctggtac cagcagaaac ctggccaggc    300
tcccaggctc ctcatctatg gtgcatccag cagggccact ggcatcccag acaggttcag    360
tggcagtggg tctgggacag acttcactct caccatcagc agactggagc ctgaagattt    420
tgcagtgttt tactgtcagc agtatggtag ttcacctcgg acgttcggcc aagggaccaa    480
ggtggaaatc aaacgaactg tggctgcacc atctgtcttc atcttcccgc catctgatga    540
gcagttgaaa tctggaactg cctctgttgt gtgcctgctg aataacttct atcccagaga    600
ggccaaagta cagtggaagg tggataacgc cctccaatcg ggtaactccc aggagagtgt    660
cacagagcag gacagcaagg acagcaccta cagcctcagc agcaccctga cgctgagcaa    720
agcagactac gagaaacaca aactctacgc ctgcgaagtc acccatcagg gcctgagctc    780
gcccgtcaca aagagcttca acaggggaga gtgcctcgag cgagcaaaac gagcaccagt    840
aaaacaaaca ctaaacttcg acctactaaa actagcagga gacgtagaat caaacccagg    900
accagccaca accatggaga cagacacact cctgctatgg gtactgctgc tctgggttcc    960
aggttccact ggtgacccag ttcccccacc tccccatgc tgccacggcg gccgcggcgg    1020
cggcggcagc ggtcccctgg gtgtgagaag atctgaagtg aagctggagg agtctggagg    1080
aggcttggtg caacctggag gatccatgaa actctcctgt gttgcctctg gattcatttt    1140
cagtaaccac tggatgaact gggtccgcca gtctccagag aaggggcttg agtgggttgc    1200
tgaaattaga tcaaaatcta ttaattctgc aacacattat gcggagtctg tgaaagggag    1260
gttcaccatc tcaagagatg attccaaaag tgctgtctac ctgcaaatga ccgacttaag    1320
```

```
aactgaagac actggcgttt attactgttc caggaattac tacggtagta cctacgacta   1380
ctggggccaa ggcaccactc tcacagtctc ctcagcctcc accaaggggcc catcggtctt   1440 ccccctggca ccctcctcca agagcacctc tgggggcaca gcggccctgg gctgcctggt   1500
caaggactac ttccccgaac cggtgacggt gtcgtggaac tcaggcgccc tgaccagcgg   1560
cgtgcacacc ttcccggctg tcctacagtc ctcaggactc tactccctca gcagcgtggt   1620
gaccgtgccc tccagcagct gggcaccca gacctacatc tgcaacgtga atcacaagcc   1680
cagcaacacc aaggtcgaca gacagttga gcgcaaatgt tgtgtcgagt gcccaccgtg   1740
cccagcacca cctgtggcag gaccgtcagt cttcctcttc cccccaaaac ccaaggacac   1800
cctcatgatc tcccggaccc ctgaggtcac gtgcgtggtg gtggacgtga gccacgaaga   1860
ccccgaggtc cagttcaact ggtacgtgga cggcgtggag gtgcataatg ccaagacaaa   1920
gccacgggag gagcagttca acagcacgtt ccgtgtggtc agcgtcctca ccgtcgtgca   1980
ccaggactgg ctgaacggca aggagtacaa gtgcaaggtc tccaacaaag gcctcccagc   2040
ccccatcgag aaaaccatct ccaaaaccaa agggcagccc cgagaaccac aggtgtacac   2100
cctgccccca tcccgggagg agatgaccaa gaaccaggtc agcctgacct gcctggtcaa   2160
aggcttctac cccagcgaca tcgccgtgga gtgggagagc aatgggcagc cggagaacaa   2220
ctacaagacc acacctccca tgctggactc cgacggctcc ttcttcctct acagcaagct   2280
caccgtggac aagagcaggt ggcagcaggg gaacgtcttc tcatgctccg tgatgcatga   2340
ggctctgcac aaccactaca cacagaagag cctctccctg tctccgggta aataaatcga   2400
tggcgcgcc                                                         2409

<210> SEQ ID NO 42
<211> LENGTH: 2419
<212> TYPE: DNA
<213> ORGANISM: Artificial Sequence
<220> FEATURE:
<223> OTHER INFORMATION: IgG1 Hinge Raptiva

<400> SEQUENCE: 42
aagcttgtta tccaccatgg agacagacac actcctgcta tgggtactgc tgctctgggt     60
tccaggttcc actggtgacg agcccaaatc ttgtgacaaa actcacacat gcccaccgtg    120
cccagttaac ggcggcggcg gcagccccctt cagagcggcc cagccggccg acatccagat    180
gacccagagc cccagcagcc tgagcgccag cgtgggcgac agagtgacca tcacctgcag    240
agccagcaag accatcagca gtacctggc ctggtaccag cagaagcccg gcaaggcccc    300
caagctgctg atctacagcg gcagcaccct gcagagcggc gtgccagca gattcagcgg    360 cagcggcagc ggcaccgact tcaccctgac catcagcagc ctgcagcccg aggacttcgc    420
cacctactac tgccagcagc acaacgagta ccccctgacc ttcggccagg gcaccaaggt    480
ggagatcaag agaactgtgg ctgcaccatc tgtcttcatc ttcccgccat ctgatgagca    540
gttgaaatct ggaactgcct ctgttgtgtg cctgctgaat aacttctatc ccagagaggc    600
caaagtacag tggaaggtgg ataacgccct ccaatcgggt aactcccagg agagtgtcac    660
agagcaggac agcaaggaca gcacctacag cctcagcagc accctgacgc tgagcaaagc    720
agactacgag aaacacaaac tctacgcctg cgaagtcacc catcagggcc tgagctcgcc    780
cgtcacaaag agcttcaaca ggggagagtg cctcgagcga gcaaaacgag caccagtaaa    840
acaaacacta aacttcgacc tactaaaact agcaggagac gtagaatcaa acccaggacc    900
agccacaacc atggagacag acacactcct gctatgggta ctgctgctct gggttccagg    960
```

```
ttccactggt gacgagccca aatcttgtga caaaactcac acatgcccac cgtgcccagg    1020
cggccgcggc ggcggcggca gcccctt cag aagatctgag gtgcagctgg tggagagcgg    1080
cggcggcctg gtgcagcccg gcggcagcct gagactgagc tgcgccgcca gcggctacag    1140
cttcaccggc cactggatga actgggtgag acaggccccc ggcaagggcc tggagtgggt    1200
gggcatgatc caccccagcg acagcgagac cagatacaac cagaagttca aggacagatt    1260
caccatcagc gtgacaagag caagaacac cctgtacctg cagatgaaca gcctgagagc    1320
cgaggacacc gccgtgtact actgcgccag aggcatctac ttctacggca ccacctactt    1380
cgactactgg ggccagggca ccctggtgac cgtctcctca gcctccacca agggaccatc    1440
ggtcttcccc ctggcaccct cctccaagag cacctctggg ggcacagcgg ccctgggctg    1500
cctggtcaag gactacttcc ccgaaccggt gacggtgtcg tggaactcag gcgccctgac    1560
cagcggcgtg cacaccttcc cggctgtcct acagtcctca ggactctact ccctcagcag    1620
cgtggtgacc gtgccctcca gcagcttggg cacccagacc tacatctgca acgtgaatca    1680
caagcccagc aacaccaagg tcgacaagaa agttgagccc aaatcttgtg acaaaactca    1740
cacatgccca ccgtgcccag cacctgaact cctgggggga ccgtcagtct tcctcttccc    1800
cccaaaaccc aaggacaccc tcatgatctc ccggacccct gaggtcacat gcgtggtggt    1860
ggacgtgagc cacgaagacc ctgaggtcaa gttcaactgg tacgtggacg gcgtggaggt    1920
gcataatgcc aagacaaagc cgcgggagga gcagtacaac agcacgtacc gggtggtcag    1980
cgtcctcacc gtcctgcacc aggactggct gaatggcaag gagtacaagt gcaaggtctc    2040
caacaaagcc ctcccagccc ccatcgagaa aaccatctcc aaagccaaag gcagccccg    2100 agaaccacag gtgtacaccc tgcccccatc ccgggatgag ctgaccaaga accaggtcag    2160
cctgacctgc ctggtcaaag gcttctatcc cagcgacatc gccgtggagt gggagagcaa    2220
tgggcagccg gagaacaact acaagaccac gcctcccgtg ctggactccg acggctcctt    2280
cttcctctac agcaagctca ccgtggacaa gagcaggtgg cagcagggga acgtcttctc    2340
atgctccgtg atgcatgagg ctctgcacaa ccactacacg cagaagagcc tctccctgtc    2400
tccgggtaaa taaatcgat                                                 2419
```

<210> SEQ ID NO 43
<211> LENGTH: 2448
<212> TYPE: DNA
<213> ORGANISM: Artificial Sequence
<220> FEATURE:
<223> OTHER INFORMATION: IgG1 Hinge Remicade

<400> SEQUENCE: 43

```
gctagcaagc ttgttatcca ccatggagac agacacactc ctgctatggg tactgctgct     60
ctgggttcca ggttccactg gtgacgagcc caaatcttgt gacaaaactc acacatgccc    120
accgtgccca gttaacggcg gcggcggcag cggtccctg gtgtgagag cggcccagcc    180 ggccgacatc ttgctgactc agtctccagc catcctgtct gtgagtccag agaaagagt    240 cagtttctcc tgcagggcca gtcagttcgt tggctcaagc atccactggt atcagcaaag    300
aacaaatggt tctccaaggc ttctcataaa gtatgcttct gagtctatgt ctgggatccc    360
ttccaggttt agtggcagtg gatcagggac agattttact cttagcatca acactgtgga    420
gtctgaagat attgcagatt attactgtca acaaagtcat agctggccat tcacgttcgg    480
ctcggggaca aatttggaag taaacggac tgtggctgca ccatctgtct tcatcttccc    540
```

| | |
|---|---|
| gccatctgat gagcagttga aatctggaac tgcctctgtt gtgtgcctgc tgaataactt | 600 |
| ctatcccaga gaggccaaag tacagtggaa ggtggataac gccctccaat cgggtaactc | 660 |
| ccaggagagt gtcacagagc aggacagcaa ggacagcacc tacagcctca gcagcaccct | 720 |
| gacgctgagc aaagcagact acgagaaaca caaactctac gcctgcgaag tcacccatca | 780 |
| gggcctgagc tcgcccgtca caaagagctt caacagggga gagtgcctcg agcgagcaaa | 840 |
| acgagcacca gtaaaacaaa cactaaactt cgacctacta aaactagcag agacgtaga | 900 |
| atcaaaccca ggaccagcca caaccatgga gacagacaca ctcctgctat gggtactgct | 960 |
| gctctgggtt ccaggttcca ctggtgacga gcccaaatct tgtgacaaaa ctcacacatg | 1020 |
| cccaccgtgc ccaggcggcc gcggcggcgg cggcagcggt cccctgggtg tgagaagatc | 1080 |
| tgaagtgaag ctggaggagt ctggaggagg cttggtgcaa cctggaggat ccatgaaact | 1140 |
| ctcctgtgtt gcctctggat tcattttcag taaccactgg atgaactggg tccgccagtc | 1200 |
| tccagagaag gggcttgagt gggttgctga aattagatca aaatctatta attctgcaac | 1260 |
| acattatgcg gagtctgtga agggaggtt caccatctca agagatgatt ccaaaagtgc | 1320 |
| tgtctacctg caaatgaccg acttaagaac tgaagacact ggcgtttatt actgttccag | 1380 |
| gaattactac ggtagtacct acgactactg gggccaaggc accactctca cagtctcctc | 1440 |
| agcctccacc aagggcccat cggtcttccc cctggcaccc tcctccaaga gcacctctgg | 1500 |
| gggcacagcg gccctgggct gcctggtcaa ggactacttc cccgaaccgg tgacggtgtc | 1560 |
| gtggaactca ggcgccctga ccagcggcgt gcacaccttc ccggctgtcc tacagtcctc | 1620 |
| aggactctac tccctcagca gcgtggtgac cgtgccctcc agcagcttgg gcacccagac | 1680 |
| ctacatctgc aacgtgaatc acaagcccag caacaccaag gtcgacaaga agttgagcc | 1740 |
| caaatcttgt gacaaaactc acacatgccc accgtgccca gcacctgaac tcctgggggg | 1800 |
| accgtcagtc ttcctcttcc ccccaaaacc caaggacacc ctcatgatct cccggacccc | 1860 |
| tgaggtcaca tgcgtggtgg tggacgtgag ccacgaagac cctgaggtca gttcaactg | 1920 |
| gtacgtggac ggcgtggagg tgcataatgc caagacaaag ccgcgggagg agcagtacaa | 1980 |
| cagcacgtac cgggtggtca gcgtcctcac cgtcctgcac caggactggc tgaatggcaa | 2040 |
| ggagtacaag tgcaaggtct ccaacaaagc cctcccagcc cccatcgaga aaaccatctc | 2100 |
| caaagccaaa gggcagcccc gagaaccaca ggtgtacacc ctgcccccat cccgggatga | 2160 |
| gctgaccaag aaccaggtca gcctgacctg cctggtcaaa ggcttctatc ccagcgacat | 2220 |
| cgccgtggag tgggagagca atgggcagcc ggagaacaac tacaagacca cgcctcccgt | 2280 |
| gctggactcc gacggctcct tcttcctcta cagcaagctc accgtggaca gagcaggtg | 2340 |
| gcagcagggg aacgtcttct catgctccgt gatgcatgag gctctgcaca accactacac | 2400 |
| gcagaagagc ctctccctgt ctccgggtaa ataaatcgat ggcgcgcc | 2448 |

```
<210> SEQ ID NO 44
<211> LENGTH: 2430
<212> TYPE: DNA
<213> ORGANISM: Artificial Sequence
<220> FEATURE:
<223> OTHER INFORMATION: IgG2 Hinge Remicade

<400> SEQUENCE: 44
```

| | |
|---|---|
| gctagcaagc ttgttatcca ccatggagac agacacactc ctgctatggg tactgctgct | 60 |
| ctgggttcca ggttccactg gtgacagcg caaatgttgt gtcgagtgcc caccgtgccc | 120 |
| agttaacggc ggcggcggca gcggtcccct gggtgtgaga gcggcccagc cggccgacat | 180 |

```
cttgctgact cagtctccag ccatcctgtc tgtgagtcca ggagaaagag tcagtttctc    240
ctgcagggcc agtcagttcg ttggctcaag catccactgg tatcagcaaa gaacaaatgg    300
ttctccaagg cttctcataa agtatgcttc tgagtctatg tctgggatcc cttccaggtt    360
tagtggcagt ggatcaggga cagattttac tcttagcatc aacactgtgg agtctgaaga    420
tattgcagat tattactgtc aacaaagtca tagctggcca ttcacgttcg gctcggggac    480
aaatttggaa gtaaaacgga ctgtggctgc accatctgtc ttcatcttcc cgccatctga    540
tgagcagttg aaatctggaa ctgcctctgt tgtgtgcctg ctgaataact ctatcccag    600 agaggccaaa gtacagtgga aggtggataa cgccctccaa tcgggtaact cccaggagag    660
tgtcacagag caggacagca aggacagcac ctacagcctc agcagcaccc tgacgctgag    720
caaagcagac tacgagaaac acaaactcta cgcctgcgaa gtcacccatc agggcctgag    780
ctcgcccgtc acaaagagct tcaacagggg agagtgcctc gagcgagcaa aacgagcacc    840
agtaaaacaa acactaaact tcgacctact aaaactagca ggagacgtag aatcaaaccc    900
aggaccagcc acaaccatgg agacagacac actcctgcta tgggtactgc tgctctgggt    960
tccaggttcc actggtgacg agcgcaaatg ttgtgtcgag tgccaccgt gcccaggcgg    1020 ccgcggcggc ggcggcagcg gtcccctggg tgtgagaaga tctgaagtga agctggagga   1080
gtctggagga ggcttggtgc aacctggagg atccatgaaa ctctcctgtg ttgcctctgg   1140
attcattttc agtaaccact ggatgaactg ggtccgccag tctccagaga aggggcttga   1200
gtgggttgct gaaattagat caaaatctat taattctgca acacattatg cggagtctgt   1260
gaaagggagg ttcaccatct caagagatga ttccaaaagt gctgtctacc tgcaaatgac   1320
cgacttaaga actgaagaca ctggcgttta ttactgttcc aggaattact acggtagtac   1380
ctacgactac tggggccaag gcaccactct cacagtctcc tcagcctcca ccaagggccc   1440
atcggtcttc cccctggcac cctcctccaa gagcacctct gggggcacag cggccctggg   1500
ctgcctggtc aaggactact ccccgaacc ggtgacggtg tcgtggaact caggcgccct   1560
gaccagcggc gtgcacacct tcccggctgt cctacagtcc tcaggactct actccctcag   1620
cagcgtggtg accgtgccct ccagcagctt gggcacccag acctacatct gcaacgtgaa   1680
tcacaagccc agcaacacca aggtcgacaa gaaagttgag cccaaatctt gtgacaaaac   1740
tcacacatgc ccaccgtgcc cagcacctga actcctgggg ggaccgtcag tcttcctctt   1800
ccccccaaaa cccaaggaca cctcatgat ctcccggacc cctgaggtca catgcgtggt   1860
ggtggacgtg agccacgaag accctgaggt caagttcaac tggtacgtgg acggcgtgga   1920
ggtgcataat gccaagacaa agccgcggga ggagcagtac aacagcacgt accgggtggt   1980
cagcgtcctc accgtcctgc accaggactg gctgaatggc aaggagtaca agtgcaaggt   2040
ctccaacaaa gccctcccag cccccatcga gaaaaccatc tccaaagcca agggcagcc   2100 ccgagaacca caggtgtaca ccctgccccc atcccgggat gagctgacca agaaccaggt   2160
cagcctgacc tgcctggtca aaggcttcta tcccagcgac atcgccgtgg agtgggagag   2220
caatgggcag ccggagaaca actacaagac cacgcctccc gtgctggact ccgacggctc   2280
cttcttcctc tacagcaagc tcaccgtgga caagagcagg tggcagcagg ggaacgtctt   2340
ctcatgctcc gtgatgcatg aggctctgca caaccactac acgcagaaga gcctctccct   2400
gtctccgggt aaataaatcg atggcgcgcc                                    2430
```

<210> SEQ ID NO 45

<211> LENGTH: 3048
<212> TYPE: DNA
<213> ORGANISM: Artificial Sequence
<220> FEATURE:
<223> OTHER INFORMATION: IgG3 Hinge Remicade

<400> SEQUENCE: 45

| | |
|---|---|
| gctagcaagc ttgttatcca ccatggagac agacacactc ctgctatggg tactgctgct | 60 |
| ctgggttcca ggttccactg gtgacgagct caaaacccca cttggtgaca caactcacac | 120 |
| atgcccacgg tgcccagagc ccaaatcttg tgacacacct ccccgtgcc acggtgccc | 180 |
| agagcccaaa tcttgtgaca cacctccccc atgcccacgg tgcccagagc ccaaatcttg | 240 |
| tgacacacct ccccgtgcc caaggtgccc agttaacggc ggcggcggca gcggtcccct | 300 |
| gggtgtgaga gcggcccagc cggccgacat cttgctgact cagtctccag ccatcctgtc | 360 |
| tgtgagtcca ggagaaagag tcagtttctc ctgcagggcc agtcagttcg ttggctcaag | 420 |
| catccactgg tatcagcaaa gaacaaatgg ttctccaagg cttctcataa agtatgcttc | 480 |
| tgagtctatg tctgggatcc cttccaggtt tagtggcagt ggatcaggga cagattttac | 540 |
| tcttagcatc aacactgtgg agtctgaaga tattgcagat tattactgtc aacaaagtca | 600 |
| tagctggcca ttcacgttcg gctcggggac aaatttggaa gtaaacgga ctgtggctgc | 660 |
| accatctgtc ttcatcttcc cgccatctga tgagcagttg aaatctggaa ctgcctctgt | 720 |
| tgtgtgcctg ctgaataact tctatcccag agaggccaaa gtacagtgga aggtggataa | 780 |
| cgccctccaa tcgggtaact cccaggagag tgtcacagag caggacagca aggacagcac | 840 |
| ctacagcctc agcagcaccc tgacgctgag caaagcagac tacgagaaac acaaactcta | 900 |
| cgcctgcgaa gtcacccatc agggcctgag ctcgcccgtc acaaagagct caacagggg | 960 |
| agagtgcctc gagcgagcaa acgagcacc agtaaaacaa acactaaact cgacctact | 1020 |
| aaaactagca ggagacgtag aatcaaaccc aggaccagcc acaaccatgg agacagacac | 1080 |
| actcctgcta tgggtactgc tgctctgggt tccaggttcc actggtgacg agctcaaaac | 1140 |
| cccacttggt gacacaactc acacatgccc acggtgccca gagcccaaat cttgtgacac | 1200 |
| acctcccccg tgcccacggt gcccagagcc caaatcttgt gacacacctc cccatgccc | 1260 |
| acggtgccca gagcccaaat cttgtgacac acctccccg tgcccaaggt gcccaggcgg | 1320 |
| ccgcggcggc ggcggcagcg gtccctgggt gtgagaaga tctgaagtga agctggagga | 1380 |
| gtctggagga ggcttggtgc aacctggagg atccatgaaa ctctcctgtg ttgcctctgg | 1440 |
| attcattttc agtaaccact ggatgaactg ggtccgccag tctccagaga aggggcttga | 1500 |
| gtgggttgct gaaattagat caaaatctat taattctgca acacattatg cggagtctgt | 1560 |
| gaaaggagg ttcaccatct caagagatga ttccaaaagt gctgtctacc tgcaaatgac | 1620 |
| cgacttaaga actgaagaca ctggcgttta ttactgttcc aggaattact acggtagtac | 1680 |
| ctacgactac tggggccaag gcaccactct cacagtctcc tcagcctcca ccaagggccc | 1740 |
| atcggtcttc cccctggcac cctcctccaa gagcacctct gggggcacag cggccctggg | 1800 |
| ctgcctggtc aaggactact tccccgaacc ggtgacggtg tcgtggaact caggcgccct | 1860 |
| gaccagcggc gtgcacacct tcccggctgt cctacagtcc tcaggactct actccctcag | 1920 |
| cagcgtggtg accgtgccct ccagcagctt gggcacccag acctacatct gcaacgtgaa | 1980 |
| tcacaagccc agcaacacca aggtcgacaa gaaagttgag cccaaatctt gtgacaaaac | 2040 |
| tcacacatgc ccaccgtgcc cagcacctga actcctgggg ggaccgtcag tcttcctctt | 2100 |
| ccccccaaaa cccaaggaca ccctcatgat ctcccggacc cctgaggtca catgcgtggt | 2160 |

-continued

```
ggtggacgtg agccacgaag accctgaggt caagttcaac tggtacgtgg acggcgtgga      2220
ggtgcataat gccaagacaa agccgcggga ggagcagtac aacagcacgt accgggtggt      2280
cagcgtcctc accgtcctgc accaggactg gctgaatggc aaggagtaca agtgcaaggt      2340
ctccaacaaa gccctcccag cccccatcga gaaaaccatc tccaaagcca agggcagcc       2400 ccgagaacca caggtgtaca ccctgccccc atcccgggat gagctgacca gaaccaggt       2460 cagcctgacc tgcctggtca aaggcttcta tcccagcgac atcgccgtgg agtgggagag      2520
caatgggcag ccggagaaca actacaagac cacgcctccc gtgctggact ccgacggctc      2580
cttcttcctc tacagcaagc tcaccgtgga caagagcagg tggcagcagg ggaacgtctt      2640
ctcatgctcc gtgatgcatg aggctctgca caaccactcc ccatcgaga aaaccatctc       2700 caaagccaaa gggcagcccc gagaaccaca ggtgtacacc ctgcccccat cccgggatga      2760
gctgaccaag aaccaggtca gcctgacctg cctggtcaaa ggcttctatc ccagcgacat      2820
cgccgtggag tgggagagca tgggcagcc ggagaacaac tacaagacca cgcctcccgt       2880
gctggactcc gacggctcct tcttcctcta cagcaagctc accgtggaca gagcaggtg      2940 gcagcagggg aacgtcttct catgctccgt gatgcatgag gctctgcaca accactacac      3000
gcagaagagc ctctccctgt ctccgggtaa ataaatcgat ggcgcgcc                   3048
```

<210> SEQ ID NO 46
<211> LENGTH: 2430
<212> TYPE: DNA
<213> ORGANISM: Artificial Sequence
<220> FEATURE:
<223> OTHER INFORMATION: IgG4 Hinge Remicade

<400> SEQUENCE: 46

```
gctagcaagc ttgttatcca ccatggagac agacacactc ctgctatggg tactgctgct       60
ctgggttcca ggttccactg gtgacgagtc caaatatggt cccccatgcc catcatgccc      120
agttaacggc ggcggcggca gcggtcccct gggtgtgaga gcggcccagc cggccgacat      180
cttgctgact cagtctccag ccatcctgtc tgtgagtcca ggagaaagag tcagtttctc      240
ctgcagggcc agtcagttcg ttggctcaag catccactgg tatcagcaaa gaacaaatgg      300
ttctccaagg cttctcataa agtatgcttc tgagtctatg tctgggatcc cttccaggtt      360
tagtggcagt ggatcaggga cagattttac tcttagcatc aacactgtgg agtctgaaga      420
tattgcagat tattactgtc aacaaagtca tagctggcca ttcacgttcg gctcggggac      480
aaatttggaa gtaaaacgga ctgtggctgc accatctgtc ttcatcttcc cgccatctga      540
tgagcagttg aaatctggaa ctgcctctgt tgtgtgcctg ctgaataact tctatcccag      600
agaggccaaa gtacagtgga aggtggataa cgccctccaa tcgggtaact cccaggagag      660
tgtcacagag caggacagca aggacagcac ctacagcctc agcagcaccc tgacgctgag      720
caaagcagac tacgagaaac acaaactcta cgcctgcgaa gtcacccatc agggcctgag      780
ctcgcccgtc acaaagagct tcaacagggg agagtgcctc gagcgagcaa acgagcacc       840 agtaaaacaa acactaaact tcgacctact aaaactagca ggagacgtag aatcaaaccc      900
aggaccagcc acaaccatgg agacagacac actcctgcta tgggtactgc tgctctgggt      960
tccaggttcc actggtgacg agtccaaata tggtccccca tgcccatcat gcccaggcgg     1020
ccgcggcggc ggcggcagcg gtcccctggg tgtgagaaga tctgaagtga agctggagga     1080
gtctggagga ggcttggtgc aacctggagg atccatgaaa ctctcctgtg ttgcctctgg     1140
```

| | |
|---|---:|
| attcattttc agtaaccact ggatgaactg ggtccgccag tctccagaga aggggcttga | 1200 |
| gtgggttgct gaaattagat caaaatctat taattctgca acacattatg cggagtctgt | 1260 |
| gaaagggagg ttcaccatct caagagatga ttccaaaagt gctgtctacc tgcaaatgac | 1320 |
| cgacttaaga actgaagaca ctggcgttta ttactgttcc aggaattact acggtagtac | 1380 |
| ctacgactac tggggccaag gcaccactct cacagtctcc tcagcctcca ccaagggccc | 1440 |
| atcggtcttc cccctggcac cctcctccaa gagcacctct gggggcacag cggccctggg | 1500 |
| ctgcctggtc aaggactact ccccgaacc ggtgacggtg tcgtggaact caggcgccct | 1560 |
| gaccagcggc gtgcacacct tcccggctgt cctacagtcc tcaggactct actccctcag | 1620 |
| cagcgtggtg accgtgccct ccagcagctt gggcacccag acctacatct gcaacgtgaa | 1680 |
| tcacaagccc agcaacacca aggtcgacaa gaaagttgag cccaaatctt gtgacaaaac | 1740 |
| tcacacatgc ccaccgtgcc cagcacctga actcctgggg ggaccgtcag tcttcctctt | 1800 |
| ccccccaaaa cccaaggaca cctcatgat ctccggacc cctgaggtca catgcgtggt | 1860 |
| ggtggacgtg agccacgaag accctgaggt caagttcaac tggtacgtgg acggcgtgga | 1920 |
| ggtgcataat gccaagacaa agccgcggga ggagcagtac aacagcacgt accgggtggt | 1980 |
| cagcgtcctc accgtcctgc accaggactg gctgaatggc aaggagtaca agtgcaaggt | 2040 |
| ctccaacaaa gccctcccag cccccatcga gaaaaccatc tccaaagcca aagggcagcc | 2100 |
| ccgagaacca caggtgtaca ccctgccccc atcccgggat gagctgacca agaaccaggt | 2160 |
| cagcctgacc tgcctggtca aaggcttcta tcccagcgac atcgccgtgg agtgggagag | 2220 |
| caatgggcag ccggagaaca actacaagac cacgcctccc gtgctggact ccgacggctc | 2280 |
| cttcttcctc tacagcaagc tcaccgtgga caagagcagg tggcagcagg ggaacgtctt | 2340 |
| ctcatgctcc gtgatgcatg aggctctgca caaccactac acgcagaaga gcctctccct | 2400 |
| gtctccgggt aaataaatcg atggcgcgcc | 2430 |

<210> SEQ ID NO 47
<211> LENGTH: 2421
<212> TYPE: DNA
<213> ORGANISM: Artificial Sequence
<220> FEATURE:
<223> OTHER INFORMATION: IgA1 Hinge Remicade

<400> SEQUENCE: 47

| | |
|---|---:|
| gctagcaagc ttgttatcca ccatggagac agacacactc ctgctatggg tactgctgct | 60 |
| ctgggttcca ggttccactg gtgacccagt tccctcaact ccaccataccc catctccctc | 120 |
| aactccacct accccatctc cctcatgctg ccacgttaac ggcggcggcg gcagcggtcc | 180 |
| cctgggtgtg agagcggccc agccggccag agtcagtttc cctgcaggg ccagtcagtt | 240 |
| cgttggctca agcatccact ggtatcagca agaacaaat ggttctccaa ggcttctcat | 300 |
| aaagtatgct tctgagtcta tgtctgggat cccttccagg tttagtgcca gtggatcagg | 360 |
| gacagatttt actcttagca tcaacactgt ggagtctgaa gatattgcag attattactg | 420 |
| tcaacaaagt catagctggc cattcacgtt cggctcgggg acaaatttgg aagtaaaacg | 480 |
| gactgtggct gcaccatctg tcttcatctt cccgccatct gatgagcagt tgaaatctgg | 540 |
| aactgcctct gttgtgtgcc tgctgaataa cttctatccc agagaggcca agtacagtg | 600 |
| gaaggtggat aacgccctcc aatcgggtaa ctcccaggag agtgtcacag agcaggacag | 660 |
| caaggacagc acctacagcc tcagcagcac cctgacgctg agcaaagcag actacgagaa | 720 |
| acacaaactc tacgcctgcg aagtcaccca tcagggcctg agctcgcccg tcacaaagag | 780 |

```
cttcaacagg ggagagtgcc tcgagcgagc aaaacgagca ccagtaaaac aaacactaaa      840
cttcgaccta ctaaaactag caggagacgt agaatcaaac ccaggaccag ccacaaccat      900
ggagacagac acactcctgc tatgggtact gctgctctgg gttccaggtt ccactggtga      960
cgagcccaaa tcttgtgaca aaactcacac atgcccaccg tgcccaggcg ccgcggcgg      1020 cggcggcagc ggtcccctgg gtgtgagaag atctgaagtg aagctggagg agtctggagg     1080
aggcttggtg caacctggag gatccatgaa actctcctgt gttgcctctg gattcatttt     1140
cagtaaccac tggatgaact gggtccgcca gtctccagag aaggggcttg agtgggttgc     1200
tgaaattaga tcaaaatcta ttaattctgc aacacattat gcggagtctg tgaaagggag     1260
gttcaccatc tcaagagatg attccaaaag tgctgtctac ctgcaaatga ccgacttaag     1320
aactgaagac actggcgttt attactgttc caggaattac tacggtagta cctacgacta     1380
ctggggccaa ggcaccactc tcacagtctc ctcagcctcc accaagggcc catcggtctt     1440 cccccctggca ccctcctcca agagcacctc tgggggcaca gcggccctgg gctgcctggt     1500
caaggactac ttccccgaac cggtgacggt gtcgtggaac tcaggcgccc tgaccagcgg     1560
cgtgcacacc ttcccggctg tcctacagtc ctcaggactc tactccctca gcagcgtggt    1620
gaccgtgccc tccagcagct tgggcaccca gacctacatc tgcaacgtga atcacaagcc    1680
cagcaacacc aaggtcgaca gaaagttga gcccaaatct tgtgacaaaa ctcacacatg    1740
cccaccgtgc ccagcacctg aactcctggg gggaccgtca gtcttcctct tccccccaaa    1800
acccaaggac accctcatga tctcccggac ccctgaggtc acatgcgtgg tggtggacgt    1860
gagccacgaa gaccctgagg tcaagttcaa ctggtacgtg gacggcgtgg aggtgcataa    1920
tgccaagaca aagccgcggg aggagcagta caacagcacg taccgggtgg tcagcgtcct    1980
caccgtcctg caccaggact ggctgaatgg caaggagtac aagtgcaagg tctccaacaa    2040 agcccctccca gccccccatcg agaaaaccat ctccaaagcc aaagggcagc ccgagaacc    2100 acaggtgtac accctgcccc catcccggga tgagctgacc aagaaccagg tcagcctgac    2160
ctgcctggtc aaaggcttct atcccagcga catcgccgtg gagtgggaga gcaatgggca    2220
gccggagaac aactacaaga ccacgcctcc cgtgctggac tccgacggct ccttcttcct    2280
ctacagcaag ctcaccgtgg acaagagcag gtggcagcag gggaacgtct tctcatgctc    2340
cgtgatgcat gaggctctgc acaaccacta cacgcagaag agcctctccc tgtctccggg    2400
taaataaatc gatggcgcgc c                                              2421
```

<210> SEQ ID NO 48
<211> LENGTH: 2418
<212> TYPE: DNA
<213> ORGANISM: Artificial Sequence
<220> FEATURE:
<223> OTHER INFORMATION: IgA2 Hinge Remicade

<400> SEQUENCE: 48

```
gctagcaagc ttgttatcca ccatggagac agacacactc ctgctatggg tactgctgct       60
ctgggttcca ggttccactg gtgacccagt tcccccacct cccccatgct gccacgttaa      120
cggcggcggc ggcagcggtc ccctgggtgt gagagcggcc cagccggccg acatcttgct      180
gactcagtct ccagccatcc tgtctgtgag tccaggagaa agagtcagtt tctcctgcag      240
ggccagtcag ttcgttggct caagcatcca ctggtatcag caaagaacaa atggttctcc      300
aaggcttctc ataaagtatg cttctgagtc tatgtctggg atcccttcca ggtttagtgg      360
```

```
cagtggatca gggacagatt ttactcttag catcaacact gtggagtctg aagatattgc    420
agattattac tgtcaacaaa gtcatagctg gccattcacg ttcggctcgg ggacaaattt    480
ggaagtaaaa cggactgtgg ctgcaccatc tgtcttcatc ttcccgccat ctgatgagca    540
gttgaaatct ggaactgcct ctgttgtgtg cctgctgaat aacttctatc ccagagaggc    600
caaagtacag tggaaggtgg ataacgccct ccaatcgggt aactcccagg agagtgtcac    660
agagcaggac agcaaggaca gcacctacag cctcagcagc accctgacgc tgagcaaagc    720
agactacgag aaacacaaac tctacgcctg cgaagtcacc catcagggcc tgagctcgcc    780
cgtcacaaag agcttcaaca ggggagagtg cctcgagcga gcaaaacgag accagtaaa    840
acaaacacta aacttcgacc tactaaaact agcaggagac gtagaatcaa acccaggacc    900
agccacaacc atggagacag acacactcct gctatgggta ctgctgctct gggttccagg    960
ttccactggt gacccagttc ccccacctcc cccatgctgc cacggcggcc gcggcggcgg   1020
cggcagcggt cccctgggtg tgagaagatc tgaagtgaag ctggaggagt ctggaggagg   1080
cttggtgcaa cctggaggat ccatgaaact ctcctgtgtt gcctctggat tcatttttcag   1140
taaccactgg atgaactggg tccgccagtc tccagaaaag gggcttgagt gggttgctga   1200
aattagatca aaatctatta attctgcaac acattatgcg gagtctgtga agggaggtt    1260
caccatctca agagatgatt ccaaaagtgc tgtctacctg caaatgaccg acttaagaac   1320
tgaagacact ggcgtttatt actgttccag gaattactac ggtagtacct acgactactg   1380
gggccaaggc accactctca cagtctcctc agcctccacc aagggcccat cggtcttccc   1440
cctggcaccc tcctccaaga gcacctctgg gggcacagcg gccctgggct gcctggtcaa   1500
ggactacttc cccgaaccgg tgacggtgtc gtggaactca ggcgccctga ccagcggcgt   1560
gcacaccttc ccggctgtcc tacagtcctc aggactctac tccctcagca gcgtggtgac   1620
cgtgccctcc agcagcttgg gcacccagac ctacatctgc aacgtgaatc acaagcccag   1680
caacaccaag gtcgacaaga agttgagcc caaatcttgt gacaaaactc acacatgccc   1740
accgtgccca gcacctgaac tcctgggggg accgtcagtc ttcctcttcc cccaaaaacc   1800
caaggacacc ctcatgatct cccggacccc tgaggtcaca tgcgtggtgg tggacgtgag   1860
ccacgaagac cctgaggtca agttcaactg gtacgtggac ggcgtggagg tgcataatgc   1920
caagacaaag ccgcgggagg agcagtacaa cagcacgtac cgggtggtca gcgtcctcac   1980
cgtcctgcac caggactggc tgaatggcaa ggagtacaag tgcaaggtct ccaacaaagc   2040
cctcccagcc cccatcgaga aaaccatctc caaagccaaa gggcagcccc gagaaccaca   2100
ggtgtacacc ctgcccccat cccgggatga gctgaccaag aaccaggtca gcctgacctg   2160
cctggtcaaa ggcttctatc ccagcgacat cgccgtggag tgggagagca atgggcagcc   2220
ggagaacaac tacaagacca cgcctcccgt gctggactcc gacggctcct tcttcctcta   2280
cagcaagctc accgtggaca agagcaggtg gcagcagggg aacgtcttct catgctccgt   2340
gatgcatgag gctctgcaca accactacac gcagaagagc ctctccctgt ctccgggtaa   2400
ataaatcgat ggcgcgcc                                                 2418
```

<210> SEQ ID NO 49
<211> LENGTH: 2413
<212> TYPE: DNA
<213> ORGANISM: Artificial Sequence
<220> FEATURE:
<223> OTHER INFORMATION: IgG1 Hinge Stelara

<400> SEQUENCE: 49

```
aagcttgtta tccaccatgg agacagacac actcctgcta tgggtactgc tgctctgggt      60
tccaggttcc actggtgacg agcccaaatc ttgtgacaaa actcacacat gcccaccgtg     120
cccagttaac ggcggcggcg gcagcccctt cagagcggcc cagccggccg acatccagat     180
gacccagagc cccagcagcc tgagcgccag cgtgggcgac agagtgacca tcacctgcag     240
agccagccag ggcatcagca gctggctggc ctggtaccag cagaagcccg agaaggcccc     300
caagagcctg atctacgccg ccagcagcct gcagagcggc gtgcccagca gattcagcgg     360
cagcggcagc ggcaccgact tcaccctgac catcagcagc ctgcagcccg aggacttcgc     420
cacctactac tgccagcagt acaacatcta cccctacacc ttcggccagg gcaccaagct     480
ggagatcaag agaactgtgg ctgcaccatc tgtcttcatc ttcccgccat ctgatgagca     540
gttgaaatct ggaactgcct ctgttgtgtg cctgctgaat aacttctatc ccagagaggc     600
caaagtacag tggaaggtgg ataacgccct ccaatcgggt aactcccagg agagtgtcac     660
agagcaggac agcaaggaca gcacctacag cctcagcagc accctgacgc tgagcaaagc     720
agactacgag aaacacaaac tctacgcctg cgaagtcacc catcagggcc tgagctcgcc     780
cgtcacaaag agcttcaaca ggggagagtg cctcgagcga gcaaaacgag caccagtaaa     840
acaaacacta aacttcgacc tactaaaact agcaggagac gtagaatcaa acccaggacc     900
agccacaacc atggagacag acacactcct gctatgggta ctgctgctct gggttccagg     960
ttccactggt gacgagccca atcttgtga caaaactcac acatgcccac cgtgcccagg    1020
cggccgcggc ggcggcggca gccccttcag aagatctgag gtgcagctgg tgcagagcgg    1080
cgccgaggtg aagaagcccg cgagagcct gaagatcagc tgcaagggca gcggctacag    1140
cttcaccacc tactggctgg gctgggtgag acagatgccc ggcaagggcc tggactggat    1200
cggcatcatg agccccgtgg acagcgacat cagatacagc cccagcttcc agggccaggt    1260
gaccatgagc gtggacaaga gcatcaccac cgcctacctg cagtggaaca gcctgaaggc    1320
cagcgacacc gccatgtact actgcgccag aagaagaccc ggccagggct acttcgactt    1380
ctggggccag ggcaccctgg tgaccgtgag cagcgcctcc accaagggac catcggtctt    1440
cccccctggca ccctcctcca agagcacctc tgggggcaca gcggcctgg gctgcctggt    1500
caaggactac ttccccgaac cggtgacggt gtcgtggaac tcaggcgccc tgaccagcgg    1560
cgtgcacacc ttcccggctg tcctacagtc ctcaggactc tactccctca gcagcgtggt    1620
gaccgtgccc tccagcagct gggcaccca gacctacatc tgcaacgtga atcacaagcc    1680
cagcaacacc aaggtcgaca gaaagttga gcccaaatct tgtgacaaaa ctcacacatg    1740
cccaccgtgc ccagcacctg aactcctggg gggaccgtca gtcttcctct tccccccaaa    1800
acccaaggac accctcatga tctcccggac ccctgaggtc acatgcgtgg tggtggacgt    1860
gagccacgaa gaccctgagg tcaagttcaa ctggtacgtg gacggcgtgg aggtgcataa    1920
tgccaagaca aagccgcggg aggagcagta caacagcacg taccgggtgg tcagcgtcct    1980
caccgtcctg caccaggact ggctgaatgg caaggagtac aagtgcaagg tctccaacaa    2040
agcccctcca gcccccatcg agaaaaccat ctccaaagcc aaagggcagc ccgagaacc    2100
acaggtgtac accctgcccc catcccggga tgagctgacc aagaaccagg tcagcctgac    2160
ctgcctggtc aaaggcttct atcccagcga catcgccgtg gagtgggaga gcaatgggca    2220
gccggagaac aactacaaga ccacgcctcc cgtgctggac tccgacggct ccttcttcct    2280
ctacagcaag ctcaccgtgg acaagagcag gtggcagcag gggaacgtct tctcatgctc    2340
```
cgtgatgcat gaggctctgc acaaccacta cacgcagaag agcctctccc tgtctccggg    2400
taaataaatc gat    2413

<210> SEQ ID NO 50
<211> LENGTH: 2459
<212> TYPE: DNA
<213> ORGANISM: Artificial Sequence
<220> FEATURE:
<223> OTHER INFORMATION: IgG1 Hinge Trastuzumab

<400> SEQUENCE: 50
gctagcaagc ttgttatcca ccatggagac agacacactc ctgctatggg tactgctgct      60
ctgggttcca ggttccactg gtgacgagcc caaatcttgt gacaaaactc acacatgccc     120
accgtgccca gttaacggcg gcggcggcag cggtcccctg ggtgtgagag cggcccagcc     180
ggcgacatcc agatgaccca gagccccagc agcctgagcg ccagcgtggg cgacagagtg     240
accatcacct gcagagccag ccaggacgtg aacaccgccg tggcctggta ccagcagaag     300
cccggcaagg cccccaagct gctgatctac agcgccagct cctgtacag cggcgtgccc      360
agcagattca gcggcagcag aagcggcacc gacttcaccc tgaccatcag cagcctgcag     420
cccgaggact cgccaccta ctactgccag cagcactaca ccacccccc caccttcggc       480
cagggcacca aggtggagat caagagaacc gtggccgccc cagcgtgtt catcttcccc      540
cccagcgacg agcagctgaa gagcggcacc gccagcgtgg tgtgcctgct gaacaacttc     600
taccccagag aggccaaggt gcagtggaag gtggacaacg ccctgcagag cggcaacagc     660
caggagagct gaccgagca ggacagcaag acagcaccct acagcctgag cagcaccctg      720
accctgagca aggccgacta cgagaagcac aaggtgtacg cctgcgaggt gacccaccag     780
ggcctgagca gccccgtgac caagagcttc aacagaggcg agtgcctcga gcagcaaaa      840
cgagcaccag taaacaaac actaaacttc gacctactaa aactagcagg agacgtagaa      900
tcaaacccag accagccac aaccatggag acagacacac tcctgctatg ggtactgctg      960
ctctggttc aggttccac tggtgacgag cccaaatctt gtgacaaaac tcacacatgc      1020
ccaccgtgcc caggcggccg cggcggcggc ggcagcggtc ccctgggtgt gagaagatct     1080
gaggtgcagc tggtggagag cggcggcggc ctggtgcagc ccggcggcag cctgagactg     1140
agctgcgccg ccagcggctt caacatcaag gacacctaca tccactgggt gagacaggcc     1200
cccggcaagg gcctggagtg ggtggcccaga atctaccccca ccaacggcta caccagatac     1260
gccgacagcg tgaagggcag attcaccatc agcgccgaca ccagcaagaa caccgcctac     1320
ctgcagatga acagcctgag agccgaggac accgccgtgt actactgcag cagatggggc     1380
ggcgacggct ctacgccat ggactactgg ggcagggca ccctggtgac cgtgagcagc       1440
gccagcacca agggccccag cgtgttcccc ctggcccccag cagcaagag caccagcggc     1500
ggcaccgccg ccctgggctg cctggtgaag gactacttcc ccgagcccgt gaccgtgagc     1560
tggaacagcg gcgccctgac cagcggcgtg cacaccttcc ccgccgtgct gcagagcagc     1620
ggcctgtaca gcctgagcag cgtggtgacc gtgcccagca gcctgggc acccagacc       1680
tacatctgca acgtgaacca caagcccagc aacaccaagg tggacaagaa ggtggtcgac     1740
aagaaagttg agcccaaatc ttgtgacaaa actcacacat gcccaccgtg cccagcacct     1800
gaactcctgg ggggaccgtc agtcttcctc ttccccccaa acccaagga caccctcatg     1860
atctcccgga cccctgaggt cacatgcgtg gtggtggacg tgagccacga agaccctgag     1920
gtcaagttca actggtacgt ggacggcgtg gaggtgcata atgccaagac aaagccgcgg     1980

```
gaggagcagt acaacagcac gtaccgggtg gtcagcgtcc tcaccgtcct gcaccaggac   2040
tggctgaatg gcaaggagta caagtgcaag gtctccaaca aagccctccc agcccccatc   2100
gagaaaacca tctccaaagc caaagggcag ccccgagaac acaggtgta caccctgccc   2160 ccatcccggg atgagctgac caagaaccag gtcagcctga cctgcctggt caaaggcttc   2220
tatcccagcg acatcgccgt ggagtgggag agcaatgggc agccggagaa caactacaag   2280
accacgcctc ccgtgctgga ctccgacggc tccttcttcc tctacagcaa gctcaccgtg   2340
gacaagagca ggtggcagca ggggaacgtc ttctcatgct ccgtgatgca tgaggctctg   2400
cacaaccact acacgcagaa gagcctctcc ctgtctccgg gtaaaatcga tggcgcgcc   2459
```

<210> SEQ ID NO 51
<211> LENGTH: 7
<212> TYPE: PRT
<213> ORGANISM: Artificial Sequence
<220> FEATURE:
<223> OTHER INFORMATION: MMP2 substrate

<400> SEQUENCE: 51

Pro Leu Gly Met Trp Ser Arg
1               5

<210> SEQ ID NO 52
<211> LENGTH: 7
<212> TYPE: PRT
<213> ORGANISM: Artificial Sequence
<220> FEATURE:
<223> OTHER INFORMATION: MMP2 substrate

<400> SEQUENCE: 52

Pro Leu Gly Leu Trp Ala Arg
1               5

<210> SEQ ID NO 53
<211> LENGTH: 8
<212> TYPE: PRT
<213> ORGANISM: Artificial Sequence
<220> FEATURE:
<223> OTHER INFORMATION: MMP2 substrate

<400> SEQUENCE: 53

Pro Gln Gly Ile Ala Gly Gln Arg
1               5

<210> SEQ ID NO 54
<211> LENGTH: 35
<212> TYPE: PRT
<213> ORGANISM: Artificial Sequence
<220> FEATURE:
<223> OTHER INFORMATION: IgD1 Hinge

<400> SEQUENCE: 54

Ser Pro Lys Ala Gln Ala Ser Ser Val Pro Thr Ala Gln Pro Gln Ala
1               5                   10                  15

Glu Gly Ser Leu Ala Lys Ala Thr Thr Ala Pro Ala Thr Thr Arg Asn
            20                  25                  30

Thr Glu Cys
        35

<210> SEQ ID NO 55
<211> LENGTH: 25
<212> TYPE: PRT

<210> SEQ ID NO 55
<211> LENGTH: 27
<212> TYPE: PRT
<213> ORGANISM: Artificial Sequence
<220> FEATURE:
<223> OTHER INFORMATION: IgD2 Hinge

<400> SEQUENCE: 55

Arg Gly Gly Glu Glu Lys Lys Lys Glu Lys Glu Lys Glu Gln Glu
1               5                   10                  15

Glu Arg Glu Thr Lys Thr Pro Glu Cys
            20                  25

<210> SEQ ID NO 56
<211> LENGTH: 105
<212> TYPE: DNA
<213> ORGANISM: Artificial Sequence
<220> FEATURE:
<223> OTHER INFORMATION: IgD1 Hinge

<400> SEQUENCE: 56
tctccaaagg cacaggcctc ctccgtgccc actgcacaac cccaagcaga gggcagcctc    60
gccaaggcaa ccacagcccc agccaccacc cgtaacacag agtgt                   105

<210> SEQ ID NO 57
<211> LENGTH: 75
<212> TYPE: DNA
<213> ORGANISM: Artificial Sequence
<220> FEATURE:
<223> OTHER INFORMATION: IgD2 Hinge

<400> SEQUENCE: 57
agaggaggag aagagaagaa gaaggagaag gagaaagagg aacaagaaga gagagagaca    60
aagacaccag agtgt                                                    75

<210> SEQ ID NO 58
<211> LENGTH: 450
<212> TYPE: PRT
<213> ORGANISM: Artificial Sequence
<220> FEATURE:
<223> OTHER INFORMATION: infliximab heavy chain

<400> SEQUENCE: 58

Glu Val Lys Leu Glu Glu Ser Gly Gly Gly Leu Val Gln Pro Gly Gly
1               5                   10                  15

Ser Met Lys Leu Ser Cys Val Ala Ser Gly Phe Ile Phe Ser Asn His
            20                  25                  30

Trp Met Asn Trp Val Arg Gln Ser Pro Glu Lys Gly Leu Glu Trp Val
        35                  40                  45

Ala Glu Ile Arg Ser Lys Ser Ile Asn Ser Ala Thr His Tyr Ala Glu
    50                  55                  60

Ser Val Lys Gly Arg Phe Thr Ile Ser Arg Asp Asp Ser Lys Ser Ala
65                  70                  75                  80

Val Tyr Leu Gln Met Thr Asp Leu Arg Thr Glu Asp Thr Gly Val Tyr
                85                  90                  95

Tyr Cys Ser Arg Asn Tyr Tyr Gly Ser Thr Tyr Asp Tyr Trp Gly Gln
            100                 105                 110

Gly Thr Thr Leu Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

-continued

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
        180                 185                 190

Ser Ser Ser Leu Gly Thr Gln Thr Tyr Ile Cys Asn Val Asn His Lys
    195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
        260                 265                 270

Asp Pro Glu Val Lys Phe Asn Trp Tyr Val Asp Gly Val Glu Val His
    275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
        340                 345                 350

Thr Leu Pro Pro Ser Arg Asp Glu Leu Thr Lys Asn Gln Val Ser Leu
    355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
        420                 425                 430

Glu Ala Leu His Asn His Tyr Thr Gln Lys Ser Leu Ser Leu Ser Pro
    435                 440                 445

Gly Lys
    450

<210> SEQ ID NO 59
<211> LENGTH: 385
<212> TYPE: PRT
<213> ORGANISM: Artificial Sequence
<220> FEATURE:
<223> OTHER INFORMATION: Panitumumab heavy chain

<400> SEQUENCE: 59

Gln Val Gln Leu Leu Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Ala Trp Val Arg Gln Met Pro Gly Lys Gly Leu Glu Tyr Met
        35                  40                  45

Gly Leu Ile Tyr Pro Gly Asp Ser Asp Thr Lys Tyr Ser Pro Ser Phe
    50                  55                  60

```
Gln Gly Gln Val Thr Ile Ser Val Asp Lys Ser Val Ser Thr Ala Tyr
 65                  70                  75                  80

Leu Gln Trp Ser Ser Leu Lys Pro Ser Asp Ser Ala Val Tyr Phe Cys
             85                  90                  95

Ala Arg His Asp Val Gly Tyr Cys Ser Ser Ser Asn Cys Ala Lys Trp
            100                 105                 110

Pro Glu Tyr Phe Gln His Trp Gly Gln Gly Thr Leu Val Thr Val Ser
        115                 120                 125

Ser Ala Ser Thr Lys Gly Pro Ser Val Phe Pro Leu Ala Pro Ser Ser
    130                 135                 140

Lys Ser Thr Ser Gly Gly Thr Ala Ala Leu Gly Cys Leu Val Lys Asp
145                 150                 155                 160

Tyr Phe Pro Glu Pro Val Thr Val Ser Trp Asn Ser Gly Ala Leu Thr
                165                 170                 175

Ser Gly Val His Thr Phe Pro Ala Val Leu Gln Ser Ser Gly Leu Tyr
            180                 185                 190

Ser Leu Ser Ser Val Val Thr Val Pro Ser Ser Ser Leu Gly Thr Gln
        195                 200                 205

Thr Tyr Ile Cys Asn Val Asn His Lys Pro Ser Asn Thr Lys Val Asp
    210                 215                 220

Lys Arg Val Val Asp Glu Pro Lys Ser Cys Asp Lys Thr His Thr Cys
225                 230                 235                 240

Pro Pro Cys Pro Ala Pro Glu Leu Leu Gly Gly Pro Ser Val Phe Leu
                245                 250                 255

Phe Pro Pro Lys Pro Lys Asp Thr Leu Met Ile Ser Arg Thr Pro Glu
            260                 265                 270

Val Thr Cys Val Val Val Asp Val Ser His Glu Asp Pro Glu Val Lys
        275                 280                 285

Phe Asn Trp Tyr Val Asp Gly Val Glu Val His Asn Ala Lys Thr Lys
    290                 295                 300

Pro Arg Glu Glu Gln Tyr Asn Ser Thr Tyr Arg Val Val Ser Val Leu
305                 310                 315                 320

Thr Val Leu His Gln Asp Trp Leu Asn Gly Lys Glu Tyr Lys Cys Lys
                325                 330                 335

Val Ser Asn Lys Ala Leu Pro Ala Pro Ile Glu Lys Thr Ile Ser Lys
            340                 345                 350

Ala Lys Gly Gln Pro Arg Glu Pro Gln Val Tyr Thr Leu Pro Pro Ser
        355                 360                 365

Arg Glu Glu Met Thr Lys Asn Gln Val Ser Leu Thr Cys Leu Val Lys
    370                 375                 380

Gly
385

<210> SEQ ID NO 60
<211> LENGTH: 439
<212> TYPE: PRT
<213> ORGANISM: Artificial Sequence
<220> FEATURE:
<223> OTHER INFORMATION: Trastuzumab heavy chain

<400> SEQUENCE: 60

Val Gln Leu Val Glu Ser Gly Gly Gly Leu Val Gln Pro Gly Gly Ser
1               5                   10                  15

Leu Arg Leu Ser Cys Ala Ala Ser Gly Phe Asn Ile Lys Asp Thr Tyr
            20                  25                  30
```

-continued

```
Ile His Trp Val Arg Gln Ala Pro Gly Lys Gly Leu Glu Trp Val Ala
        35                  40                  45
Arg Ile Tyr Pro Thr Asn Gly Tyr Thr Arg Tyr Ala Asp Ser Val Lys
 50                  55                  60
Gly Arg Phe Thr Ile Ser Ala Asp Thr Ser Lys Asn Thr Ala Tyr Leu
 65                  70                  75                  80
Gln Met Asn Ser Leu Arg Ala Glu Asp Thr Ala Val Tyr Tyr Cys Ser
                 85                  90                  95
Arg Trp Gly Gly Asp Gly Phe Tyr Ala Met Asp Tyr Trp Gly Gln Gly
            100                 105                 110
Thr Leu Val Thr Val Ser Ala Ser Thr Lys Gly Pro Ser Val Phe
        115                 120                 125
Pro Leu Ala Pro Ser Ser Lys Ser Thr Ser Gly Gly Thr Ala Ala Leu
130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Ser Leu Gly Thr Gln Thr Tyr Ile Cys Asn Val Asn His Lys Pro
        195                 200                 205
Ser Asn Thr Lys Val Asp Lys Lys Val Asp Lys Lys Val Glu Pro
    210                 215                 220
Lys Ser Cys Asp Lys Thr His Thr Cys Pro Pro Cys Pro Ala Pro Glu
225                 230                 235                 240
Leu Leu Gly Gly Pro Ser Val Phe Leu Phe Pro Pro Lys Pro Lys Asp
                245                 250                 255
Thr Leu Met Ile Ser Arg Thr Pro Glu Val Thr Cys Val Val Val Asp
            260                 265                 270
Val Ser His Glu Asp Pro Glu Val Lys Phe Asn Trp Tyr Val Asp Gly
        275                 280                 285
Val Glu Val His Asn Ala Lys Thr Lys Pro Arg Glu Glu Gln Tyr Asn
290                 295                 300
Ser Thr Tyr Arg Val Val Ser Val Leu Thr Val Leu His Gln Asp Trp
305                 310                 315                 320
Leu Asn Gly Lys Glu Tyr Lys Cys Lys Val Ser Asn Lys Ala Leu Pro
                325                 330                 335
Ala Pro Ile Glu Lys Thr Ile Ser Lys Ala Lys Gly Gln Pro Arg Glu
            340                 345                 350
Pro Gln Val Tyr Thr Leu Pro Pro Ser Arg Asp Glu Leu Thr Lys Asn
        355                 360                 365
Gln Val Ser Leu Thr Cys Leu Val Lys Gly Phe Tyr Pro Ser Asp Ile
370                 375                 380
Ala Val Glu Trp Glu Ser Asn Gly Gln Pro Glu Asn Asn Tyr Lys Thr
385                 390                 395                 400
Thr Pro Pro Val Leu Asp Ser Asp Gly Ser Phe Phe Leu Tyr Ser Lys
                405                 410                 415
Leu Thr Val Asp Lys Ser Arg Trp Gln Gln Gly Asn Val Phe Ser Cys
            420                 425                 430
Ser Val Met His Glu Ala Leu
                435
```

<210> SEQ ID NO 61
<211> LENGTH: 451
<212> TYPE: PRT
<213> ORGANISM: Artificial Sequence
<220> FEATURE:
<223> OTHER INFORMATION: adalimumab heavy chain

<400> SEQUENCE: 61

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365
```

```
Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
                435                 440                 445

Pro Gly Lys
    450

<210> SEQ ID NO 62
<211> LENGTH: 448
<212> TYPE: PRT
<213> ORGANISM: Artificial Sequence
<220> FEATURE:
<223> OTHER INFORMATION: denosumab heavy chain

<400> SEQUENCE: 62

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gly Ile Thr Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Gly Thr Thr Val Ile Met Ser Trp Phe Asp Pro Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Asn Phe Gly Thr Gln Thr Tyr Thr Cys Asn Val Asp
        195                 200                 205

His Lys Pro Ser Asn Thr Lys Val Asp Lys Thr Val Glu Arg Lys Cys
    210                 215                 220

Cys Val Glu Cys Pro Pro Cys Pro Ala Pro Pro Val Ala Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270
```

```
Glu Val Gln Phe Asn Trp Tyr Val Asp Gly Val Glu Val His Asn Ala
            275                 280                 285

Lys Thr Lys Pro Arg Glu Glu Gln Phe Asn Ser Thr Phe Arg Val Val
        290                 295                 300

Ser Val Leu Thr Val Val His Gln Asp Trp Leu Asn Gly Lys Glu Tyr
305                 310                 315                 320

Lys Cys Lys Val Ser Asn Lys Gly Leu Pro Ala Pro Ile Glu Lys Thr
                325                 330                 335

Ile Ser Lys Thr Lys Gly Gln Pro Arg Glu Pro Gln Val Tyr Thr Leu
                340                 345                 350

Pro Pro Ser Arg Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Met Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
    435                 440                 445

<210> SEQ ID NO 63
<211> LENGTH: 448
<212> TYPE: PRT
<213> ORGANISM: Artificial Sequence
<220> FEATURE:
<223> OTHER INFORMATION: Ipilimumab heavy chain

<400> SEQUENCE: 63

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Thr Met His Trp Val Arg Gln Ala Pro Gly Lys Gly Leu Glu Trp Val
        35                  40                  45

Thr Phe Ile Ser Tyr Asp Gly Asn Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Thr Gly Trp Leu Gly Pro Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190
```

```
Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 64
<211> LENGTH: 451
<212> TYPE: PRT
<213> ORGANISM: Artificial Sequence
<220> FEATURE:
<223> OTHER INFORMATION: tremelimumab heavy chain

<400> SEQUENCE: 64

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Pro Arg Gly Ala Thr Leu Tyr Tyr Tyr Tyr Tyr Gly Met
            100                 105                 110
```

```
Asp Val Trp Gly Gln Gly Thr Thr Val Thr Val Ser Ser Ala Ser Thr
            115                 120                 125

Lys Gly Pro Ser Val Phe Pro Leu Ala Pro Cys Ser Arg Ser Thr Ser
130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Asn Phe Gly Thr Gln Thr Tyr Thr Cys
        195                 200                 205

Asn Val Asp His Lys Pro Ser Asn Thr Lys Val Asp Lys Thr Val Glu
210                 215                 220

Arg Lys Cys Cys Val Glu Cys Pro Pro Cys Pro Ala Pro Pro Val Ala
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Gln Phe Asn Trp Tyr Val Asp Gly Val Glu Val
        275                 280                 285

His Asn Ala Lys Thr Lys Pro Arg Glu Glu Gln Phe Asn Ser Thr Phe
290                 295                 300

Arg Val Val Ser Val Leu Thr Val Val His Gln Asp Trp Leu Asn Gly
305                 310                 315                 320

Lys Glu Tyr Lys Cys Lys Val Ser Asn Lys Gly Leu Pro Ala Pro Ile
                325                 330                 335

Glu Lys Thr Ile Ser Lys Thr Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Met Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 65
<211> LENGTH: 451
<212> TYPE: PRT
<213> ORGANISM: Artificial Sequence
<220> FEATURE:
<223> OTHER INFORMATION: efalizumab heavy chain

<400> SEQUENCE: 65

Glu Val Gln Leu Val Glu Ser Gly Gly Gly Leu Val Gln Pro Gly Gly
1               5                   10                  15
```

-continued

```
Ser Leu Arg Leu Ser Cys Ala Ala Ser Gly Tyr Ser Phe Thr Gly His
         20                  25                  30

Trp Met Asn Trp Val Arg Gln Ala Pro Gly Lys Gly Leu Glu Trp Val
     35                  40                  45

Gly Met Ile His Pro Ser Asp Ser Glu Thr Arg Tyr Asn Gln Lys Phe
 50                  55                  60

Lys Asp Arg Phe Thr Ile Ser Val Asp Lys Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Ile Tyr Phe Tyr Gly Thr Thr Tyr Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
```

-continued

```
                   435                 440                 445

Pro Gly Lys
    450

<210> SEQ ID NO 66
<211> LENGTH: 449
<212> TYPE: PRT
<213> ORGANISM: Artificial Sequence
<220> FEATURE:
<223> OTHER INFORMATION: ustekinumab heavy chain

<400> SEQUENCE: 66

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Thr Tyr
            20                  25                  30

Trp Leu Gly Trp Val Arg Gln Met Pro Gly Lys Gly Leu Asp Trp Ile
        35                  40                  45

Gly Ile Met Ser Pro Val Asp Ser Asp Ile Arg Tyr Ser Pro Ser Phe
    50                  55                  60

Gln Gly Gln Val Thr Met Ser Val Asp Lys Ser Ile Thr Thr Ala Tyr
65                  70                  75                  80

Leu Gln Trp Asn Ser Leu Lys Ala Ser Asp Thr Ala Met Tyr Tyr Cys
                85                  90                  95

Ala Arg Arg Pro Gly Gln Gly Tyr Phe Asp Phe Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
```

| | | 340 | | | 345 | | | 350 | | | |
|---|---|---|---|---|---|---|---|---|---|---|---|
| Leu | Pro | Pro | Ser | Arg | Asp | Glu | Leu | Thr | Lys | Asn | Gln | Val | Ser | Leu | Thr |
| | | 355 | | | | 360 | | | | 365 | |

Cys Leu Val Lys Gly Phe Tyr Pro Ser Asp Ile Ala Val Glu Trp Glu
    370             375             380

Ser Asn Gly Gln Pro Glu Asn Asn Tyr Lys Thr Thr Pro Pro Val Leu
385             390             395             400

Asp Ser Asp Gly Ser Phe Phe Leu Tyr Ser Lys Leu Thr Val Asp Lys
            405             410             415

Ser Arg Trp Gln Gln Gly Asn Val Phe Ser Cys Ser Val Met His Glu
        420             425             430

Ala Leu His Asn His Tyr Thr Gln Lys Ser Leu Ser Leu Ser Pro Gly
        435             440             445

Lys

<210> SEQ ID NO 67
<211> LENGTH: 744
<212> TYPE: DNA
<213> ORGANISM: Artificial Sequence
<220> FEATURE:
<223> OTHER INFORMATION: IgG1 Hinge+ Ipilimumab light chain

<400> SEQUENCE: 67

```
gagcccaaat cttgtgacaa aactcacaca tgcccaccgt gcccagttaa cggcggcggc    60
ggcagcggtc ccctgggtgt gagagcggcc cagccggccg aaattgtgtt gacgcagtct   120
ccaggcaccc tgtctttgtc tccaggggaa agagccaccc tctcctgcag ggccagtcag   180
agtgttggca gcagctactt agcctggtac cagcagaaac ctggccaggc tcccaggctc   240
ctcatctatg gtgcattcag cagggccact ggcatcccag acaggttcag tggcagtggg   300
tctgggacag acttcactct caccatcagc agactggagc ctgaagattt tgcagtgtat   360
tactgtcagc agtatggtag ctcaccgtgg acgttcggcc aagggaccaa ggtggaaatc   420
aaacggactg tggctgcacc atctgtcttc atcttcccgc catctgatga gcagttgaaa   480
tctggaactg cctctgttgt gtgcctgctg aataacttct atcccagaga ggccaaagta   540
cagtggaagg tggataacgc cctccaatcg ggtaactccc aggagagtgt cacagagcag   600
gacagcaagg acagcaccta cagcctcagc agcaccctga cgctgagcaa agcagactac   660
gagaaacaca aactctacgc ctgcgaagtc acccatcagg gcctgagctc gcccgtcaca   720
aagagcttca caggggagag tgc                                            744
```

<210> SEQ ID NO 68
<211> LENGTH: 1440
<212> TYPE: DNA
<213> ORGANISM: Artificial Sequence
<220> FEATURE:
<223> OTHER INFORMATION: IgG1 Hinge+ Ipilimumab heavy chain

<400> SEQUENCE: 68

```
gagcccaaat cttgtgacaa aactcacaca tgcccaccgt gcccaggcgg ccgcggcggc    60
ggcggcagcg tcccctgggt gtgagaagat ctcaggtgc agctggtgga gtctggggga   120
ggcgtggtcc agcctgggag gtccctgaga ctctcctgtg cagcctctgg attcaccttc   180
agtagctata ctatgcactg ggtccgccag gctccaggca aggggctgga gtgggtgaca   240
tttatatcat atgatggaaa caataaatac tacgcagact ccgtgaaggg ccgattcacc   300
atctccagag acaattccaa gaacacgctg tatctgcaaa tgaacagcct gagagctgag   360
```

```
gacacggcta tatattactg tgcgaggacc ggctggctgg ggcccttga ctactgggc      420 cagggaaccc tggtcaccgt ctcctcagcc tccaccaagg gaccatcggt cttccctg      480 gcaccctcct ccaagagcac ctctgggggc acagcggccc tgggctgcct ggtcaaggac    540
tacttccccg aaccggtgac ggtgtcgtgg aactcaggcg ccctgaccag cggcgtgcac    600
accttcccgg ctgtcctaca gtcctcagga ctctactccc tcagcagcgt ggtgaccgtg    660
ccctccagca gcttgggcac ccagacctac atctgcaacg tgaatcacaa gcccagcaac    720
accaaggtcg acaagaaagt tgagcccaaa tcttgtgaca aaactcacac atgcccaccg    780
tgcccagcac ccgaactcct ggggggaccg tcagtcttcc tcttccccc aaaacccaag     840 gacaccctca tgatctcccg gacccctgag gtcacatgcg tggtggtgga cgtgagccac    900
gaagaccctg aggtcaagtt caactggtac gtggacggcg tggaggtgca taatgccaag    960
acaaagccgc gggaggagca gtacaacagc acgtaccgtg tggtcagcgt cctcaccgtc   1020
ctgcaccagg actggctgaa tggcaaggag tacaagtgca aggtctccaa caaagccctc   1080
ccagccccca tcgagaaaac catctccaaa gccaaggggc agccccgaga accacaggtg   1140
tacaccctgc ccccatcccg ggatgagctg accaagaacc aggtcagcct gacctgcctg   1200
gtcaaaggct tctatcccag cgacatcgcc gtggagtggg agagcaatgg gcagccggag   1260
aacaactaca agaccacgcc tcccgtgctg gactccgacg gctccttctt cctctacagc   1320
aagctcaccg tggacaagag caggtggcag caggggaacg tcttctcatg ctccgtgatg   1380
catgaggctc tgcacaacca ctacacgcag aagagcctct ccctgtctcc gggtaaataa   1440
```

<210> SEQ ID NO 69
<211> LENGTH: 735
<212> TYPE: DNA
<213> ORGANISM: Artificial Sequence
<220> FEATURE:
<223> OTHER INFORMATION: IgG2 Hinge+ Ipilimumab light chain

<400> SEQUENCE: 69

```
gagcgcaaat gttgtgtcga gtgcccaccg tgcccagtta acggcggcgg cggcagcggt     60
cccctgggtg tgagagcggc ccagccggcc gaaattgtgt tgacgcagtc tccaggcacc   120
ctgtctttgt ctccagggga aagagccacc ctctcctgca gggccagtca gagtgttggc   180
agcagctact tagcctggta ccagcagaaa cctggccagg ctcccaggct cctcatctat   240
ggtgcattca gcagggccac tggcatccca gacaggttca gtggcagtgg gtctgggaca   300
gacttcactc tcaccatcag cagactggag cctgaagatt ttgcagtgta ttactgtcag   360
cagtatggta gctcaccgtg gacgttcggc caagggacca aggtggaaat caaacggact   420
gtggctgcac catctgtctt catcttcccg ccatctgatg agcagttgaa atctggaact   480
gcctctgttg tgtgcctgct gaataacttc tatcccagag aggccaaagt acagtggaag   540
gtggataacg cctccaaatc gggtaactcc caggagagtg tcacagagca ggacagcaag   600
gacagcacct acagcctcag cagcaccctg acgctgagca agcagactac gagaaacac   660 aaactctacg cctgcgaagt cacccatcag ggcctgagct cgcccgtcac aaagagcttc   720
aacaggggag agtgc                                                    735
```

<210> SEQ ID NO 70
<211> LENGTH: 1431
<212> TYPE: DNA
<213> ORGANISM: Artificial Sequence
<220> FEATURE:

<223> OTHER INFORMATION: IgG2 Hinge+ Ipilimumab heavy chain

<400> SEQUENCE: 70

```
gagcgcaaat gttgtgtcga gtgccaccg tgcccaggcg gccgcggcgg cggcggcagc      60
ggtcccctgg gtgtgagaag atctcaggtg cagctggtgg agtctggggg aggcgtggtc     120
cagcctggga ggtccctgag actctcctgt gcagcctctg gattcacctt cagtagctat    180
actatgcact gggtccgcca ggctccaggc aaggggctgg agtgggtgac atttatatca    240
tatgatggaa acaataaata ctacgcagac tccgtgaagg gccgattcac catctccaga    300
gacaattcca agaacacgct gtatctgcaa atgaacagcc tgagagctga ggacacggct    360
atatattact gtgcgaggac cggctggctg gggccctttg actactgggg ccagggaacc    420
ctggtcaccg tctcctcagc ctccaccaag ggaccatcgg tcttcccccct ggcaccctcc    480
tccaagagca cctctggggg cacagcggcc ctgggctgcc tggtcaagga ctacttcccc    540
gaaccggtga cggtgtcgtg gaactcaggc gccctgacca gcggcgtgca caccttcccg    600
gctgtcctac agtcctcagg actctactcc ctcagcagcg tggtgaccgt gccctccagc    660
agcttgggca cccagaccta catctgcaac gtgaatcaca agcccagcaa caccaaggtc    720
gacaagaaag ttgagcccaa atcttgtgac aaaactcaca catgcccacc gtgcccagca    780
cccgaactcc tggggggacc gtcagtcttc ctcttccccc caaaacccaa ggacaccctc    840
atgatctccc ggacccctga ggtcacatgc gtggtggtgg acgtgagcca cgaagaccct    900
gaggtcaagt tcaactggta cgtggacggc gtggaggtgc ataatgccaa gacaaagccg    960
cgggaggagc agtacaacag cacgtaccgt gtggtcagcg tcctcaccgt cctgcaccag   1020
gactggctga atggcaagga gtacaagtgc aaggtctcca acaaagccct cccagccccc   1080
atcgagaaaa ccatctccaa agccaagggg cagccccgag aaccacaggt gtacaccctg   1140
cccccatccc gggatgagct gaccaagaac caggtcagcc tgacctgcct ggtcaaaggc   1200
ttctatccca gcgacatcgc cgtggagtgg gagagcaatg ggcagccgga gaacaactac   1260
aagaccacgc ctcccgtgct ggactccgac ggctccttct tcctctacag caagctcacc   1320
gtggacaaga gcaggtggca gcaggggaac gtcttctcat gctccgtgat gcatgaggct   1380
ctgcacaacc actacacgca gaagagcctc tccctgtctc cgggtaaata a             1431
```

<210> SEQ ID NO 71
<211> LENGTH: 885
<212> TYPE: DNA
<213> ORGANISM: Artificial Sequence
<220> FEATURE:
<223> OTHER INFORMATION: IgG3 Hinge+ Ipilimumab light chain

<400> SEQUENCE: 71

```
gagctcaaaa ccccacttgg tgacacaact cacacatgcc cacggtgccc agagcccaaa      60
tcttgtgaca cacctccccc gtgcccacgg tgcccagagc ccaaatcttg tgacacacct    120
ccccatgcc cacggtgccc agagcccaaa tcttgtgaca cacctccccc gtgcccaagg    180
tgcccagtta acggcggcgg cggcagcggt cccctgggtg tgagagcggc ccagccggcc    240
gaaattgtgt tgacgcagtc tccaggcacc ctgtctttgt ctccagggga aagagccacc    300
ctctcctgca gggccagtca gagtgttggc agcagctact tagcctggta ccagcagaaa    360
cctggccagg ctcccaggct cctcatctat ggtgcattca gcagggccac tggcatccca    420
gacaggttca gtggcagtgg gtctgggaca gacttcactc tcaccatcag cagactggag    480
cctgaagatt ttgcagtgta ttactgtcag cagtatggta gctcaccgtg gacgttcggc    540
```

```
caagggacca aggtggaaat caaacggact gtggctgcac catctgtctt catcttcccg    600
ccatctgatg agcagttgaa atctggaact gcctctgttg tgtgcctgct gaataacttc    660
tatcccagag aggccaaagt acagtggaag gtggataacg ccctccaatc gggtaactcc    720
caggagagtg tcacagagca ggacagcaag acagcacct acagcctcag cagcaccctg     780
acgctgagca agcagacta cgagaaacac aaactctacg cctgcgaagt cacccatcag     840
ggcctgagct cgcccgtcac aaagagcttc aacaggggag agtgc                    885

<210> SEQ ID NO 72
<211> LENGTH: 1581
<212> TYPE: DNA
<213> ORGANISM: Artificial Sequence
<220> FEATURE:
<223> OTHER INFORMATION: IgG3 Hinge+ Ipilimumab heavy chain

<400> SEQUENCE: 72
gagctcaaaa ccccacttgg tgacacaact cacacatgcc cacggtgccc agagcccaaa     60
tcttgtgaca cacctccccc gtgccacgg tgcccagagc ccaaatcttg tgacacacct    120
cccccatgcc cacggtgccc agagcccaaa tcttgtgaca cacctccccc gtgcccaagg    180
tgcccaggcg gccgcggcgg cggcggcagc ggtcccctgg gtgtgagaag atctcaggtg    240
cagctggtgg agtctggggg aggcgtggtc cagcctggga ggtccctgag actctcctgt    300
gcagcctctg gattcacctt cagtagctat actatgcact gggtccgcca ggctccaggc    360
aaggggctgg agtgggtgac atttatatca tatgatggaa acaataaata ctacgcagac    420
tccgtgaagg gccgattcac catctccaga gacaattcca agaacacgct gtatctgcaa    480
atgaacagcc tgagagctga ggacacggct atatattact gtgcgaggac cggctggctg    540
gggccctttg actactgggg ccagggaacc ctggtcaccg tctcctcagc ctccaccaag    600
ggaccatcgg tcttccccct ggcaccctcc tccaagagca cctctggggg cacagcggcc    660
ctgggctgcc tggtcaagga ctacttcccc gaaccggtga cggtgtcgtg gaactcaggc    720
gccctgacca gcggcgtgca caccttcccg gctgtcctac agtcctcagg actctactcc    780
ctcagcagcg tggtgaccgt gccctccagc agcttgggca cccagaccta catctgcaac    840
gtgaatcaca agcccagcaa caccaaggtc gacaagaaag ttgagcccaa atcttgtgac    900
aaaactcaca catgcccacc gtgcccagca cccgaactcc tggggggacc gtcagtcttc    960
ctcttccccc caaaacccaa ggacaccctc atgatctccc ggacccctga ggtcacatgc   1020
gtggtggtgg acgtgagcca cgaagaccct gaggtcaagt tcaactggta cgtggacggc   1080
gtggaggtgc ataatgccaa gacaaagccg cgggaggagc agtacaacag cacgtaccgt   1140
gtggtcagcg tcctcaccgt cctgcaccag gactggctga atggcaagga gtacaagtgc   1200
aaggtctcca caaagccct cccagccccc atcgagaaaa ccatctccaa agccaagggg   1260
cagccccgag aaccacaggt gtacaccctg cccccatccc gggatgagct gaccaagaac   1320
caggtcagcc tgacctgcct ggtcaaaggc ttctatccca gcgacatcgc cgtggagtgg   1380
gagagcaatg ggcagccgga gaacaactac aagaccacgc ctcccgtgct ggactccgac   1440
ggctccttct tcctctacag caagctcacc gtggacaaga gcaggtggca gcaggggaac   1500
gtcttctcat gctccgtgat gcatgaggct ctgcacaacc actacacgca gaagagcctc   1560
tccctgtctc cgggtaaata a                                             1581

<210> SEQ ID NO 73
```

<211> LENGTH: 735
<212> TYPE: DNA
<213> ORGANISM: Artificial Sequence
<220> FEATURE:
<223> OTHER INFORMATION: IgG4 Hinge+ Ipilimumab light chain

<400> SEQUENCE: 73

```
gagtccaaat atggtccccc atgcccatca tgcccagtta acggcggcgg cggcagcggt      60
cccctgggtg tgagagcggc ccagccggcc gaaattgtgt tgacgcagtc tccaggcacc     120
ctgtctttgt ctccagggga agagccacc ctctcctgca gggccagtca gagtgttggc      180
agcagctact tagcctggta ccagcagaaa cctggccagg ctcccaggct cctcatctat     240
ggtgcattca gcagggccac tggcatccca gacaggttca gtggcagtgg gtctgggaca     300
gacttcactc tcaccatcag cagactggag cctgaagatt ttgcagtgta ttactgtcag     360
cagtatggta gctcaccgtg gacgttcggc caagggacca aggtggaaat caaacggact     420
gtggctgcac catctgtctt catcttcccg ccatctgatg agcagttgaa atctggaact     480
gcctctgttg tgtgcctgct gaataacttc tatcccagag aggccaaagt acagtggaag     540
gtggataacg ccctccaatc gggtaactcc caggagagtg tcacagagca ggacagcaag     600
gacagcacct acagcctcag cagcaccctg acgctgagca agcagactac cgagaaacac     660
aaactctacg cctgcgaagt cacccatcag ggcctgagct cgcccgtcac aaagagcttc     720
aacaggggag agtgc                                                      735
```

<210> SEQ ID NO 74
<211> LENGTH: 1431
<212> TYPE: DNA
<213> ORGANISM: Artificial Sequence
<220> FEATURE:
<223> OTHER INFORMATION: IgG4 Hinge+ Ipilimumab heavy chain

<400> SEQUENCE: 74

```
gagtccaaat atggtccccc atgcccagca tgcccaggcg ccgcggcgg cggcggcagc       60
ggtcccctgg gtgtgagaag atctcaggtg cagctggtgg agtctggggg aggcgtggtc     120
cagcctggga ggtccctgag actctcctgt gcagcctctg gattcacctt cagtagctat     180
actatgcact gggtccgcca ggctccaggc aaggggctgg agtgggtgac atttatatca     240
tatgatggaa acaataaata ctacgcagac tccgtgaagg gccgattcac catctccaga     300
gacaattcca agaacacgct gtatctgcaa atgaacagcc tgagagctga ggacacggct     360
atatattact gtgcgaggac cggctggctg gggcccttg actactgggg ccagggaacc     420
ctggtcaccg tctcctcagc ctccaccaag ggaccatcgg tcttcccct ggcaccctcc      480
tccaagagca cctctggggg cacagcggcc ctgggctgcc tggtcaagga ctacttcccc    540
gaaccggtga cggtgtcgtg gaactcaggc gccctgacca gcggcgtgca caccttcccg    600
gctgtcctac agtcctcagg actctactcc ctcagcagcg tggtgaccgt gccctccagc    660
agcttgggca cccagaccta catctgcaac gtgaatcaca agcccagcaa caccaaggtc    720
gacaagaaag ttgagcccaa atcttgtgac aaaactcaca catgcccacc gtgcccagca    780
cccgaactcc tggggggacc gtcagtcttc ctcttccccc caaaacccaa ggacaccctc    840
atgatctccc ggacccctga ggtcacatgc gtggtggtgg acgtgagcca cgaagaccct    900
gaggtcaagt tcaactggta cgtggacggc gtggaggtgc ataatgccaa gacaaagccg    960
cgggaggagc agtacaacag cacgtaccgt gtggtcagcg tcctcaccgt cctgcaccag   1020
gactggctga atggcaagga gtacaagtgc aaggtctcca acaaagccct cccagccccc   1080
```

| | |
|---|---|
| atcgagaaaa ccatctccaa agccaagggg cagccccgag aaccacaggt gtacaccctg | 1140 |
| cccccatccc gggatgagct gaccaagaac caggtcagcc tgacctgcct ggtcaaaggc | 1200 |
| ttctatccca gcgacatcgc cgtggagtgg gagagcaatg gcagccgga gaacaactac | 1260 |
| aagaccacgc ctcccgtgct ggactccgac ggctccttct tcctctacag caagctcacc | 1320 |
| gtggacaaga gcaggtggca gcaggggaac gtcttctcat gctccgtgat gcatgaggct | 1380 |
| ctgcacaacc actacacgca gaagagcctc tccctgtctc cgggtaaata a | 1431 |

<210> SEQ ID NO 75
<211> LENGTH: 768
<212> TYPE: DNA
<213> ORGANISM: Artificial Sequence
<220> FEATURE:
<223> OTHER INFORMATION: IgA1 Hinge+ Ipilimumab light chain

<400> SEQUENCE: 75

| | |
|---|---|
| ccagttccct caactccacc tacccatct ccctcaactc cacctacccc atctccctca | 60 |
| tgctgccacg ttaacggcgg cggcggcagc ggtcccctgg gtgtgagagc ggcccagccg | 120 |
| gccgaaattg tgttgacgca gtctccaggc accctgtctt tgtctccagg ggaaagagcc | 180 |
| accctctcct gcagggccag tcagagtgtt ggcagcagct acttagcctg gtaccagcag | 240 |
| aaacctggcc aggctcccag gctcctcatc tatggtgcat tcagcagggc cactggcatc | 300 |
| ccagacaggt tcagtggcag tgggtctggg acagacttca ctctcaccat cagcagactg | 360 |
| gagcctgaag attttgcagt gtattactgt cagcagtatg gtagctcacc gtggacgttc | 420 |
| ggccaaggga ccaaggtgga aatcaaacgg actgtggctg caccatctgt cttcatcttc | 480 |
| ccgccatctg atgagcagtt gaaatctgga actgcctctg ttgtgtgcct gctgaataac | 540 |
| ttctatccca gagaggccaa agtacagtgg aaggtggata acgccctcca atcgggtaac | 600 |
| tcccaggaga gtgtcacaga gcaggacagc aaggacagca cctacagcct cagcagcacc | 660 |
| ctgacgctga gcaaagcaga ctacgagaaa cacaaactct acgcctgcga agtcacccat | 720 |
| cagggcctga gctcgcccgt cacaaagagc ttcaacaggg gagagtgc | 768 |

<210> SEQ ID NO 76
<211> LENGTH: 768
<212> TYPE: DNA
<213> ORGANISM: Artificial Sequence
<220> FEATURE:
<223> OTHER INFORMATION: IgA1 Hinge+ Ipilimumab heavy chain

<400> SEQUENCE: 76

| | |
|---|---|
| ccagttccct caactccacc tacccatct ccctcaactc cacctacccc atctccctca | 60 |
| tgctgccacg ttaacggcgg cggcggcagc ggtcccctgg gtgtgagagc ggcccagccg | 120 |
| gccgaaattg tgttgacgca gtctccaggc accctgtctt tgtctccagg ggaaagagcc | 180 |
| accctctcct gcagggccag tcagagtgtt ggcagcagct acttagcctg gtaccagcag | 240 |
| aaacctggcc aggctcccag gctcctcatc tatggtgcat tcagcagggc cactggcatc | 300 |
| ccagacaggt tcagtggcag tgggtctggg acagacttca ctctcaccat cagcagactg | 360 |
| gagcctgaag attttgcagt gtattactgt cagcagtatg gtagctcacc gtggacgttc | 420 |
| ggccaaggga ccaaggtgga aatcaaacgg actgtggctg caccatctgt cttcatcttc | 480 |
| ccgccatctg atgagcagtt gaaatctgga actgcctctg ttgtgtgcct gctgaataac | 540 |
| ttctatccca gagaggccaa agtacagtgg aaggtggata acgccctcca atcgggtaac | 600 |

```
tcccaggaga gtgtcacaga gcaggacagc aaggacagca cctacagcct cagcagcacc    660
ctgacgctga gcaaagcaga ctacgagaaa cacaaactct acgcctgcga agtcacccat    720
cagggcctga gctcgcccgt cacaaagagc ttcaacaggg gagagtgc                 768
```

```
<210> SEQ ID NO 77
<211> LENGTH: 729
<212> TYPE: DNA
<213> ORGANISM: Artificial Sequence
<220> FEATURE:
<223> OTHER INFORMATION: IgA2 Hinge+ Ipilimumab light chain

<400> SEQUENCE: 77
ccagttcccc cacctccccc atgctgccac gttaacggcg gcggcggcag cggtcccctg     60
ggtgtgagag cggcccagcc ggccgaaatt gtgttgacgc agtctccagg caccctgtct    120
ttgtctccag gggaagagc caccctctcc tgcagggcca gtcagagtgt tggcagcagc    180
tacttagcct ggtaccagca gaaacctggc caggctccca ggctcctcat ctatggtgca    240
ttcagcaggg ccactggcat cccagacagg ttcagtggca gtgggtctgg gacagacttc    300
actctcacca tcagcagact ggagcctgaa gattttgcag tgtattactg tcagcagtat    360
ggtagctcac cgtggacgtt cggccaaggg accaaggtgg aaatcaaacg gactgtggct    420
gcaccatctg tcttcatctt cccgccatct gatgagcagt tgaaatctgg aactgcctct    480
gttgtgtgcc tgctgaataa cttctatccc agagaggcca agtacagtg aaggtggat    540 aacgccctcc aatcgggtaa ctcccaggag agtgtcacag agcaggacag caaggacagc    600
acctacagcc tcagcagcac cctgacgctg agcaaagcag actacgagaa acacaaactc    660
tacgcctgcg aagtcaccca tcagggcctg agctcgcccg tcacaaagag cttcaacagg    720
ggagagtgc                                                            729
```

```
<210> SEQ ID NO 78
<211> LENGTH: 729
<212> TYPE: DNA
<213> ORGANISM: Artificial Sequence
<220> FEATURE:
<223> OTHER INFORMATION: IgA2 Hinge+ Ipilimumab heavy chain

<400> SEQUENCE: 78
ccagttcccc cacctccccc atgctgccac gttaacggcg gcggcggcag cggtcccctg     60
ggtgtgagag cggcccagcc ggccgaaatt gtgttgacgc agtctccagg caccctgtct    120
ttgtctccag gggaagagc caccctctcc tgcagggcca gtcagagtgt tggcagcagc    180
tacttagcct ggtaccagca gaaacctggc caggctccca ggctcctcat ctatggtgca    240
ttcagcaggg ccactggcat cccagacagg ttcagtggca gtgggtctgg gacagacttc    300
actctcacca tcagcagact ggagcctgaa gattttgcag tgtattactg tcagcagtat    360
ggtagctcac cgtggacgtt cggccaaggg accaaggtgg aaatcaaacg gactgtggct    420
gcaccatctg tcttcatctt cccgccatct gatgagcagt tgaaatctgg aactgcctct    480
gttgtgtgcc tgctgaataa cttctatccc agagaggcca agtacagtg aaggtggat    540 aacgccctcc aatcgggtaa ctcccaggag agtgtcacag agcaggacag caaggacagc    600
acctacagcc tcagcagcac cctgacgctg agcaaagcag actacgagaa acacaaactc    660
tacgcctgcg aagtcaccca tcagggcctg agctcgcccg tcacaaagag cttcaacagg    720
ggagagtgc                                                            729
```

ANTIBODY LOCKER FOR THE INACTIVATION OF PROTEIN DRUG

CROSS REFERENCE TO RELATED APPLICATIONS

This application is a US national stage of PCT/US2014/039821 filed May 28, 2014, which claims the benefit of U.S Provisional Application No. 61/827,763 filed May 28, 2013.

REFERENCE TO A SEQUENCE LISTING

This application includes an electronic sequence listing in a file named 470914_SEQLST.txt, created on Nov. 23, 2015 and containing 185,849 bytes, which is hereby incorporated by reference.

BACKGROUND OF THE INVENTION

1. Field of the Invention

The present disclosure relates generally to antibody-based molecules useful as therapeutics for treating various medical conditions. More particularly, the disclosed invention relates to hinge antibodies that are selectively activated in a target cell or tissue so as to treat the medical conditions therein.

2. Description of Related Art

Antibody-based therapeutic agents, including monoclonal antibodies, are emerging as one of the major classes of drugs effective in the treatment of various diseases. Of the top 10 drugs by global sales in 2012, five are therapeutic antibodies, including, HUMIRA™, REMICADE™, RITUXAN™, HERCEPTIN™, and AVASTIN™. Said five drugs grossed about $45 billion around the globe, approximating 60% of the global antibody-based therapeutic agent market in that year. The global market is expected to grow continuously as existing products expand their approved usage and new entrants launch into the marketplace.

Although the field continues to advance, many challenges remain in order to bring more efficacious and affordable antibody-based candidates to the market. One problem associated with current antibody-based therapeutic agents is the poor selectivity of site of action. Monoclonal antibodies and soluble fusion proteins are specific for binding to and neutralizing their intended target molecules (such as antigens and cell surface receptors). However, most target molecules are not specific to the disease site; rather, they may be present in cells or tissues other than the disease site. Accordingly, the therapeutic agent may act in these non-disease normal cells or tissues. This off-target action may result in unwanted side effects. Consequently, developing highly targeted antibody-based therapeutic agents is desirable.

One possible scheme of avoiding off-target action and increasing selectivity is to provide a pro-antibody activatable in the target site. For example, U.S. Pat. No. 8,399,219 and U.S. Patent Application Publication No. 2010/0189651 disclose protease activatable antibodies that are modified by a peptide mask or masking moiety. In these documents, the phage display technique is used to screen peptides or moieties capable of inhibiting/reducing the binding of the functional antibody to its binding target. However, the masking moieties obtained by such methods could not be universally applied to all antibodies for they are identified based on their inhibitory ability toward a specific target. Therefore, it is necessary in their approach to develop a masking moiety for each antibody-based therapeutic agent, which is time consuming, expensive, and complicated. Additionally, the introduction of masking moieties runs the risk of inducing unnecessary immuno response to the subject.

A similar approach is described in U.S. Patent Application Publication No. 2010/0189727, which proposed a masking ligand non-covalently bound to an antigen binding site of an antibody so as to inactivate the antibody. In particular, the masking ligand comprises two copies of the epitope of the antigen to which the antibody specifically binds and a cleavable polypeptide cleavable linker joined to each copy of the epitope. Similar to the phage display technique described above, the masking ligand also needs to be specifically designed with respect to each antibody, and hence the development of such inactivated antibody is also time-consuming and with high cost. Further, since the masking ligand has a high affinity toward the therapeutic antibody, there might be certain masking ligands attached to the antibody after the cleavage of the cleavable polypeptide cleavable linker. These residual masking ligands may hinder the therapeutic action of the antibody.

In view of the foregoing, there exists a need in the art for providing next generation therapeutics that are carefully designed and engineered to possess features such as improved selectivity of site of action as well as enhanced efficacy. Further, such design and engineering schemes shall be applicable to a wide variety of antibody-based therapeutic agents, and would not incur unwanted immuno response.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

In one aspect, the present disclosure is directed to a hinge antibody. This antibody-based therapeutic agent is capable of being selectively activated in a target cell or tissue to treat a condition in the target cell or tissue.

According to various embodiments of the present disclosure, the hinge antibody comprises a functional antibody, two inhibitory domains, and four cleavable linkers. The functional antibody is capable of treating the condition in an activated state and comprises two light chains and two heavy chains. Each of the two inhibitory domains consists of two peptide arms interconnected by disulfide bonds. Each inhibitory domain consists of two peptide arms that are interconnected by disulfide bonds. Each of the four cleavable linkers comprises a peptide substrate cleavable by an enzyme that is specifically or highly expressed in the target cell or tissue. Each cleavable linker connects one of the two peptide arms of the two inhibitory domains to the N-terminals of one of the two light chains and two heavy chains of the functional antibody.

According to certain embodiments of the present disclosure, each of the two inhibitory domains is a hinge domain of an immunoglobulin A (IgA), an immunoglobulin D or an immunoglobulin G (IgG), or a fragment of the hinge domain. For example, the inhibitory domain may comprise any of fowling sequences, SEQ ID Nos. 10, 11, 12 and 13 of IgG, 14 and 15 of IgA, and 54 and 55 of IgD.

In optional embodiments, the functional antibody is an anti-TNF-α antibody, anti-RANKL antibody, anti-CTLA-4 antibody, anti-HER2 antibody, anti-EGFR antibody, anti-VEGF antibody, anti-VEGFR2) antibody, anti-IL6R antibody, anti-IL12/23 antibody, anti-CD3 antibody, anti-CD11a antibody, anti-CD20 antibody, anti-CD25 antibody, anti-CD30 antibody, anti-CD33 antibody or anti-CD52 antibody. For example, the amino acid sequence of the light chain of the functional antibody is any of the amino acid sequences of SEQ ID Nos. 1, 2, 3, 4, 5, 6, 7, 8 and 9; while the amino acid sequence of the heavy chain of the functional antibody is any of the amino acid sequences of SEQ ID Nos. 58, 59, 60, 61, 62, 63, 64, 65 and 66.

In certain embodiments, the peptide substrate is cleavable by any of the following enzyme: a matrix metalloproteinase (MMP), a cathepsin (CTS), a caspase (CASP), or a disintegrin and metalloproteinase (ADAM). For example, according to some embodiments, the enzyme is MMP-2 or MMP-9 and each cleavable linker comprises the amino acid sequence of SEQ ID No. 16.

According to some embodiments of the present disclosure, the functional antibody is an anti-TNF-α antibody, which has a light chain having the amino acid sequence of SEQ ID No. 1 and a heavy chain having the amino acid sequence of SEQ ID No. 58, each of the cleavable linkers comprises the amino acid sequence of SEQ ID No. 16; and each of the inhibitory domain comprises the amino acid sequence of SEQ ID No. 10.

In another aspect, the present disclosure is directed to an expression system for producing the hinge antibodies according to the above aspect/embodiments of the present disclosure.

According to various embodiments of the present disclosure, the expression system for producing comprises a first nucleic acid sequence and a second nucleic acid sequence. The first nucleic acid sequence, comprising, from 5' to 3', a first inhibitory domain-encoding region, a first cleavable linker-encoding region and a light chain-encoding region. The first inhibitory domain-encoding region encodes a first peptide arm of an inhibitory domain of any of the above-described hinge antibodies. The first cleavable linker-encoding region encodes a cleavable linker of the above-mentioned hinge antibody, and the cleavable linker is a peptide substrate cleavable by an enzyme that is specifically or highly expressed in the target cell or tissue. The light chain-encoding region encodes a light chain of a functional antibody of the above-mentioned hinge antibody, in which the functional antibody is capable of treating the condition in an activated state. The second nucleic acid sequence, comprising, from 5' to 3', a second inhibitory domain inhibitory domain-encoding region, a second cleavable linker-encoding region and a heavy chain-encoding region. The second inhibitory domain-encoding region encodes a second peptide arm of the inhibitory domain of the hinge antibody. The second cleavable linker-encoding region encodes the cleavable linker of the hinge antibody. The heavy chain-encoding region encodes a heavy chain of the functional antibody of the hinge antibody.

In some optional embodiments of the present disclosure, the first and second nucleic acid sequences can be constructed in a single expression vector. For example, the expression system may further comprise a connecting nucleic acid sequence that connects the first nucleic acid sequence and the second nucleic acid sequence. Non-limiting examples of the connecting nucleic acid sequence include a sequence encoding a Furin-2A polypeptide or an internal ribosome entry site (IRES) sequence.

In the case where the first and second nucleic acid sequences are constructed in a single expression vector, the expression system may further optionally comprise a regulatory sequence operably linked to the first nucleic acid sequence and the second nucleic acid sequence, so as to regulate the translation of the first nucleic acid sequence, the second nucleic acid sequence, and, optionally, the connecting nucleic acid sequence in a host cell. Alternatively, the expression system may comprise at least two separate regulatory sequences operably linked to the first and the second nucleic acid sequences, respectively, to allow the individual regulation of the expression of the first and second nucleic acid sequences.

In some other embodiments, the first and second nucleic acid sequences may be constructed in two separate expression vectors. For instance, the first nucleic acid sequence, together with an operably-linked first regulatory sequence is constructed in a first expression vector, while the second nucleic acid sequence, along with an operably-linked second regulatory sequence is constructed in a second expression vector. The first and second expression vectors may then be delivered into and expressed in a same host cell or different host cells.

According to certain embodiments of the present disclosure, the inhibitory domain is a hinge domain of an immunoglobulin A (IgA), an immunoglobulin D or an immunoglobulin G (IgG), or a fragment of the hinge domain.

According to various embodiments of the present disclosure, the expression system encodes any of the above-mentioned hinge antibodies. For example, when the expression system is embodied by a single construct, the nucleic acid sequence of the construct can be any of SEQ ID Nos. 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 and 50. In the case where expression system is embodied as a two-vector (or two-plasmid) system, the first nucleic acid sequence is any of SEQ ID Nos. 67, 69, 71, 73, 75, and 77; whereas the second nucleic acid sequence is any of SEQ ID Nos. 68, 70, 72, 74, 76 and 78.

In yet another aspect, the present disclosure is directed to a recombinant vector suitable for use in manufacturing the hinge antibodies according to the above aspect/embodiments of the present disclosure.

According to certain embodiments of the present disclosure, the recombinant vector comprises the synthetic nucleic acid molecule according to the above-mentioned aspect/embodiments of the present disclosure, and one or more regulatory sequences operatively linked to the synthetic nucleic acid molecule, so that the vector, under suitable conditions and in an appropriate host cell, is capable of expressing the hinge antibody according to the above-mentioned aspect/embodiments of the present disclosure.

In still another aspect, the present invention is directed to a method for treating a subject; in particular, a subject with cancer or an autoimmune disease.

According to some embodiments of the present invention, the method comprises administering to the subject a therapeutically effective amount of the hinge antibodies according to the above aspect/embodiments of the present disclosure. For example, the hinge antibody may be administered orally, subcutaneously, intravenously, intrathecally or intramuscularly to the subject.

Many of the attendant features and advantages of the present disclosure will becomes better understood with reference to the following detailed description considered in connection with the accompanying drawings.

BRIEF DESCRIPTION OF THE DRAWINGS

The present description will be better understood from the following detailed description read in light of the accompanying drawings, where.

Figure 1:
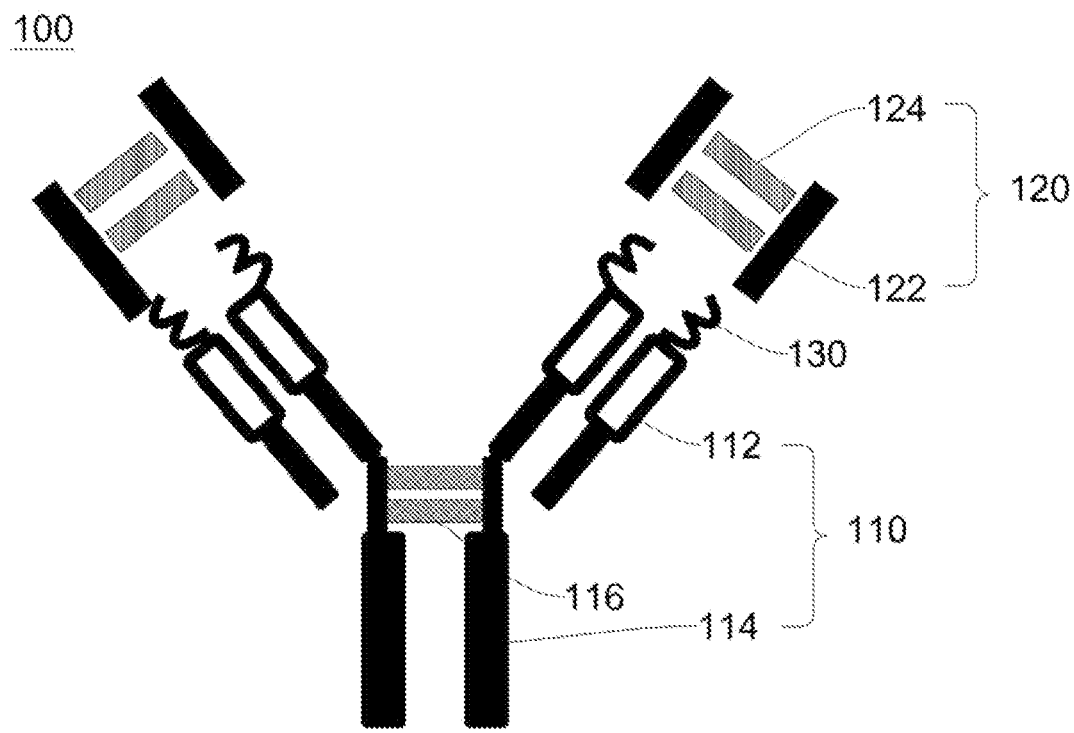
FIG. 1 is a schematic diagram illustrating the structure of a hinge antibody according to certain embodiments of the present disclosure.

In accordance with common practice, the various described features/elements are not drawn to scale but instead are drawn to best illustrate specific features/elements relevant to the present invention. Also, like reference numerals and designations in the various drawings are used to indicate like elements/parts.

DESCRIPTION

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

For convenience, certain terms employed in the specification, examples and appended claims are collected here. Unless defined otherwise, all technical and scientific terms used herein have the same meaning as commonly understood by one of the ordinary skill in the art to which this invention belongs.

Unless otherwise defined herein, scientific and technical terminologies employed in the present disclosure shall have the meanings that are commonly understood and used by one of ordinary skill in the art. Unless otherwise required by context, it will be understood that singular terms shall include plural forms of the same and plural terms shall include the singular. Specifically, as used herein and in the claims, the singular forms "a" and "an" include the plural reference unless the context clearly indicates otherwise.

Also, as used herein and in the claims, the terms "at least one" and "one or more" have the same meaning and include one, two, three, or more.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art.

The term "antibody-based therapeutic agent" is intended to mean a therapeutic agent that inhibits the pharmacological actions of endogenous human proteins or pathogens. Said "therapeutic agent," when present in a therapeutically effective amount, produces a desired therapeutic effect on a subject. For the purpose of the present disclosure, antibody-based therapeutic agents encompass antibodies and fusion proteins that are highly specific for binding to and neutralizing their intended target molecules.

The term "antibody" as used herein includes full-length antibodies and any antigen binding fragment or single chains thereof. The basic functional unit of each antibody is an immunoglobulin monomer which is a Y-shaped molecule consisting of two heavy chains and two light chains interconnected by disulfide bonds. A "functional antibody" encompasses a full-length antibody or one or more fragments of the antibody that maintain the specific binding ability thereof; example of such functional fragments including Fab (antigen-binding fragment), Fv (variable fragment), and F(ab')$_2$, Fab', scFv (single chain fragment variable), and the like. An antibody may be monoclonal or polyclonal and may be of human or non-human origin or a chimeric protein.

Here, a "cleavable linker" is a peptide substrate cleavable by an enzyme. Operatively, the cleaveable linker, upon being cleaved by the enzyme, allows for activation of the present hinge antibody. Preferably, the cleaveable linker is selected so that activation occurs at the desired site of action, which can be a site in or near the target cells (e.g., carcinoma cells) or tissues. For example, the cleaveable linker is a peptide substrate specific for an enzyme that is specifically or highly expressed in the site of action, such that the cleavage rate of the cleavable linker in the target site is greater than that in sites other than the target site.

The term "ligand" means any molecule that specifically binds or reactively associates or complexes with a receptor, substrate, antigenic determinant, or other binding site on a target cell or tissue. Examples of ligands include antibodies and fragments thereof (e.g., a monoclonal antibody or fragment thereof), enzymes (e.g., fibrinolytic enzymes), biologic response modifiers (e.g., interleukins, interferons, erythropoeitin, or colony stimulating factors), peptide hormones, and antigen-binding fragments thereof.

As used herein, the term "nucleic acid" designates single- or double-stranded RNA, mRNA, and DNA including cDNA and genomic DNA. Unless otherwise indicated, a particular nucleic acid sequence also implicitly encompasses conservatively modified variants thereof (e.g., degenerate codon substitutions) and complementary sequences, as well as the sequence explicitly indicated. Also, the left-hand end of single-stranded polynucleotide sequences is the 5' end; the left-hand direction of double-stranded polynucleotide sequences is referred to as the 5' direction, unless specified otherwise.

The terms "polypeptide," "peptide" and "protein" are used interchangeably herein to refer to a polymer of amino acid residues. These terms also encompass the term "antibody." The term "amino acid" refers to naturally occurring and synthetic amino acids, as well as amino acid analogs and amino acid mimetics that function in a manner similar to the naturally occurring amino acids. In the polypeptide notation used herein, the left-hand direction is the amino (N)-terminal direction and the right-hand direction is the carboxyl (C)-terminal direction, in accordance with standard usage and convention.

Throughout the present disclosure, the term "synthetic" nucleic acid or amino acid means a nucleic acid or amino acid sequence that is not found in nature. It is intended that synthetic sequences designed by the method be included in the invention in any form, e.g., paper or computer readable, and physically created nucleic acids or polypeptides. Physically created nucleic acids and polypeptides of the invention are part of the invention, whether derived directly from the designed sequence, or copies of such sequences (e.g., made by PCR, plasmid replication, chemical synthesis, and the like). The term "synthetic nucleic acid" can include, for example, nucleic acid sequences derived or designed from wholly artificial amino acid sequences, or nucleic acid sequences with single or multiple nucleotide changes as compared to the naturally occurring sequence, those created by random or directed mutagenesis, chemical synthesis, DNA shuffling methods, DNA reassembly methods, or by any means known to one of skill in the art. Such alterations can be done without changing the amino acid sequence encoded by the nucleic acid sequence, or can modify the amino acid sequence to leave a desired function of the encoded protein unaltered or enhanced.

As used herein, the term "vector" refers to composition of matter (e.g., phage, plasmid, viral vectors as well as artificial chromosomes, such as bacterial or yeast artificial chromosomes) used to transmit genetic material into a host cell. A vector may be composed of either DNA or RNA. The vector may be introduced into a host cell by various techniques well known in the art. The regulatory sequence of a vector is a nucleic acid sequence required for expression of a target gene product operably linked thereto. The term "operatively linked" as used herein means that the regulatory nucleic acid and the nucleic acid of interest are linked so that the expression of the said nucleic acid of interest can be governed by the said regulatory nucleic acid, i.e. the regulatory nucleic acid sequence shall be functionally linked to the said nucleic acid sequence to be expressed. Accordingly, the regulatory nucleic acid sequence and, the nucleic acid sequence to be expressed may be physically linked to each other, e.g., by inserting the regulatory nucleic acid sequence at the 5'end of the nucleic acid sequence to be expressed. Alternatively, the regulatory nucleic acid sequence and the nucleic acid to be expressed may be merely in physical proximity so that the regulatory nucleic acid sequence is capable of governing the expression of at least one nucleic acid sequence of interest. The regulatory nucleic acid sequence and the nucleic acid to be expressed are, preferably, separated by not more than 500 bp, 300 bp, 100 bp, 80 bp, 60 bp, 40 bp, 20 bp, 10 bp or 5 bp.

The term "treating" as used herein refers to the application or administration of the present hinge antibody to a subject, who has a medical condition, a symptom of the condition, a disease or disorder secondary to the condition, or a predisposition toward the condition, with the purpose to partially or completely alleviate, ameliorate, relieve, delay onset of, inhibit progression of, reduce severity of, and/or reduce incidence of one or more symptoms or features of a particular disease, disorder, and/or condition. Generally, a "treatment" includes not just the improvement of symptoms or decrease of markers of the disease, but also a cessation or slowing of progress or worsening of a symptom that would be expected in absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, and remission (whether partial or total), whether detectable or undetectable.

The term "effective amount" as used herein refers to the quantity of a component which is sufficient to yield a desired therapeutic response. A therapeutically effective amount is also one in which any toxic or detrimental effects of the compound or composition are outweighed by the therapeutically beneficial effects. The specific effective or sufficient amount will vary with such factors as the particular condition being treated, the physical condition of the patient (e.g., the patient's body mass, age, or gender), the type of mammal or animal being treated, the duration of the treatment, the nature of concurrent therapy (if any), and the specific formulations employed and the structure of the compounds or its derivatives. Effective amount may be expressed, for example, in grams, milligrams or micrograms or as milligrams per kilogram of body weight (mg/kg).

The term "subject" refers to a mammal including the human species that is treatable with the hinge antibody and/or methods of the present invention. The term "subject" is intended to refer to both the male and female gender unless one gender is specifically indicated.

The present invention is directed to hinge antibodies that are selectively activatable in a target cell or tissue. Methods and composition of matters (e.g., nucleic acid sequences and vectors) for preparing the present hinge antibodies, the pharmaceutical compositions comprising the hinge antibodies, as well treating methods using the same, also fall within the scope of the present invention.

Figure 2:
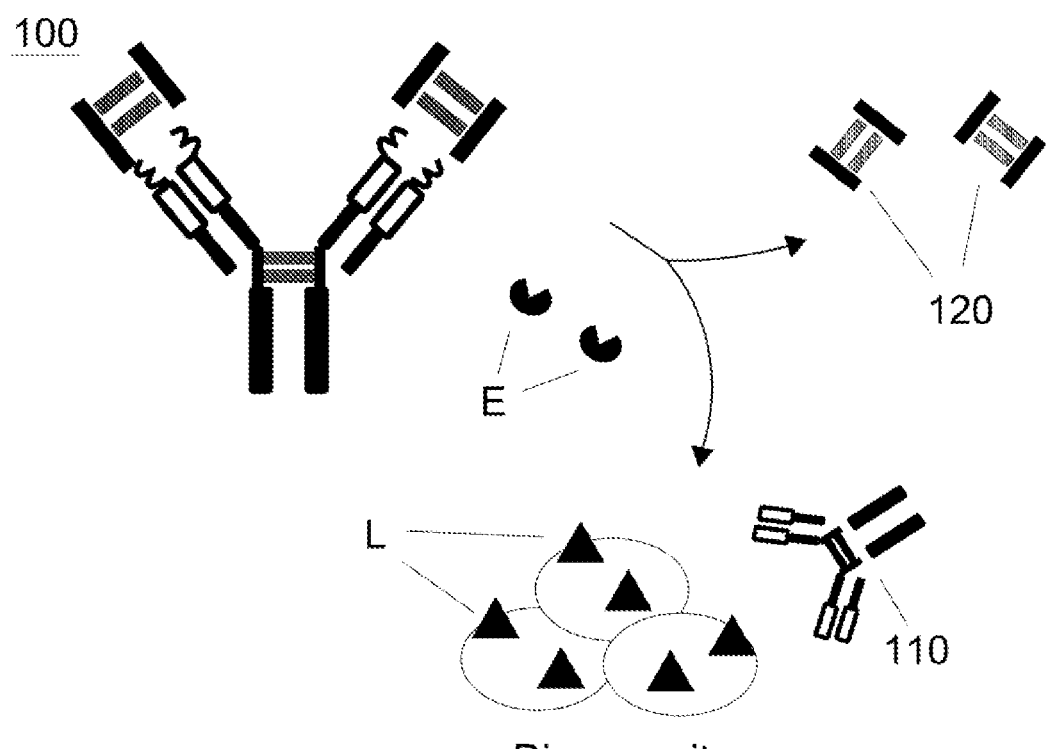
FIG. 2 is a schematic diagram illustrating the design scheme of the hinge antibody according to embodiments of the present disclosure.

FIG. 1 is a schematic diagram illustrating the general structure of the hinge antibody 100 according to certain embodiments of the present invention, and FIG. 2 is a schematic diagram illustrating the design scheme and action mechanism of the hinge antibody 100. As illustrated in FIG. 1, the hinge antibody 100 comprises a functional antibody 110, two inhibitory domains 120, and four cleavable linkers 130 connecting the inhibitory domains 120 to the functional antibody 110. Referring to FIG. 2, in the original, uncleaved form, the binding ability of said hinge antibody 100 toward its target ligand (L) is substantially inhibited (inactivated). Once the hinge antibody 100 is administered to a subject and reaches the target site, an enzyme (E) that is specifically or highly expressed in the target site would cleave the hinge antibody 100 at the cleavable linkers 130. This enzymatic cleavage of the hinge antibody 100 removes the inhibitory domains 120 from the hinge antibody 100 and results in a functional antibody 110 with the binding affinity to the ligand (L). Therefore, the therapeutic effect of the functional antibody 110 can be restored at the disease site.

Referring back to FIG. 1, the functional antibody 110 is a full-length antibody or comprises one or more functional fragment of an antibody for treating a condition in an activated state. In structure, the functional antibody 110 comprises two light chains 112 and two heavy chains 114 connected by disulfide bonds. In particular, the two heavy chains 114 are connected by one or more disulfide bonds (116) in a hinge region.

Preferably, the functional antibody 110 is therapeutic antibody for treating one or more conditions in a subject. The functional antibody 110 could be the full-length therapeutic antibody, or a functional fragment thereof. Non-limiting examples of the functional antibody 110 include: anti-tumor necrosis factor-alpha (anti-TNF-α) antibody (e.g., infliximab, adalimumab, certolizumab pegol and golimumab), anti-receptor activator of NFκb ligand (anti-RANKL) antibody (e.g., denosumab), anti-cytotoxic T lymphocyte-associated antigen-4 (anti-CTLA-4) antibody (e.g., tremelimumab and ipilimumab), anti-human epidermal growth factor receptor (anti-HER2) antibody (e.g., pertuzumab, trastuzumab and trastuzumab emtansine), anti-epidermal growth factor receptor (anti-EGFR) antibody (e.g., panitumumab, cetuximab, zalutumumab and necitumumab), anti-vascular endothelial cell growth factor (anti-VEGF) antibody (e.g., bevacizumab and ranibizumab), anti-vascular endothelial cell growth factor receptor 2 (anti-VEGFR2) antibody (e.g., ramucirumab), anti-interleukin 6 receptor (anti-IL6R) antibody (e.g., Regeneron and Tocilizumab), anti-interleukin 12/23 (anti-IL12/23) antibody (e.g., ustekinumab and briakinumab), anti-cluster of differentiation 3 (anti-CD3) antibody (e.g., otelixizumab, teplizumab and muromonab-CD3), anti-CD11a antibody (e.g., efalizumab), anti-CD20 antibody (e.g., obinutuzumab, ofatumumab, tositumomab-i131, ibritumomab tiuxetan and rituximab), anti-CD25 (also known as anti-IL2R) antibody (e.g., basiliximab and daclizumab), anti-CD30 antibody (e.g., brentuximab vedotin), anti-CD33 antibody (e.g., gemtuzumab ozogamicin) and anti-CD52 antibody (e.g., alemtuzumab). It should be noted that this is not an exhaustive list of the therapeutic antibodies suitable for use as the functional antibody 110 described herein; rather, other antibodies having the structure described above are equally applicable to the present invention.

Diseases or medical conditions treatable by one or more of the above-mentioned therapeutic antibodies include, but are not limited to, advanced melanoma (e.g., by ipilimumab), bone loss (e.g., by denosumab), breast cancer (e.g., by trastuzumab, trastuzumab emtansine, pertuzumab or ramucirumab), chronic lymphocytic leukemia (e.g., by obinutuzumab or ofatumumab), colorectal cancer (e.g., by panitumumab, cetuximab or bevacizumab), Crohn disease (e.g., by infliximab or certolizumab pegol), gastric or gastroesophageal junction adenocarcinoma (e.g., by ramucirumab), head and neck cancer (e.g., by zalutumumab), hepatocellular carcinoma (e.g., by ramucirumab), Hodgkin lymphoma (e.g., by brentuximab vedotin), macular degeneration (e.g., by ranibizumab), metastatic melanoma (e.g., by tremelimumab), myeloid leukemia (e.g., by gemtuzumab ozogamicin or alemtuzumab), non-Hodgkin lymphoma (e.g., by ositumomab-i131, ibritumomab tiuxetan or rituximab), non-small cell lung cancer (e.g., by necitumumab), psoriasis (e.g., by efalizumab), plaque psoriasis (e.g., by ustekinumab or briakinumab), reversal or prevention of kidney transplant rejection (e.g., by muromonab-cd3, basiliximab or daclizumab), rheumatoid arthritis (e.g., by tocilizumab, golimumab or adalimumab) and type 1 diabetes mellitus (e.g., by otelixizumab or teplizumab).

In certain embodiments, the functional antibody 110 is an anti-TNF-α antibody having the amino acid sequence of SEQ ID No. 1 (i.e., infliximab light chain) and the amino acid sequence of SEQ ID No. 58 (i.e., infliximab heavy chain), an anti-EGFR antibody having the amino acid sequence of SEQ ID No. 2 (i.e., panitumumab light chain) and the amino acid sequence of SEQ ID No. 59 (i.e., panitumumab heavy chain), an anti-HER2 antibody having the amino acid sequence of SEQ ID No. 3 (i.e., trastuzumab light chain) and the amino acid sequence of SEQ ID No. 60 (i.e., trastuzumab heavy chain), an anti-TNF-α antibody having the amino acid sequence of SEQ ID No. 4 (i.e., adalimumab light chain) and the amino acid sequence of SEQ ID No. 61 (i.e., adalimumab heavy chain), an anti-RANKL antibody having the amino acid sequence of SEQ ID No. 5 (i.e., denosumab light chain) and the amino acid sequence of SEQ ID No. 62 (i.e., denosumab heavy chain), an anti-CTLA-4 antibody having the amino acid sequence of SEQ ID No. 6 (i.e., ipilimumab light chain) and the amino acid sequence of SEQ ID No. 63 (i.e., ipilimumab heavy chain), an anti-CTLA-4 antibody having the amino acid sequence of SEQ ID No. 7 (i.e., tremelimumab (a.k.a., ticilimumab) light chain) and the amino acid sequence of SEQ ID No. tremelimumab (i.e., tremelimumab heavy chain), an anti-CD11a antibody of SEQ ID No. 8 (i.e., efalizumab light chain) and the amino acid sequence of SEQ ID No. 65 (i.e., efalizumab heavy chain), or an anti-IL12/23 antibody of SEQ ID No. 9 (i.e., ustekinumab light chain) and the amino acid sequence of SEQ ID No. 66 (i.e., ustekinumab heavy chain).

As illustrated in FIG. 1, each inhibitory domain 120 consists of two peptide arms 122. In the illustrated example, the two peptides arms 122 are interconnected by disulfide bonds 124; however, the present invention is not limited thereto. According to certain embodiments of the present disclosure, the inhibitory domain 120 is, or comprises a portion of, a hinge domain of an immunoglobulin; such as immunoglobulin A (IgA), immunoglobulin D (IgD), or immunoglobulin G (IgG). According to various embodiments of the present disclosure, the IgA is IgA1 (SEQ ID No. 14) or IgA2 (SEQ ID No. 15), the IgG is IgG1 (SEQ ID No. 10), IgG2 (SEQ ID No. 11), IgG3 (SEQ ID No. 12) or IgG4 (SEQ ID No. 13); whereas the IgD is IgD1 (SEQ ID No. 54) or IgD2 (SEQ ID No. 55).

The hinge structures of the inhibitory domains 120, upon being attached to the functional antibody 110, sterically mask the ligand-binding site of the functional antibody 110. Hence, the hinge antibody 100, in the uncleaved state, exhibits little, if any, interaction with the intended ligand. According to working examples provided herein, in the uncleaved state, the binding ability of the functional antibody 110 toward its ligand is reduced by at least about 70%, 71%, 72%, 73%, 74%, 75%, 76%, 77%, 78%, 79%, 80%, 81%, 82%, 83%, 84, 85%, 86%, 87%, 88%, 89%, 90%, 91%, 92%, 93%, 94%, 95%, 96%, 97%, 98%, 99% and even 100.

According to various embodiments of the present disclosure, when the functional antibody 110 is coupled to the inhibitory domain 120 and in the presence of its intended ligand, there is no binding or substantially no binding of the functional antibody 110 to its ligand, or no more than 0.001%, 0.02%, 0.1%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, or 30% binding of the functional antibody 110 to its ligand, as compared to the binding of the functional antibody 110 not coupled to the inhibitory domain 120.

Another advantageous of the present inhibitory domain 120 lies in its versatile applicability. As could be appreciated, the inhibitory domain 120 is not designed based on its specific interaction with the functional antibody 110 and/or the intended ligand of the functional antibody 110, and hence, the inhibitory activity is not dependent on the functional antibody 110. Also, most therapeutic antibodies share common and similar backbones, facilitating the attachment of the inhibitory domain 120 thereto.

In addition to the desirable inhibitory activity and versatile applicability, the present inhibitory domain 120 is also advantageous in that it is derived from the hinge region of the immunoglobulin. Hence, unlike the exogenous masking ligands in the prior art, the present inhibitory domain 120 will not elicit unwanted immuno response in the subject.

The inhibitory domain 120 is attached to the functional antibody through the cleavable linker 130. Specifically, each of the four cleavable linkers 130 connects one of the two peptide arms 122 of the two inhibitory domains 120 to the N-terminals one of the two light chains 112 and two heavy chains 114 of the functional antibody 110. The cleavable linker 130 comprises a peptide substrate cleavable by an enzyme that is specifically or highly expressed in the target cell or tissue (such as lesion site of the subject) such that the hinge antibody 100 is activatable in the target cell or tissue.

As discussed above, the attachment of the inhibitory domains 120 with the functional antibody 110 results in the inhibition of the binding of the functional antibody 110 toward its intended ligand. However, once the enzyme digests the cleavable linker 130, the inhibitory domains 120 detach from the hinge antibody 100, thereby restoring the binding ability of the functional antibody 110.

In certain embodiments, the peptide substrate is cleavable by any of the following enzyme: a matrix metalloproteinase (e.g., MMP-1, MMP-2, MMP-3, MMP-7, MMP-8, MMP-9, MMP-13 and MMP-14), a cathepsin (e.g., CTS A, CTS B, CTS D, CTS E and CTS K), a caspase (e.g., CASP-1, CASP-2, CASP-3, CASP-4, CASP-5, CASP-6, CASP-7, CASP-7, CASP-9, CASP-10, CASP-11, CASP-12, CASP-13 and CASP-14), or a disintegrin and metalloproteinase (e.g., ADAM-10, ADAM-12, ADAM-17, ADAM-TS and ADAM-TS5).

Matrix metalloproteinases (MMPs) are a family of zinc-dependent endopeptidases that degrade matrix proteins. MMPs include collagenases, gelatinases, matrilysins, enamelysins, metalloelastases, stromelysins and other structural protein and receptor lysins. MMPs involve in the breakdown of extracellular matrix in normal physiological processes, such as embryonic development and reproduction, as well as in disease processes, such as arthritis and metastasis.

For example, both MMP-2 (also known as gelatinase A or 72 kDa type IV collagenase) and MMP-9 (also known as gelatinase B or 92 kDa type IV collagenase) play a role in the inflammatory response. Accordingly, these proteins are highly expressed in the inflammatory site than in other cells/tissues of the subject. Also, increased expression of MMP-2 or MMP-9 is also positively associated with tumor progression including invasion, metastasis, growth and angiogenesis. Therefore, a peptide substrate for these proteins is suitable for use as the cleavable linker 130 such that the hinge antibody 100 is activatable in the inflammatory site or cancerous site. Further, since the expression level of the MMP-2/MMP-9 in the in cells/tissues other than the lesion site is relatively low, the activation of the present hinge antibody 100 in these cells/tissues is rare, as compared with that in the lesion site. Accordingly, the present hinge antibody 100 is operable to treat the disease with an improved selectivity of site of action.

According to some embodiments, each cleavable linker 130 comprises the amino acid sequence of Gly-Pro-Leu-Gly-Val-Arg (GPLGVR; SEQ ID No. 16) which is a peptide substrate for MMP-2 or MMP-9. Non-limiting examples of peptide substrates for MMP-2/MMP-9 include: Pro-Leu-Gly-Met-Trp-Ser-Arg (PLGMWSR; SEQ ID No. 51), Pro-Leu-Gly-Leu-Trp-Ala-(d)-Arg (PLGLWA-(d)-R; SEQ ID No. 52), and Pro-Gln-Gly-Ile-Ala-Gly-Gln-(d)-Arg (PQ-GIAGQ-(d)-R; SEQ ID No. 53).

By activatable it is meant that the hinge antibody 100 exhibits a first binding affinity to a ligand of interest when in an uncleaved or non-activated state, and a second binding affinity to the same ligand when in a cleaved or activated state, wherein the second binding affinity is greater than the first binding affinity. For example, the binding affinity of the activated functional antibody 110 towards its intended ligand can be at least 2, 3, 4, 5, 10, 15, 20, 25, 30, 35, 35, 40, 45, 50, 60, 70, 80, 90, 100, 150, 200, 250, 300, 350, 400, 450, 500, 600, 700, 800, 900 or even 1,000 times greater than the binding affinity of the uncleaved hinge antibody 100 towards the same ligand.

Since the cleavable linker 130 is selected based on its specificity to an enzyme that is highly expressed in the target site, it is appreciated that the activation of the hinge antibody 100 will mostly take place in the target site. This high selectivity of the site of action, in conjunction with the eminent inhibitory activity in the uncleaved state, substantially avoids off-target action of the functional antibody 110.

Figure 3:
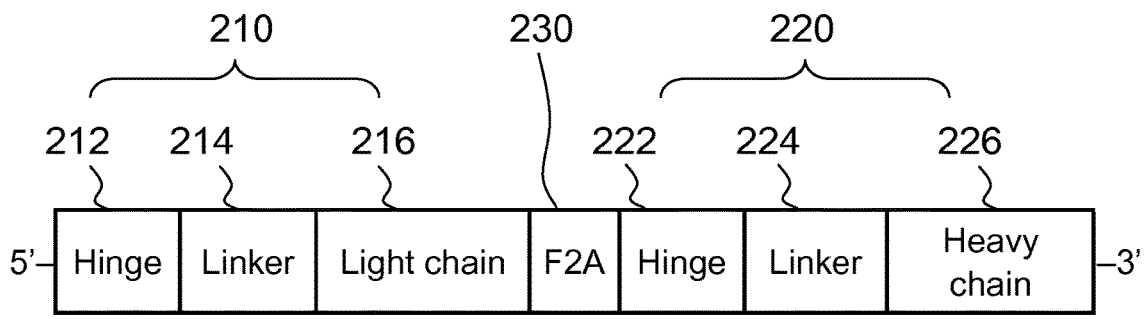
FIG. 3 is a schematic diagram illustrating a nucleic acid molecule encoding a hinge antibody according to certain embodiments of the present disclosure.

The present disclosure is further advantageous in that the detached inhibitory domain 120 does not interfere with the binding between the activated functional antibody 110 and the intended ligand of the functional antibody 110. Accordingly, the binding affinity of the functional antibody 110 is substantially restored, once the hinge antibody 100 is activated through the cleavage of the cleavable linker 130. For example, after the hinge antibody 100 contacts the enzyme (e.g., MMP-2) that is highly expressed in the target site for a specified time, there is at least 70%, 71%, 72%, 73%, 74%, 75%, 76%, 77%, 78%, 79%, 80%, 81%, 82%, 83%, 84, 85%, 86%, 87%, 88%, 89%, 90%, 91%, 92%, 93%, 94%, 95%, 96%, 97%, 98%, 99% or 100% binding of the activated functional antibody 110 to its intended ligand, as compared with the binding of the functional antibody 110 not coupled to the inhibitory domain 120.

In certain embodiments of the present disclosure, the functional antibody 110 is an anti-TNF-α antibody and comprises the amino acid sequence of SEQ ID No. 1, each of the cleavable linkers 130 comprises the amino acid sequence of SEQ ID No. 14; and each of the inhibitory domains 120 comprises the amino acid sequence of SEQ ID No. 8.

The hinge antibody according to embodiments of the present disclosure can be synthetically generated or can be recombinantly expressed and purified.

For example, the hinge antibody can be synthesized by commonly used methods such as t-BOC or FMOC protection of alpha-amino groups. Both methods involve stepwise syntheses whereby a single amino acid is added at each step starting from the C terminus of the peptide. Hinge antibodies of the invention can also be synthesized by the well-known solid phase peptide synthesis methods.

For the recombinant production of the hinge antibody, vector constructs or nucleic acid molecules encoding for the present hinge antibody is provided. Various vector constructs which are capable of expression in prokaryotic or eukaryotic cells are known in the art. Expression vector constructs are generally selected so as to be compatible with the host cell in which they are to be used. In certain embodiments, the vector encodes the light and heavy chain of the functional antibody, the inhibitory domain and the cleavable linkers.

FIG. 3 is a diagram of an exemplary nucleic acid molecule 200 according to certain embodiments of the present disclosure. In suitable conditions, the nucleic acid molecule 200 could be translated, and the expressed polynucleotide(s) is/are then modified and/or assembled into the present hinge antibody, e.g., the hinge antibody 100 illustrated above. FIG. 3 is a schematic diagram illustrating a nucleic acid molecule encoding a hinge antibody according to certain embodiments of the present disclosure; e.g., the hinge antibody 100 illustrated above.

In certain embodiments, the synthetic nucleic acid molecule 200 comprises a first nucleic acid sequence 210, a second nucleic acid sequence 220 and a connecting nucleic acid sequence 230. The first nucleic acid sequence 210 comprises from 5' to 3', a first inhibitory domain-encoding region 212, a first cleavable linker-encoding region 214 and a light chain-encoding region 216. The first inhibitory domain-encoding region 212 encodes a first peptide arm (such as one peptide arm 122 illustrated in FIG. 1) of an inhibitory domain (such as the inhibitory domain 120 of FIG. 1) of the present hinge antibody. In certain embodiments, the inhibitory domain can be a hinge domain of IgA, IgD, or IgG, or a fragment of the hinge domain. The first cleavable linker-encoding region 214 encodes a peptide substrate (e.g., the cleavable linker 130 of FIG. 1) cleavable by an enzyme that is specifically or highly expressed in the target cell or tissue. The light chain-encoding region 216 encodes a light chain (e.g., light chain 102 of FIG. 1) of a functional antibody capable of treating the condition in an activated state. The second nucleic acid sequence 220 comprises, from 5' to 3', a second inhibitory domain-encoding region 222, a second cleavable linker-encoding region 224 and a heavy chain-encoding region 226. The second inhibitory domain-encoding region 222 encodes a peptide second arm (such as another peptide arm 122 of FIG. 1) of the inhibitory domain (e.g., the inhibitory domain 120 of FIG. 1). The second cleavable linker-encoding region 224 encodes the same peptide substrate (e.g., the cleavable linker 130 illustrated in FIG. 1). The heavy chain-encoding region 226 encodes a heavy chain (such as, heavy chain 104) of the functional antibody.

The connecting nucleic acid sequence 230 is used to connect the first nucleic acid sequence 210 and the second nucleic acid sequence 220 to form the single nucleic acid molecule 200.

In optional embodiments, the first nucleic acid sequence 210 and the second nucleic acid sequence 220 are combined in a single opening reading frame, and the translated product, upon secretion, is modified to generate the assembled hinge antibody. For example, as illustrated in FIG. 3, a Furin-2A-encoding sequence 230 is provided between the first and the second nucleic acids 210 and 220. Alternatively, an IRES sequence (not shown) can be used to join the first nucleic acid sequence 210 and the second nucleic acid sequence 220 such that these two nucleic acid sequences are separately translated into two polypeptides.

According to various embodiments of the present disclosure, the synthetic nucleic acid molecule 200 comprises a nucleotide sequence encoding for any of the above-mentioned hinge antibodies and equivalents thereof. For example, the synthetic nucleic acid molecule may have a nucleotide sequence of any of SEQ ID Nos. 17-50. According to other embodiments of the present disclosure, the first and second nucleic acid sequences are constructed in two separate vectors, in which the first nucleic acid sequence is any of SEQ ID Nos. 67, 69, 71, 73, 75, and 77, whereas the second nucleic acid sequence is any of SEQ ID Nos. 68, 70, 72, 74, 76 and 78.

Also, SEQ ID No. 56 is an exemplary sequence of the nucleic acid molecule encoding the IgD1 hinge domains having the sequence of SEQ ID No. 54; while SEQ ID No. 57 is an exemplary sequence of the nucleic acid molecule encoding the IgD2 hinge domains having the sequence of SEQ ID No. 55.

Vectors for expressing the above synthetic nucleic acid molecule 200 are generally constructed by joining the synthetic nucleic acid molecules 200 with one or more regulatory sequences such that the transcription and/or the translation of the synthetic nucleic acid molecule 200 are under the control of the regulatory sequence(s). Non-limiting examples of the regulatory sequences include promoters, enhancers, terminators, operators, repressors, and inducers.

Expression vector constructs generally also provide a transcriptional and translational initiation region as may be needed or desired, which may be inducible or constitutive, where the coding region is operably linked under the transcriptional control of the transcriptional initiation region, and a transcriptional and translational termination region. These control regions may be native to the species from which the nucleic acid is obtained, or may be derived from exogenous sources. Expression vector constructs, can also include a selectable marker operative in the host to facilitate, for example, growth of host cells containing the construct of interest. Such selectable marker genes can provide a phenotypic trait for selection of transformed host cells such as dihydrofolate reductase or neomycin resistance for eukaryotic cell culture.

As could be appreciated, when the first nucleic acid sequence 210 and the second nucleic acid sequence 220 are constructed in a single reading frame, the expression vector may comprise one regulatory sequence operably linked to the first nucleic acid sequence and the second nucleic acid sequence. On the other hand, when the first nucleic acid sequence 210 and the second nucleic acid sequence 220 are arranged in different reading frames, the expression vector may have at least two regulatory sequences operably linked to the first nucleic acid sequence and the second nucleic acid sequence, respectively.

In other embodiments, the first nucleic acid and the second nucleic are not constructed in a single vector; rather, they are provided in two separate vectors each having its own transcriptional and translational initiation region, selectable marker, and/or regulatory sequence.

The hinge antibody of the present invention is useful for the treatment of disease(s) or medical condition(s) which is/are treatable by the functional antibody of the hinge antibody. Diseases or medical conditions treatable by antibody-based therapy are mostly cancer or autoimmune diseases.

To treat a subject suffering from such diseases, the present hinge antibody or a pharmaceutical composition comprising the same is administered to the subject in a therapeutically effective amount. Accordingly, the pharmaceutical composition and treating method also fall within the scope of the present invention.

In addition to the hinge antibody, said pharmaceutical composition further comprises a pharmaceutically-acceptable carrier. The phrase "pharmaceutically-acceptable carrier" as used herein means a pharmaceutically acceptable material, composition or vehicle, such as a liquid or solid filler, diluent, excipient, solvent or encapsulating material, involved in carrying or transporting the active agents (e.g., the hinge antibody) from one organ, or portion of the body, to another organ, or portion of the body. The carrier must be "acceptable" in the sense of being compatible with the other ingredients of the formulation, and is selected to minimize any degradation of the active agent and to minimize any adverse side effects in the subject. The pharmaceutical composition may further comprises one or more pharmaceutically-acceptable additives, including binders, flavorings, buffering agents, thickening agents, coloring agents, anti-oxidants, diluents, stabilizers, buffers, emulsifiers, dispersing agents, suspending agents, antiseptics and the like.

The choice of a pharmaceutically-acceptable carrier to be used in conjunction with the present hinge antibody peptide is basically determined by the way the composition is to be administered. The pharmaceutical composition of the present invention may be administered subcutaneous, intravenous, intrathecal or intramuscular injection.

Injectables for administration can be prepared in sterile aqueous or non-aqueous solutions, suspensions, and emulsions. Examples of non-aqueous solvents include, but are not limited to, propylene glycol, polyethylene glycol, vegetable oils such as olive oil, and injectable organic esters such as ethyl oleate. Illustrative examples of aqueous carriers include water, alcoholic/aqueous solutions, emulsions or suspensions, including saline and buffered media. Common parenteral vehicles include sodium chloride solution, Ringer's dextrose, dextrose and sodium chloride, lactated Ringer's, or fixed oils; whereas intravenous vehicles often include fluid and nutrient replenishers, electrolyte replenishers (such as those based on Ringer's dextrose), and the like.

As could be appreciated, since the present hinge antibody is cleaved and activated in the lesion site and remains uncleaved and inactive in other regions of the body, the present treating method is advantageous in that it reduced, or even eliminates, the risks of systemic side effect resulted from off-target action. Also, the present treating method improves the efficacy of the existing therapeutic antibodies.

The following Examples are provided to elucidate certain aspects of the present invention and to aid those of skilled in the art in practicing this invention. These Examples are in no way to be considered to limit the scope of the invention in any manner. Without further elaboration, it is believed that one skilled in the art can, based on the description herein, utilize the present invention to its fullest extent. All publications cited herein are hereby incorporated by reference in their entirety.

EXAMPLE 1

Materials and Methods 1.1 Cell Lines and Cell Cultures

The human embryonic kidney cell line expressing SV40 T antigen (293T), human breast cancer cell line (SKBr3), human colorectal carcinoma cell line (SW480), Huh 7 were purchased from American Type Culture Collection. The cells were cultured in Dulbecco's Modified Eagle's Medium (DMEM; Sigma-Aldrich) supplemented with 10% Cosmic calf serum (CCS; Sigma-Aldrich), 1% (10,000 µ/ml) penicillin, and 1% (10,000 µ/ml) streptomycin (Invitrogen) at 37° C. in a humidified atmosphere of 5% $CO_2$. Phoenix amphitropic retroviral packaging cells (Source) were cultured in DMEM/Nutrient F-12 Ham (DMEM/F12) medium supplemented with 10% fetal bovine serum (FBS; Sigma-Aldrich), 1% (10,000 µ/ml) penicillin, and 1% (10,000 µ/ml) streptomycin at 37° C. in a humidified atmosphere of 5% $CO_2$. For passage purpose, 293T cells and Phoenix cells were treated with 1× Versene (EDTA) solution for 3 to 5 minutes, whereas SKBr3, SW480 and Huh7 cells are treated with trypsin for 3 to 5 minutes. Cells were then sub-cultured in different concentrations as required by the experimentation need.

1.2 Biochemical Reagents

TransIT®-LT1 Transfection Reagent was purchased from Mirus Bio LLC. Opti-MEM and EDTA were purchased from Invitrogen. Bovine serum albumin (BSA) and Type IV MMP2 (Gelatinase A) were purchased from Sigma-Aldrich. HRP-Goat-α human-IgG Fcγ antibody and FITC-Goat-α human-IgGAM Fcγ were purchased from Jackson.

1.3 Plasmid Constructs

To construct the nucleic acid construct encoding the anti-TNF-α antibody, infliximab, a Furin-2A peptide-encoding nucleic acid construct was used to join the light chain-encoding sequence and heavy chain-encoding sequence in a single plasmid. Then, polymerase chain reaction (PCR) was performed to introduce NheI, HindIII and SfiI to the N-terminal of the light chain, XhoI to the C-terminal of the light chain, BgIII to the N-terminal of the heavy chain, and ClaI and AscI to the C-terminal of the heavy chain. Next, the IgG1 hinge-encoding and MMP2 substrate-encoding sequences were introduced to the upstream of the light and heavy chain-encoding sequences to produce a nucleic acid construct (SEQ ID No. 43) encoding IgG1 hinge/MMP2/infliximab. Same protocol was applied to the construction of nucleic acid constructs encoding other antibodies or hinge/MMP2/antibodies, such as IgG1 hinge/MMP2/ipilimumab (SEQ ID No. 17), IgG2 hinge/MMP2/ipilimumab (SEQ ID No. 18), IgG3 hinge/MMP2/ipilimumab (SEQ ID No. 19), IgG4 hinge/MMP2/ipilimumab (SEQ ID No. 20), IgA1 hinge/MMP2/ipilimumab (SEQ ID No. 21), IgA2 hinge/MMP2/ipilimumab (SEQ ID No. 22), IgG1 hinge/MMP2/tremelimumab (SEQ ID No. 23), IgG2 hinge/MMP2/tremelimumab (SEQ ID No. 24), IgG3 hinge/MMP2/tremelimumab (SEQ ID No. 25), IgG4 hinge/MMP2/tremelimumab (SEQ ID No. 26), IgA1 hinge/MMP2/tremelimumab (SEQ ID No. 27), IgA2 hinge/MMP2/tremelimumab (SEQ ID No. 28), IgG1 hinge/MMP2/adalimumab (SEQ ID No. 29), IgG2 hinge/MMP2/adalimumab (SEQ ID No. 30), IgG3 hinge/MMP2/adalimumab (SEQ ID No. 31), IgG4 hinge/MMP2/adalimumab (SEQ ID No. 32), IgA1 hinge/MMP2/adalimumab (SEQ ID No. 33), IgA2 hinge/MMP2/adalimumab (SEQ ID No. 34), IgG1 hinge/MMP2/panitumumab (SEQ ID No. 35), IgG1 hinge/MMP2/denosumab (SEQ ID No. 36), IgG2 hinge/MMP2/denosumab (SEQ ID No. 37), IgG3 hinge/MMP2/denosumab (SEQ ID No. 38), IgG4 hinge/MMP2/denosumab (SEQ ID No. 39), IgA1 hinge/MMP2/denosumab (SEQ ID No. 40), IgA2 hinge/MMP2/denosumab (SEQ ID No. 41), IgG1 hinge/MMP2/efalizumab (SEQ ID No. 42), IgG2 hinge/MMP2/infliximab (SEQ ID No. 44), IgG3 hinge/MMP2/infliximab (SEQ ID No. 45), IgG4 hinge/MMP2/infliximab (SEQ ID No. 46), IgA1 hinge/MMP2/infliximab (SEQ ID No. 47), IgA2 hinge/MMP2/infliximab (SEQ ID No. 48), IgG1 hinge/MMP2/ustekinumab (SEQ ID No. 49), and IgG1 hinge/MMP2/trastuzumab (SEQ ID No. 50).

The constructs encoding infliximab and hinge/MMP2/infliximab were then respectively introduced into the pLKO AS3w.puro plasmids containing extended viral packaging signal (Ψ+), puromycin-resistant gene (Puror) and ampicillin-resistant gene (Ampr) to produce expression vectors (infliximab-pLKO plasmid and hinge/MMP2/infliximab-pLKO plasmid). Plasmids for expressing other nucleic acid constructs were prepared with the same protocol.

1.4 Lentivirus Transfection

Phoenix cells were treated with Versene, and detached cells (1.5×10⁶ cells/well) were seed in a 6-well CellBind plate. After incubation in the incubator at 37° C. for 24 hours, the original cell culture liquid was removed and replenished with half-volume of DMEM supplemented with 10% FBS culture liquid.

1.25 μg hinge/MMP2/infliximab-pLKO plasmid (in 125 μL Opti-MEM plus 1.125 μg pCMV-ΔR8.91 plasmid and 0.125 μg pMD.G plasmid) was slowly added into a reaction solution containing 7.5 μL TransIT® reagent in 125 μL Opti-MEM. The mixture was left stand for 30 minutes and then slowly added into the 6-well plate and shook in the incubator at 37° C. for 16 hours before the addition of half-volume fresh medium (DMEM/F12+10% FBS+1% BSA+1× p/s). In the next 3 days, 2 ml of supernatant was collected every 24 hours and replenished with 2 ml of fresh medium. The collected supernatant was centrifuged with 1250 rpm for 5 minutes, and the supernatant was stored at 4° C. in the refrigerator.

For virus condensation, the refrigerated supernatant was rewarmed at room temperature, and filtered into a protein centrifugal filter tube and then centrifuged with 3500 rpm at 4° C. until the volume reduced to 1.5 ml. The condensate was aliquoted and stored at −80° C. until use.

To transfect 293T cells, 293T cells were seed in a 6-well plate by 4×10⁴/well. The next day, cells were transfected at 10-20% confluence. The original medium was first removed, and the infection medium (1 ml of growth medium (DMEM+10% CCS+1% P/S)+150 μl virus liquid+8 μg/ml polybrene) was added along the wall. After shaking for 24 hours, the medium was removed and replenished with a new growth medium and transfected 293T cells were screed by puromycene (3-5 μg/ml). The growth medium was refreshed every 2 days with the puromycene screening for 2 weeks. The cells were then harvested and subject to Western blotting to detect whether the cells stably expresses the hinge/MMP2/infliximab. 293T cells stably expressing infliximab was prepared by the same protocol.

1.5 Antibody Purification

Transfected 293T cells were seed in a culture plate (15 cm) and cultured with DMEM supplemented with 10% CCS and 1% penicillin-streptomycin until about 80-90% confluence. The original growth medium was removed and the plate was washed with 10 ml PBS to remove the serum. The cells were then cultured with 15 ml serum-free DMEM medium for two days, and the supernatant was collected and centrifuged with 3500 rpm at 4° C. for 10 minutes. The supernatant was then collected and stored at −80° C. until use.

For purification, 135 ml of the frozen supernatant was rewarmed using a 37° C. water bath. The supernatant was then condensed by 30 folds using a protein centrifugal filter tube. The antibodies were purified using the Protein A sepharose purification system, and the bounded antibodies were eluted with 0.1 M glycine elute buffer (pH 3.0). The pH value of the eluate was adjusted to 7.4 using 1M Tris-base (pH 8.0) and 6N HCL. The samples were then collected to a dialysis membrane (Regenerated cellulose tubular membrane T4, MWCO: 12000-14000, CelluSep) and dialyzed twice with 1×PBS (pH 7.4) for 1 to 2 hours. The product was confirmed by 10% SDS-PAGE separation followed by dyeing with Comassie Brilliant Blue for 10 minutes.

1.6 MMP2 Substrate Cleavage

Hinge/MMP2/infliximab (5 μg in 36 μl of PBS) was reacted with MMP2 (0.8 μg in 4 μl of DMEM, final concentration 20 μg/ml) on ice for 0, 1, 5, 10, 30, or 60 minutes. Anti-TNF-α antibody (infliximab) was used as control. The reaction mixture was then added into a reducing dye and boiled at 100° C. for 10 minutes to terminate the activity of MMP2. The cleavage of MMP2 substrate was confirmed by 10% SDS-PAGE and Western blotting.

For Western blot analysis, reducing dye was added into the collected cells and supernatant in a 6:1 (v/v) ratio and boiled at 100° C. for 10 minutes. Then, proteins were separated by 10% SDS-PAGE, and transferred to a nitrocellulose paper, which was blocked with 5% skim milk at 4° C. overnight. HRP-Goat anti-human IgG Fcγ antibody (0.4 μg/ml in 5% skim milk) was used to identify the antibody.

1.7 Enzyme-linked Immunosorbent Assay

The activities of hinge/MMP2/antibodies were determined by antigen-based ELISA or cell-based ELIA.

(A) Plate Coating

To determine the activity of hinge/MMP2/infliximab or hinge/MMP2/adalimumab, TNF-α (0.3 μg/ml) was diluted in a coating buffer (100 mM Na₂CO₃, Ph 8.0) and coated onto ELISA (Nunc-Maxisorp) by incubated at 37° C. for 2 hours. As to hinge/MMP2/denosumab, the 96 well plate was coated with 50 μl/well of RANKL (0.3 μg/ml) in coating buffer (100 mM Na₂CO₃, pH 8.0) for 2 hours at 37° C. To determine the activity of hinge/MMP2/Ipilimumab or hinge/MMP2/tremelimumab, the 96 well plate were coated with 50 μl/well of CTLA4 (0.3 μg/ml) in coating buffer (100 mM Na₂CO₃, pH 8.0) for 2 hours at 37° C.

For blocking, 200 μl of 5% skim milk was added into each well of a 96-well plate and stored at 4° C. refrigerator overnight.

The activities of hinge/MMP2/anti-EGFR antibody and hinge/MMP2/anti-HER2 antibody were determined by cell-based ELISA. Briefly, EGFR-positive SW480 cells or HER2-positive SKBr3 cells were seed on a 96-well plate by 10⁵ cells/well using 200 μl of growth medium (DMEM+10% CCS+1% P/S), and incubated at 37° C. overnight.

(B) MMP2 Treatment

20 μL of ice-cold MMP2 enzyme (200 μg/ml in serum free DMEM) was diluted by 10-fold and was reacted with 180 μL of transfected 293T cells supernatant on ice for 0, 1, 10, 30, 60 or 90 minutes before the reaction was terminated by addition of 20 μl of CCS.

(C) Antibody Activity

Next day, after removing the original culture liquid from the blocked 96-well plate, the plate was washed with 0.05% PBST (200 μl/well) once and PBS (200 μl/well once) (or washed with DMEM (200 μl/well) once in the case of cell-based ELIA), and the liquid in the wells was removed. The MMP2-treated hinge/MMP2/antibody (50 μl/well) was then added in duplicate (or triplicate in the case of cell-based ELIA) and reacted for 2 hours at room temperature. After the reaction, the sampled was pipetted from the well and the plate was washed with 0.05% PBST (200 μl/well) trice and PBS (200 μl/well) once (or washed with DMEM (200 μl/well) trice in the case of cell-based ELISA) to remove free antibodies. Next, 1 μg/ml of HRP-goat anti-human IgG Fcγ antibody in 2% skim milk in PBS (or in DMEM+2% CCS in the case of cell-based ELIA) was distributed to 96-well plate by 50 μl/well and reacted for 1 hour at room temperature. After pipetting the HRP-goat anti-human IgG Fcγ antibody from the well, the plate was washes with 0.05% PBST (or DMEM in the case of cell-based ELIA) (200 μl/well) trice and PBS (200 μl/well) once.

Activity of the MMP2-treated hinge/MMP2/antibody was determined by oxidation of 2,2'-azino-bis(3-ethylbenzthiazoline-6-sulfonic acid) (ABTS) as a substrate. The reaction mixture containing ABTS and 30% H₂O₂(ABTS:

H₂O₂=3000:1) was added to the plate by 150 μl/well. Oxidation of ABTS was followed by an absorbance increase at 405 nm. The enzyme activity was evaluated by the absorbance intensity. The activity of other antibodies was determined with the same protocol.

1.8 Neutralization of TNF-α Signal by Hinge/MMP2/Infliximab

Huh 7 cells were treated with Trypsin (0.05%), and detached cells (7×10⁴ cells/well) were seed in a 24-well CellBind plate. After incubation in the incubator at 37° C. for 24 hours, the original cell culture liquid was removed and replenished with DMEM supplemented with 10% FBS culture liquid.

0.5 μg NF-kB-Luc reporter plasmid was added into a reaction solution containing 1.5 μL TransIT®-LT1 Transfection Reagent in 30 μL serum-free DMEM. The mixture was slowly added into the 24-well plate and shook in the incubator at 37° C. for 24 hours.

Twenty four hours after transfection, cells were treated with either of: (1) medium (as the negative control); (2) 20 ng TNF-α (as the positive control); (3) 20 ng TNF-α and 100 mg/ml infliximab; (4) 20 ng TNF-α, 100 mg/ml infliximab and 20 mg/ml MMP2; (5) 20 ng TNF-α and 100 mg/ml IgG1 hinge/MMP2/infliximab; and (6) 20 ng TNF-α, 100 mg/ml IgG1 hinge/MMP2/infliximab and 20 mg/ml MMP2. Twenty four hours after the treatment, Steady-Glo and PBS were added into the 96 well, and luciferase reader was used to detect the luciferase activity.

1.9 Animal Experimentations

All animals used in working examples of the present disclosure were housed in an animal room under temperature control (24-25° C.) and 12:12 light-dark cycle. Standard laboratory chow and tap water were available ad libitum. The experiments procedures were approved by the Kaohsiung Medical University Review Board (Kaohsiung City, Taiwan, R.O.C.) and were performed in compliance with national animal welfare regulations.

EXAMPLE 2

Purification of Hinge/MMP2/Infliximab

Figure 4:
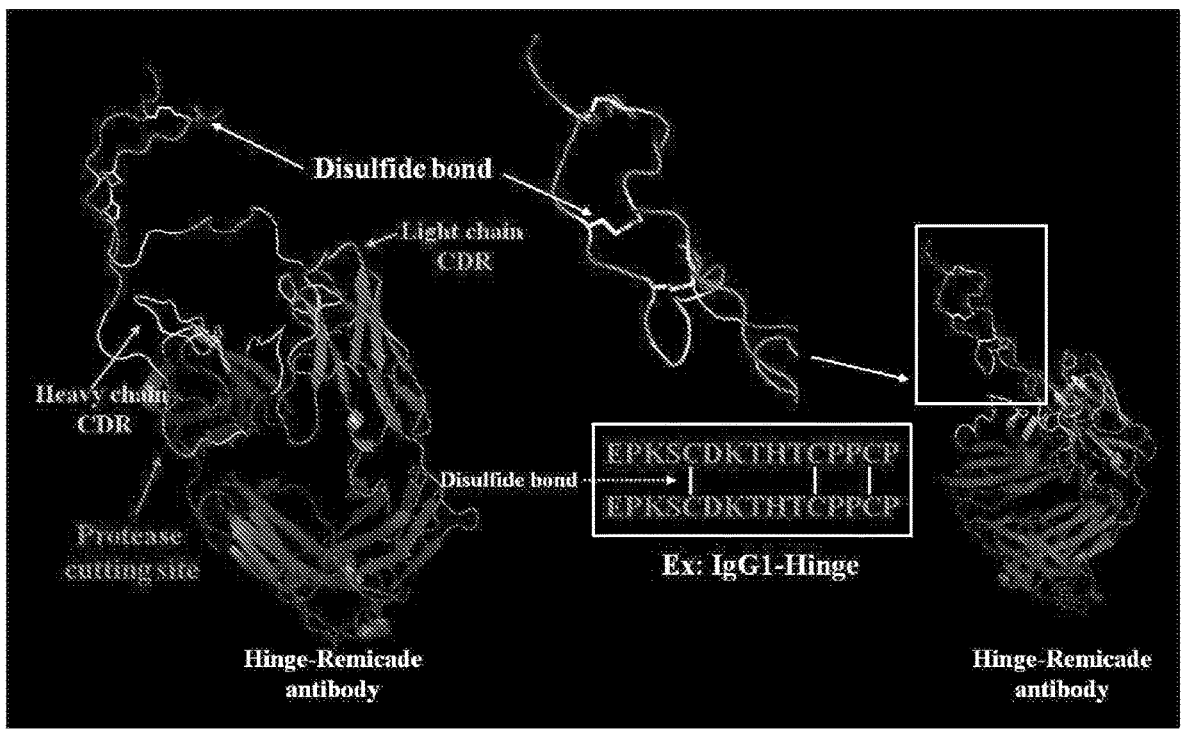
FIG. 4 is a schematic diagram illustrating the overall structure of a hinge antibody according to one embodiment of the present disclosure.

The three-dimensional structure of the Hinge/MMP2/infliximab was generated via computer simulation. Referring to FIG. 4, the IgG1 hinge domain consists of two peptide interconnected by disulfide bonds, and the complimentarity determining region (CDR) of the light chain and heavy chain of infliximab is blocked by the swinging inhibitory domain derived from the IgG1 hinge domain.

Figure 5:
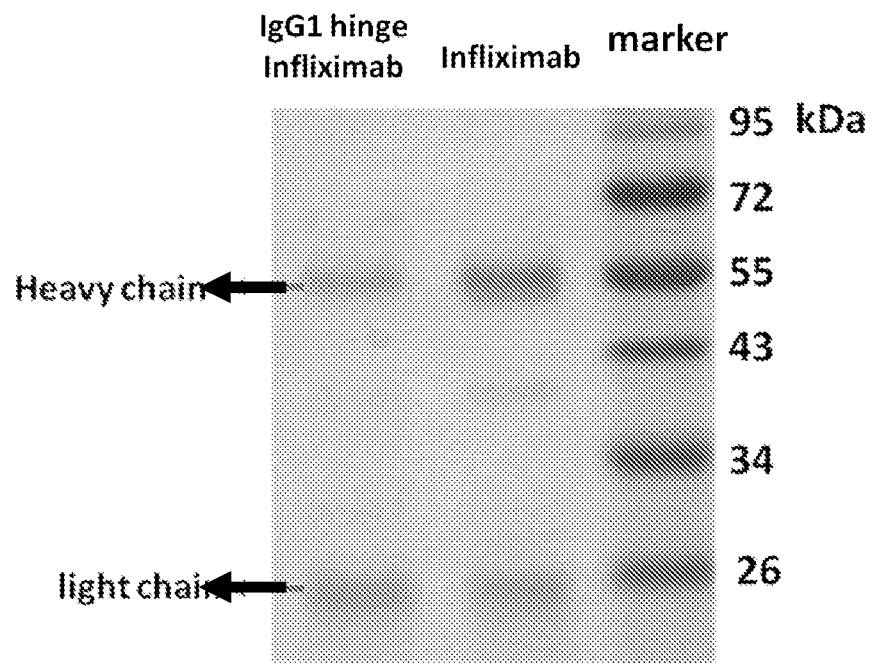
FIG. 5 is a photograph of an SDS PAGE gel according to one working example of the present disclosure.

Purification was carried out as described in Example 1.5, above, and the purified products were confirmed by SDS PAGE (FIG. 5). The purified product is confirmed to be 55 kDa IgG1 hinge/MMP2/infliximab heavy chain (left), the size of which is similar to infliximab (middle). The purity of the products from Lane 4 is about 85%.

EXAMPLE 3

Removal of Inhibitory Domain from Hinge/MMP2/Infliximab Via MMP2 Treatment

Figure 6:
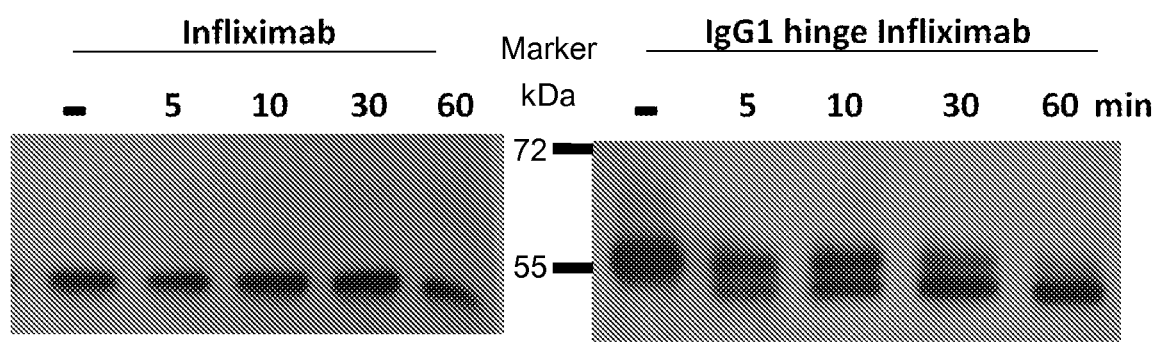
FIG. 6 is a photograph of two SDS PAGE gels according to one working example of the present disclosure.
Figure 7:
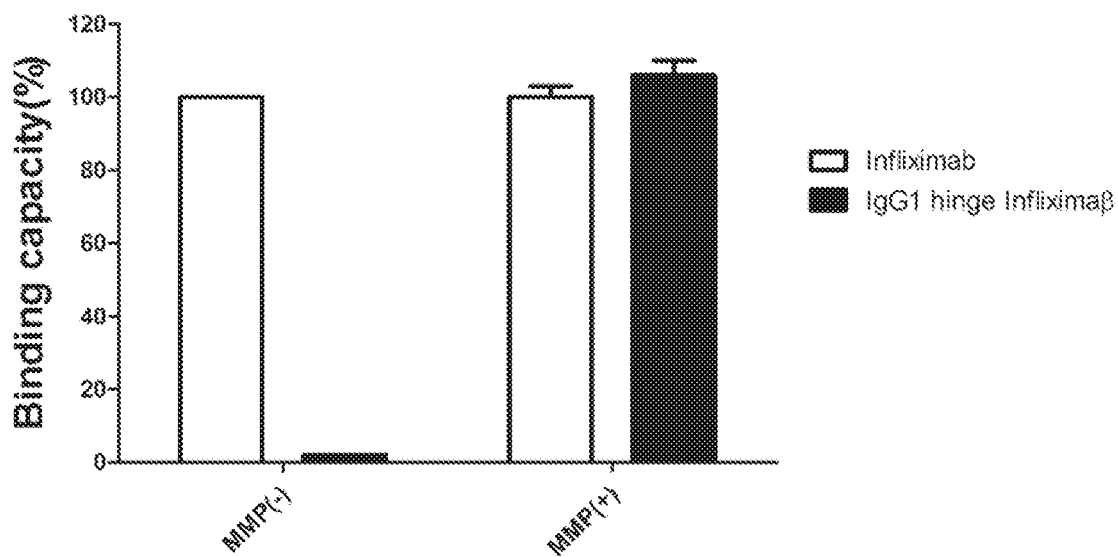
FIG. 7 is a bar graph illustrating the binding capacity of various antibodies according to one working example of the present disclosure.
Figure 8:
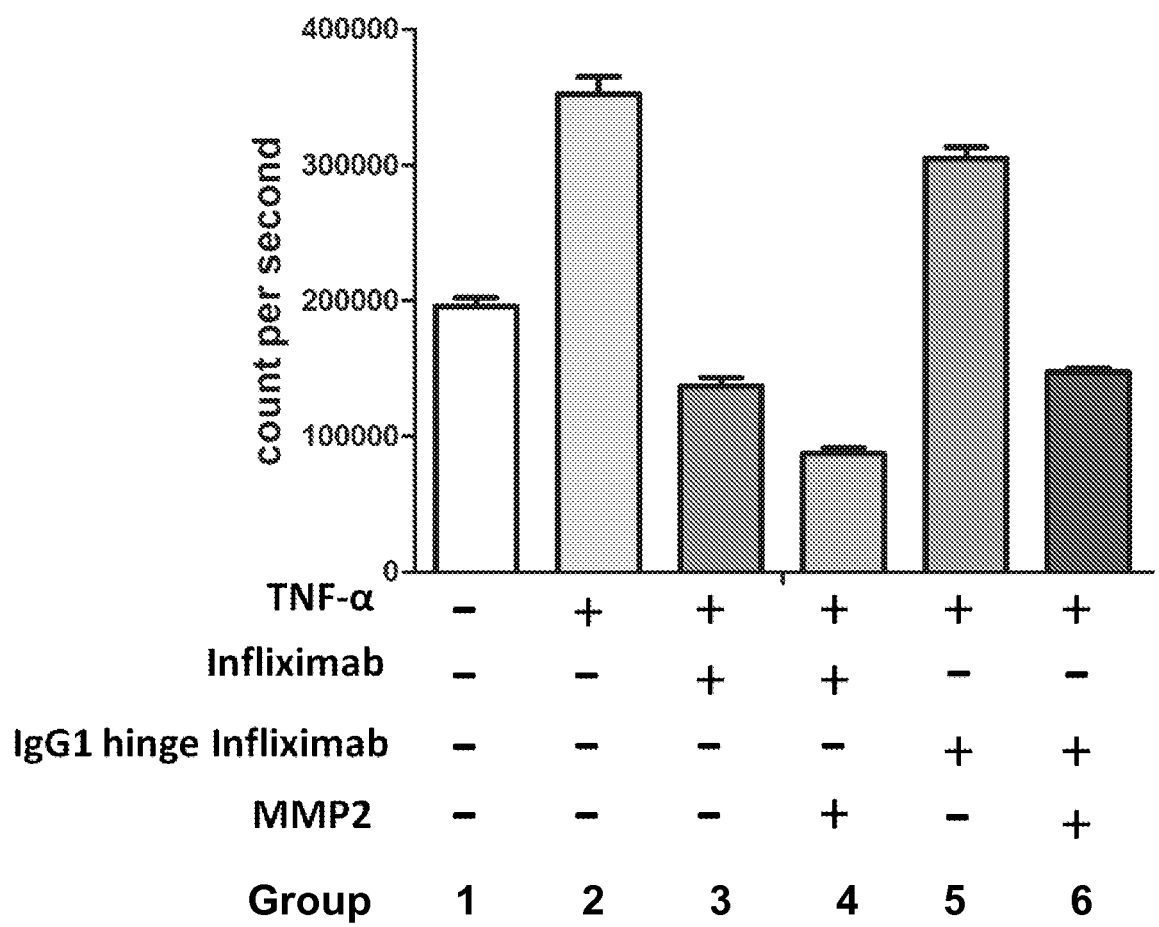
FIG. 8 is a bar graph illustrating the TNF-α signal according to one working example of the present disclosure.

IgG1 Hinge/MMP2/infliximab or infliximab (anti-TNF-α antibody) were treated with MMP2 (20 μg/ml) as described in Example 1.6. The result of Western blot analysis, as provided in FIG. 6, demonstrates that the molecular weight of infliximab (about 53.5 kDa) is constant before and after the MMP2 treatment. On the other hand, before the MMP2 treatment, the molecular weight of IgG1 hinge/MMP2/infliximab is about 55 kDa, whereas after the MMP2 treatment, the intensity of the band of 55 kDa product gradually reduces while the intensity of the band of about 53.5 kDa increases with time. This result indicates that the inhibitory domain of the present hinge antibody can be removed from the functional antibody domain by the MMP2 treatment.

EXAMPLE 4

Inhibition and Restoration of Antigen-Binding Activity of Hinge/MMP2/Anti-TNF-α Antibody Antigen-binding activities of the purified hinge/MMP2/infliximab before and after MMP2 treatment (Example 1.6) were measured by ELISA, and results are summarized in FIG. 7. In this analysis, the binding capacity of the anti-TNF-α antibody to TNF-α was set to 100%, and relative percent of hinge/MMP2/infliximab was calculated accordingly.

ELISA results indicate that the binding capacity of the hinge/MMP2/infliximab to TNF-α is about 0.5% before being treated with MMP2, confirming that the attachment of the inhibitory domain substantially inhibits the binding capability of the functional anti-TNF-α domain by 99.5%. The data also reveal the MMP2 treatment of one hour is sufficient to activate the hinge/MMP2/infliximab for the binding capacity thereof is revived to about 110%. Two hours after the MMP2 treatment, the binding capacity of the activated hinge/MMP2/infliximab is further elevated to about 120%, as compared with Infliximab.

EXAMPLE 5

Neutralization of TNF-α Signal by Hinge/MMP2/Infliximab

Example 1.8 was performed to understand whether the IgG1 hinge/MMP2/infliximab is still capable of neutralizing the TNF-α signal after the MMP2 treatment. Results, as summarized in FIG. 8 indicate that the conventional infliximab, whether with (group 4) or without (group 3) the MMP2 treatment, can effectively block the TNF-α signal, as compared with the positive control (group 2). In contrast, the IgG1 hinge/MMP2/infliximab without the MMP2 treatment (group 5) cannot substantially neutralize the TNF-α signal, whereas the MMP2-treated IgG1 hinge/MMP2/infliximab (group 6) effectively reduces the TNF-α signal. These results demonstrate that the inhibitory domain proposed by the present invention is effective in blocking the binding between the functional antibody domain and the intended ligand of the functional antibody. Moreover, this experiment also establishes that the functionality of the functional domain of the present hinge antibody could be restored by the MMP2 treatment.

EXAMPLE 6

Inhibition and Restoration of Antigen-Binding Activity of Various Hinge/MMP2/Antibodies The antigen-binding capacities of various hinge/MMP2/anti-HER2 antibodies before and after MMP2 treatment are summarized in FIG. 9, FIG. 10 and Table 1.

TABLE 1

| Antibody (INN) | Hinge domain | Inhibition (%) |
|---|---|---|
| Anti-TNF-α (Infliximab) | IgG1 | 99.5 |
| | IgG2 | 94 |
| | IgG3 | 99 |

TABLE 1-continued

| Antibody (INN) | Hinge domain | Inhibition (%) |
|---|---|---|
| | IgG4 | 68.5 |
| | IgA1 | 97.5 |
| | IgA2 | 76.5 |
| Anti-EGFR (Panitumumab) | IgG1 | 89 |
| Anti-HER2 (Trastuzumab) | IgG1 | 73 |
| Anti-TNF-α (Adalimumab) | IgG1 | 90 |
| | IgG2 | 90 |
| | IgG3 | 90 |
| | IgG4 | 90 |
| | IgA1 | 90 |
| | IgA2 | 90 |
| Anti-RANK-L (Denosumab) | IgG1 | 98 |
| | IgG2 | 98 |
| | IgG3 | 98 |
| | IgG4 | 98 |
| | IgA1 | 98 |
| | IgA2 | 98 |
| Anti-CTLA-4 (Ipilimumab) | IgG1 | 95 |
| Anti-CTLA-4 (Tremelimumab) | IgG1 | 87 |
| Anti-IL 1β (Canakinumab) | IgG1 | 97 |

INN, International nonproprietary name.

Figure 9:
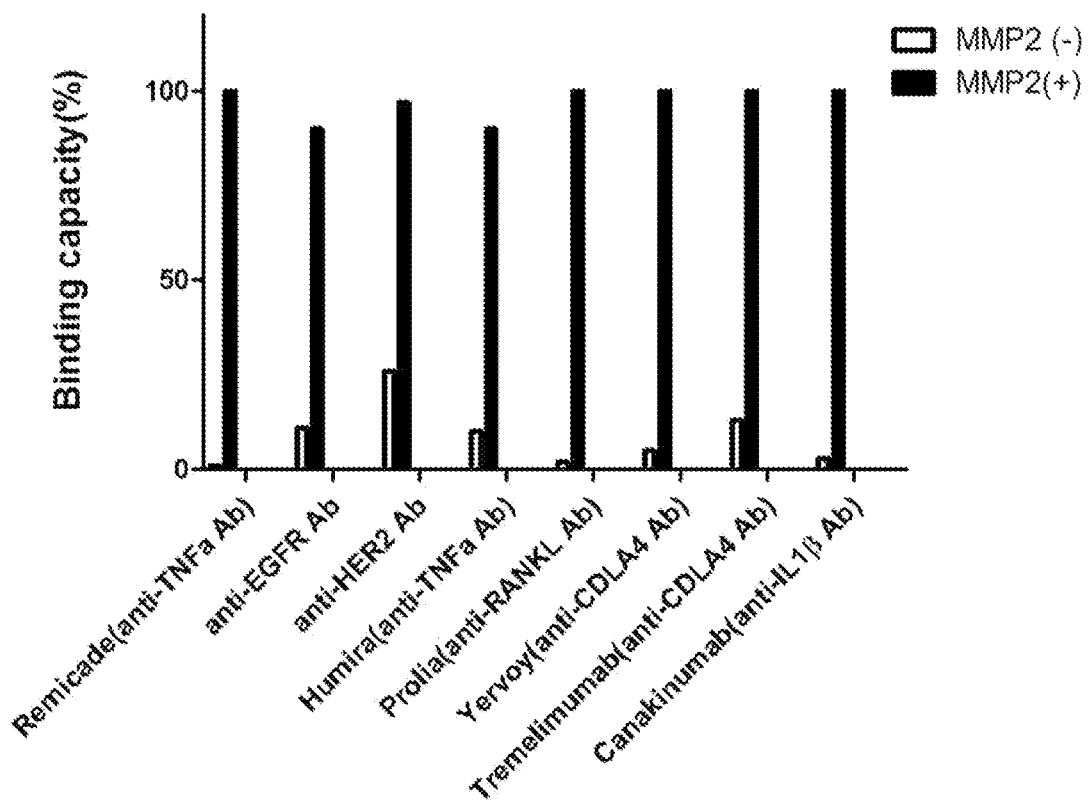
FIG. 9 is a bar graph illustrating the binding capacity of various antibodies according to another working example of the present disclosure.
Figure 10:
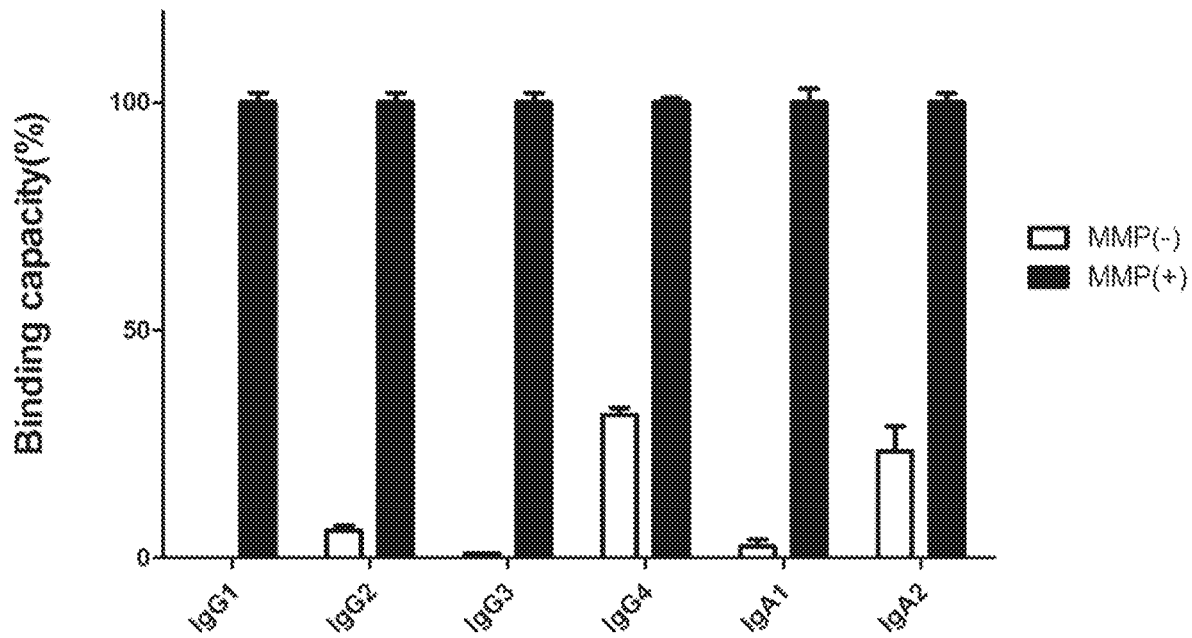
FIG. 10 is a bar graph illustrating the binding capacity of various antibodies according to yet another working example of the present disclosure.
Figure 11:
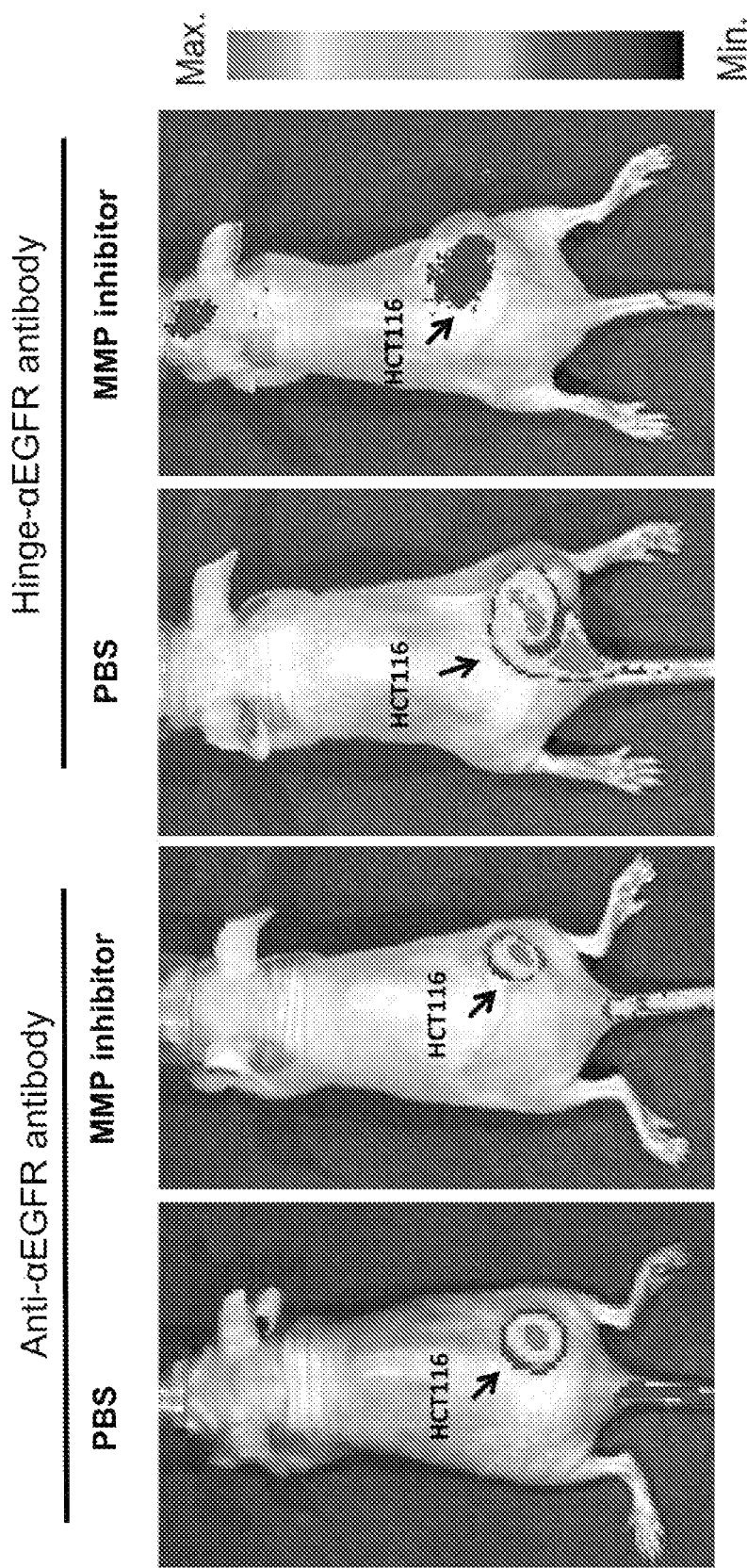
FIG. 11 provides photographs illustrating the in vivo localization and activation of hinge-αEGFR antibody at the tumor site of mice, according to one Example of the present disclosure.

Referring to both FIG. 9 and Table 1, before the MMP2 treatment, the antigen-binding activity of the inactivated IgG1 hinge/MMP2/trastuzumab is about 27%, indicating that about 73% of the binding capability of the functional anti-HER2 domain is inhibited by the attached inhibitory domain. About 1.5 hours after MMP2 treatment, the IgG1 hinge/MMP2/trastuzumab antibodies are substantially activated and the binding capability is restored to about 97%.

The antigen-binding activity of the inactivated IgG1 hinge/MMP2/panitumumab before MMP2 treatment is about 11%, indicating that about 89% of the binding capability of the functional anti-EGFR domain is inhibited by the attached inhibitory domain. Substantial activation of the IgG1 hinge/MMP2/panitumumab is achieved at around 2 hours after the MMP2 treatment, evidenced by the antigen binding capability of about 90%.

In sum, various IgG1 hinge/MMP2/antibodies exhibit about 73% to 99.5% inhibition to the binding between the hinge antibodies and their respective ligands, and the binding affinity can be restored to about 100% after the MMP2 treatment.

To understand the effect of the hinge domain on the inhibitory effect of the hinge antibody, hinge domains from different immunoglobulins (e.g., IgG 1, IgG 2, IgG 3, IgG 4, IgA1 and IgA2) were attached to the functional antibodies as described above. All of the hinge domains are capable of substantially inhibiting the binding of the hinge antibody to its intended ligand when the hinge antibody is not activated. In particular, the antigen-binding capabilities of IgG1, IgG2, IgG3, IgG4, IgA1, IgA2 hinge/MMP2/anti-TNF-α antibody before MMP2 treatment are 0.5%, 6%, 1%, 31.5%, 2.5% and 23.5%, respectively (FIG. 10). Also, after activation with MMP2, the binding abilities of these activated antibodies are restored to 100% (FIG. 10).

These results indicate that the inhibitory domain proposed by the present invention can block about 73 to 99.5% binding affinity of the functional antibody domain, and the binding affinity of the hinge antibody could be revived to about 90 to 100% by the MMP2 treatment, suggesting that the design scheme of the present hinge antibody could be applied to any clinically-available antibodies.

EXAMPLE 7

Localization and Activation of Hinge-αEGFR Antibody in Animal Model

Panitumumab (an anti-αEGFR antibody) has been used in the treatment of EGFR-expressing colorectal cancer. In this example, a hinge/MMP2/panitumumab (hereinafter, the hinge-αEGFR antibody) was prepared and the in vivo localization and activation were examined using colon tumor-bearing mice.

Anti-αEGFR antibody (panitumumab) and the hinge-αEGFR antibody were prepared in accordance with the protocols set forth in Example 1, above. The anti-αEGFR antibody and hinge-αEGFR antibody were then conjugated with a commercially available cyanine dye, IR820 (purchased from Sigma 543365).

Nude mice with an average body weight of 20 grams were transplanted with human colon cancer cells, HCT116 (EGFR+/MMP+. The HCT116 (EGFR+/MMP+) colon tumor-bearing mice were i.v. injected with 5 mg/kg of IR820-anti-αEGFR antibody or the IR820-hinge-αEGFR antibody with PBS or MMP inhibitor (5 mg/kg of 1.10-phenanthroline monohydrate purchased from Sigma). The optical imaging was carried out 48 hours after the injection by imaging the mice with an IVIS Spectrum/CT imaging system (Caliper Life Sciences, PE) at excitation and emission wavelengths of 710 and 820 nm, respectively. During the imaging procedure, mice were kept under gaseous anesthesia (5% isoflurane) at 37° C. Representative images are provided in FIG. 11.

The optical imaging provides a quantitative measure of the 3-dimensional distribution of a fluorescent-signal administered to a live subject noninvasively. In theory, the hinge-αEGFR antibody, once reached the tumor site would be activated under the action of the MMP2 protease, and then the activated functional antibody could bind with the EGFR-positive tumor cells.

As can be seen in FIG. 11, the activated hinge-αEGFR antibody (the third image from the left), like the anti-αEGFR antibody (the first image from the left), was selectively localized to the tumor site. Further, judging by the color recorded in the images, the accumulation level of the activated hinge-αEGFR antibody at the tumor site was equivalent to that of the anti-αEGFR antibody at the tumor site.

Moreover, by comparing the two sets of images respectively treated with anti-αEGFR antibody and hinge-αEGFR antibody in FIG. 11, it is noted that in the presence of MMP inhibitor, less hinge-αEGFR antibody was activated and bound to the EGFR-positive tumor cells. These data indicated that the activation of the hinge-αEGFR antibody was inhibited by MMP inhibitor. Also, this result confirmed that the activation of the hinge/MMP2 antibody according to embodiments of the present disclosure is accomplished by the action of the cleavage enzyme (such as the MMP2).

EXAMPLE 8

Anti-inflammatory Effects of Hinge-TNFα Antibody in Animal Model

Anti-TNFα antibody, such as adalimumab, has been used to treat several conditions where the suppression of the immune response is desired. In this example, the efficacy of IgG1 hinge/MMP2/adalimumab (hereinafter, the hinge-TNFα antibody) for treating collagen-induced arthritis (CIA) was investigated. CIA is a chronic autoimmune model of human rheumatoid arthritis and is widely used for dissecting molecular and cellular mediators of rheumatoid arthritis.

Anti-TNFα antibody (adalimumab) and the hinge-TNFα antibody were prepared in accordance with the protocols set forth in Example 1, above.

Animal model of collagen-induced arthritis was established as follows. Male DBA/1 mice (8 to 10 weeks old) were immunized by intradermal injection at the base of the tail with 100 μg of bovine type II collagen (Chondrex, Inc., Redmond, Wash., USA) emulsified with equal volumes of Freund's complete adjuvant (Chondrex, Inc., Redmond, Wash., USA). The procedure was repeated three weeks after the first immunization. Mice were inspected every 2 to 3 days and each mouse that exhibited erythema and/or paw swelling in one or more limbs was assigned to treatment study. At the onset of arthritis, mice were given an i.p. injection of PBS, anti-TNFα antibody or hinge-TNFα antibody (100 μg/mice). The inflammation of the 4 paws was graded from 0 to 4 as follows: 0=no swelling and focal redness; 1=swelling of finger joints; 2=slight swelling of ankle or wrist joints; 3=severe inflammation of the entire paw; and 4=deformity or ankylosis. Each paw was graded and the 4 scores were totaled, and hence the maximum possible inflammation score per mouse was 16. The results are summarized in FIG. 12.

Figure 12:
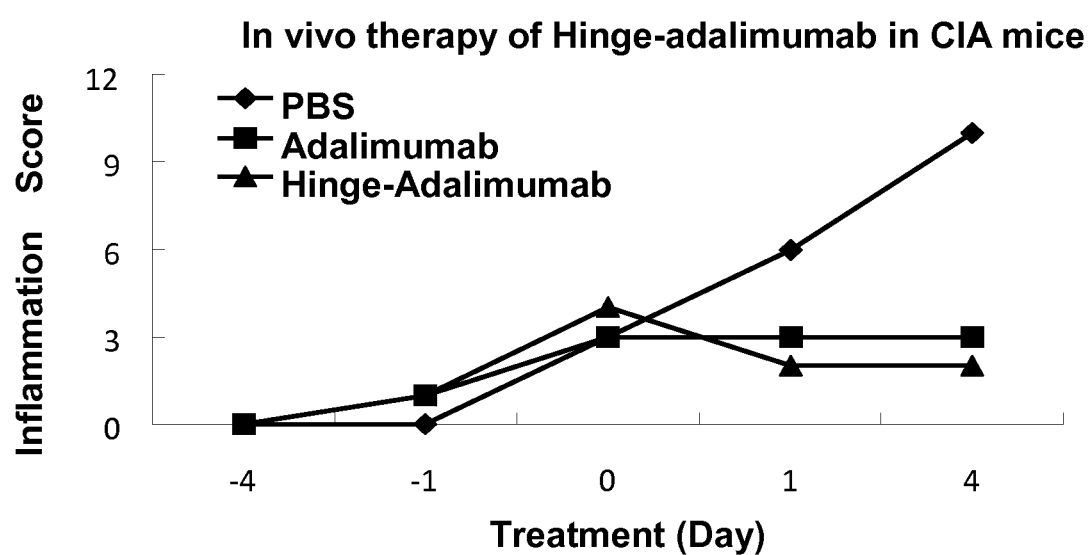
FIG. 12 is line graph indicating the in vivo anti-inflammatory effects of hinge-TNFα antibody against collagen-induced arthritis.

The data in FIG. 12 indicated that the inflammation scores of mice treated with anti-TNFα antibody (adalimumab) and the hinge-TNFα antibody were significantly lowered than those treated with PBS. Moreover, the inflammation scores of mice treated with the present hinge-TNFα antibody were lower than the scores of those treated with the commercially-available anti-TNFα antibody. Therefore, these data evidenced that the present hinge-TNFα antibody can be used to treat rheumatoid arthritis.

It should be noted that, although the hinge antibodies of the above embodiments and working examples are derived from monoclonal antibodies, the present disclosure is not limited thereto. Rather, the design scheme provided by the present application is applicable to other antibody-based therapeutics. For example, the inhibitory domain proposed in this disclosure can be attached to the N-termini of a bispecific antibody (e.g., catumaxomab) in a way similar to those discussed herein. Other antibody-based therapeutics suitable for use in the present invention include, but are not limited to, bispecific diabody, trispecific $Fab_3$ antibodies, bivalent minibodies, triabody, tetrabody, scFv fragments, Fab fragments, and Bis-scFv fragments.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A hinge antibody capable of being selectively activated in a target cell or tissue to treat a condition therein, comprising:
   a functional antibody capable of treating the condition in an activated state, comprising two pairs of light chains and heavy chains;
   two inhibitory domains, wherein each inhibitory domain consists of two peptide arms interconnected by two disulfide bonds; and
   four cleavable linkers, wherein each cleavable linker comprises a peptide substrate cleavable by an enzyme that is specifically or highly expressed in the target cell or tissue;
   wherein the four cleavable linkers connect the four peptide arms of the two inhibitory domains and four N-terminals of the two pairs of light chains and heavy chains of the functional antibody to block antigen binding sites of the two pairs of the light chains and heavy chains of the functional antibody until the functional antibody is selectively activated by cleavage of the cleavable linkers.

2. The hinge antibody of claim 1, wherein the functional antibody is selected from the group consisting of, anti-TNF-a antibody, anti-RANKL antibody, anti-CTLA-4 antibody, anti-HER2 antibody, anti-EGFR antibody, anti-VEGF antibody, anti-VEGFR2) antibody, anti-IL6R antibody, anti-IL12/23 antibody, anti-CD3 antibody, anti-CD11a antibody, anti-CD20 antibody, anti-CD25 antibody, anti-CD30 antibody, anti-CD33 antibody and anti-CD52 antibody.

3. The hinge antibody of claim 1, wherein the light chain of the functional antibody has any of the amino acid sequences of SEQ ID Nos. 1, 2, 3, 4, 5, 6, 7, 8 or 9, and the heavy chain of the functional antibody has any of the amino acid sequences of SEQ ID Nos. 58, 59, 60, 61, 62, 63, 64, 65 and 66.

4. The hinge antibody of claim 1, wherein each of the two inhibitory domains is a hinge domain of an immunoglobulin A (IgA), immunoglobulin D (IgD) or an immunoglobulin G (IgG), or a fragment of the hinge domain.

5. The hinge antibody of claim 4, wherein the hinge domain is a hinge domain of the IgA, and the IgA is IgA1 or IgA2.

6. The hinge antibody of claim 4, wherein the hinge domain is a hinge domain of the IgA, and the IgG is IgG1, IgG2, IgG3 or IgG4.

7. The hinge antibody of claim 4, wherein each of the inhibitory domains comprises any of the amino acid sequences of SEQ ID Nos. 10, 11, 12, 13, 14, 15, 54 or 55.

8. The hinge antibody of claim 1, wherein the peptide substrate is cleavable by any of the following enzyme: a matrix metalloproteinase (MMP), a cathepsin (CTS), a caspase (CASP), or a disintegrin and metalloproteinase (ADAM).

9. The hinge antibody of claim 8, wherein the enzyme is MMP-2 or MMP-9 and each cleavable linker comprises the amino acid sequence of SEQ ID No. 16.

10. The hinge antibody of claim 1, wherein,
   the functional antibody is an anti-TNF-a antibody, wherein the light chain thereof comprises the amino acid sequence of SEQ ID No. 1, and the heavy chain thereof comprises the amino acid sequence of SEQ ID No. 58;
   each of the cleavable linkers comprises the amino acid sequence of SEQ ID No. 16; and
   each of the inhibitory domains comprises the amino acid sequence of SEQ ID No. 10.

* * * * *